(12) United States Patent
Baca et al.

(10) Patent No.: US 10,975,155 B2
(45) Date of Patent: Apr. 13, 2021

(54) CD40L-FC FUSION POLYPEPTIDES AND METHODS OF USE THEREOF

(71) Applicant: MedImmune, LLC, Gaithersburg, MD (US)

(72) Inventors: Manuel Baca, Gaithersburg, MD (US); Stacey Drabic, Gaithersburg, MD (US); Peter Emtage, San Francisco, CA (US); Ronald Herbst, Gaithersburg, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 654 days.

(21) Appl. No.: 15/593,869

(22) Filed: May 12, 2017

(65) Prior Publication Data

US 2017/0327588 A1 Nov. 16, 2017

Related U.S. Application Data

(60) Provisional application No. 62/336,129, filed on May 13, 2016.

(51) Int. Cl.
| | | |
|---|---|---|
| *C07K 16/28* | (2006.01) | |
| *C07K 14/705* | (2006.01) | |
| *C07K 16/30* | (2006.01) | |
| *C07K 16/32* | (2006.01) | |
| *C12N 15/62* | (2006.01) | |
| *A61K 38/00* | (2006.01) | |
| *C12P 21/00* | (2006.01) | |

(52) U.S. Cl.
CPC .... *C07K 16/2878* (2013.01); *C07K 14/70575* (2013.01); *C07K 16/30* (2013.01); *C07K 16/32* (2013.01); *C12N 15/62* (2013.01); *A61K 38/00* (2013.01); *C07K 2317/30* (2013.01); *C07K 2319/30* (2013.01); *C12P 21/00* (2013.01)

(58) Field of Classification Search
None
See application file for complete search history.

(56) References Cited

U.S. PATENT DOCUMENTS

| | | | |
|---|---|---|---|
| 9,340,599 B2* | 5/2016 | Hill | A61P 25/28 |
| 9,724,390 B2* | 8/2017 | Gurney | C07K 14/00 |
| 2002/0076405 A1 | 6/2002 | Leung | |
| 2003/0119149 A1 | 6/2003 | Reddy | |
| 2010/0022452 A1 | 1/2010 | Silence | |
| 2011/0162095 A1 | 6/2011 | Hill | |
| 2015/0125419 A1 | 5/2015 | Hill et al. | |

FOREIGN PATENT DOCUMENTS

| | | |
|---|---|---|
| WO | WO2010/010051 A1 | 1/2010 |
| WO | WO2016/177771 A9 | 11/2016 |

OTHER PUBLICATIONS

UniProtKB—P29965, "CD40 ligand," (Apr. 1, 1993) [retrieved on Aug. 5, 2017, http://www.uniprot.org/uniprot/P29965] p. 2, CD40L protein sequence.

\* cited by examiner

*Primary Examiner* — Patricia Duffy

(57) ABSTRACT

Provided herein is a CD40L-Fc fusion protein and methods of using the fusion protein in the treatment of cancer comprising administering the CD40L-Fc fusion protein or the CD40L-Fc fusion protein in combination with one or more immune checkpoint inhibitors (e.g., an anti-CTLA4 antibody, anti-PD-L1 antibody).

2 Claims, 27 Drawing Sheets

Specification includes a Sequence Listing.

FIG. 17
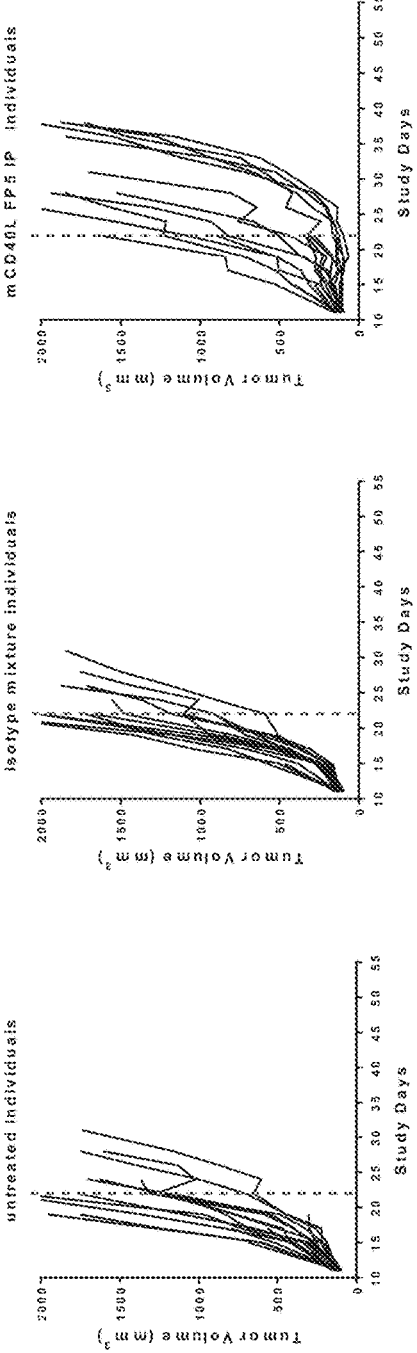
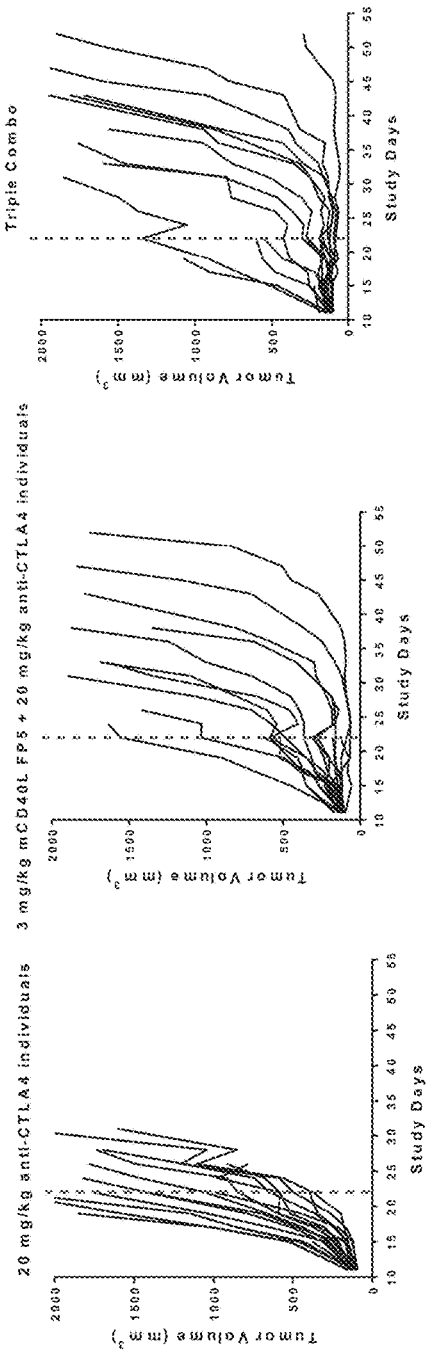

SEQUENCE LISTING

<160> NUMBER OF SEQ ID NOS: 37

<210> SEQ ID NO 1
<211> LENGTH: 143
<212> TYPE: PRT
<213> ORGANISM: Artificial Sequence
<220> FEATURE:
<223> OTHER INFORMATION: CD40L variant

<400> SEQUENCE: 1

Asn Pro Gln Ile Ala Ala His Val Ile Ser Glu Ala Ser Ser Lys Thr
1               5                   10                  15

Thr Ser Val Leu Gln Trp Ala Glu Lys Gly Tyr Tyr Thr Met Ser Asn
            20                  25                  30

Asn Leu Val Thr Leu Glu Asn Gly Lys Gln Leu Thr Val Lys Arg Gln
        35                  40                  45

Gly Leu Tyr Tyr Ile Tyr Ala Gln Val Thr Phe Cys Ser Asn Arg Glu
    50                  55                  60

Ala Ser Ser Gln Ala Pro Phe Ile Ala Ser Leu Trp Leu Lys Ser Pro
65                  70                  75                  80

Gly Arg Phe Glu Arg Ile Leu Leu Arg Ala Ala Asn Thr His Ser Ser
                85                  90                  95

Ala Lys Pro Cys Gly Gln Gln Ser Ile His Leu Gly Gly Val Phe Glu
            100                 105                 110

Leu Gln Pro Gly Ala Ser Val Phe Val Asn Val Thr Asp Pro Ser Gln
        115                 120                 125

Val Ser His Gly Thr Gly Phe Thr Ser Phe Gly Leu Leu Lys Leu
    130                 135                 140

<210> SEQ ID NO 2
<211> LENGTH: 9
<212> TYPE: PRT
<213> ORGANISM: Artificial Sequence
<220> FEATURE:
<223> OTHER INFORMATION: Peptide Linker

<400> SEQUENCE: 2

Gly Gly Gly Gly Ser Gly Gly Gly Ser
1               5

<210> SEQ ID NO 3
<211> LENGTH: 141
<212> TYPE: PRT
<213> ORGANISM: Artificial Sequence
<220> FEATURE:
<223> OTHER INFORMATION: CD40L variant

<400> SEQUENCE: 3

Gln Ile Ala Ala His Val Ile Ser Glu Ala Ser Ser Lys Thr Thr Ser
1               5                   10                  15

Val Leu Gln Trp Ala Glu Lys Gly Tyr Tyr Thr Met Ser Asn Asn Leu
            20                  25                  30

Val Thr Leu Glu Asn Gly Lys Gln Leu Thr Val Lys Arg Gln Gly Leu
        35                  40                  45

Tyr Tyr Ile Tyr Ala Gln Val Thr Phe Cys Ser Asn Arg Glu Ala Ser
    50                  55                  60

Ser Gln Ala Pro Phe Ile Ala Ser Leu Trp Leu Lys Ser Pro Gly Arg
65                  70                  75                  80

Phe Glu Arg Ile Leu Leu Arg Ala Ala Asn Thr His Ser Ser Ala Lys
                85                  90                  95

```
Pro Cys Gly Gln Gln Ser Ile His Leu Gly Gly Val Phe Glu Leu Gln
            100                 105                 110

Pro Gly Ala Ser Val Phe Val Asn Val Thr Asp Pro Ser Gln Val Ser
        115                 120                 125

His Gly Thr Gly Phe Thr Ser Phe Gly Leu Leu Lys Leu
    130                 135                 140

<210> SEQ ID NO 4
<211> LENGTH: 15
<212> TYPE: PRT
<213> ORGANISM: Artificial Sequence
<220> FEATURE:
<223> OTHER INFORMATION: Peptide linker

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 5
<212> TYPE: PRT
<213> ORGANISM: Artificial Sequence
<220> FEATURE:
<223> OTHER INFORMATION: Peptide linker

<400> SEQUENCE: 5

Gly Gly Gly Gly Ser
1               5

<210> SEQ ID NO 6
<211> LENGTH: 4
<212> TYPE: PRT
<213> ORGANISM: Artificial Sequence
<220> FEATURE:
<223> OTHER INFORMATION: Peptide linker

<400> SEQUENCE: 6

Gly Gly Gly Ser
1

<210> SEQ ID NO 7
<211> LENGTH: 5
<212> TYPE: PRT
<213> ORGANISM: Artificial Sequence
<220> FEATURE:
<223> OTHER INFORMATION: Peptide linker

<400> SEQUENCE: 7

Gly Gly Gly Gly Ser
1               5

<210> SEQ ID NO 8
<211> LENGTH: 4
<212> TYPE: PRT
<213> ORGANISM: Artificial Sequence
<220> FEATURE:
<223> OTHER INFORMATION: Peptide linker

<400> SEQUENCE: 8

Gly Gly Gly Ser
1

<210> SEQ ID NO 9
<211> LENGTH: 687
<212> TYPE: PRT
```

<213> ORGANISM: Artificial Sequence
<220> FEATURE:
<223> OTHER INFORMATION: MEDI5083

<400> SEQUENCE: 9

```
Asn Pro Gln Ile Ala Ala His Val Ile Ser Glu Ala Ser Ser Lys Thr
1               5                   10                  15

Thr Ser Val Leu Gln Trp Ala Glu Lys Gly Tyr Tyr Thr Met Ser Asn
            20                  25                  30

Asn Leu Val Thr Leu Glu Asn Gly Lys Gln Leu Thr Val Lys Arg Gln
        35                  40                  45

Gly Leu Tyr Tyr Ile Tyr Ala Gln Val Thr Phe Cys Ser Asn Arg Glu
    50                  55                  60

Ala Ser Ser Gln Ala Pro Phe Ile Ala Ser Leu Trp Leu Lys Ser Pro
65                  70                  75                  80

Gly Arg Phe Glu Arg Ile Leu Leu Arg Ala Ala Asn Thr His Ser Ser
                85                  90                  95

Ala Lys Pro Cys Gly Gln Gln Ser Ile His Leu Gly Gly Val Phe Glu
            100                 105                 110

Leu Gln Pro Gly Ala Ser Val Phe Val Asn Val Thr Asp Pro Ser Gln
        115                 120                 125

Val Ser His Gly Thr Gly Phe Thr Ser Phe Gly Leu Leu Lys Leu Gly
    130                 135                 140

Gly Gly Gly Ser Gly Gly Gly Ser Gln Ile Ala Ala His Val Ile Ser
145                 150                 155                 160

Glu Ala Ser Ser Lys Thr Thr Ser Val Leu Gln Trp Ala Glu Lys Gly
                165                 170                 175

Tyr Tyr Thr Met Ser Asn Asn Leu Val Thr Leu Glu Asn Gly Lys Gln
            180                 185                 190

Leu Thr Val Lys Arg Gln Gly Leu Tyr Tyr Ile Tyr Ala Gln Val Thr
        195                 200                 205

Phe Cys Ser Asn Arg Glu Ala Ser Ser Gln Ala Pro Phe Ile Ala Ser
    210                 215                 220

Leu Trp Leu Lys Ser Pro Gly Arg Phe Glu Arg Ile Leu Leu Arg Ala
225                 230                 235                 240

Ala Asn Thr His Ser Ser Ala Lys Pro Cys Gly Gln Gln Ser Ile His
                245                 250                 255

Leu Gly Gly Val Phe Glu Leu Gln Pro Gly Ala Ser Val Phe Val Asn
            260                 265                 270

Val Thr Asp Pro Ser Gln Val Ser His Gly Thr Gly Phe Thr Ser Phe
        275                 280                 285

Gly Leu Leu Lys Leu Gly Gly Gly Ser Gly Gly Gly Ser Gln Ile
    290                 295                 300

Ala Ala His Val Ile Ser Glu Ala Ser Ser Lys Thr Thr Ser Val Leu
305                 310                 315                 320

Gln Trp Ala Glu Lys Gly Tyr Tyr Thr Met Ser Asn Asn Leu Val Thr
                325                 330                 335

Leu Glu Asn Gly Lys Gln Leu Thr Val Lys Arg Gln Gly Leu Tyr Tyr
            340                 345                 350

Ile Tyr Ala Gln Val Thr Phe Cys Ser Asn Arg Glu Ala Ser Ser Gln
        355                 360                 365

Ala Pro Phe Ile Ala Ser Leu Trp Leu Lys Ser Pro Gly Arg Phe Glu
    370                 375                 380

Arg Ile Leu Leu Arg Ala Ala Asn Thr His Ser Ser Ala Lys Pro Cys
```

-continued

```
                385                 390                 395                 400
        Gly Gln Gln Ser Ile His Leu Gly Gly Val Phe Glu Leu Gln Pro Gly
                        405                 410                 415

Ala Ser Val Phe Val Asn Val Thr Asp Pro Ser Gln Val Ser His Gly
                        420                 425                 430

Thr Gly Phe Thr Ser Phe Gly Leu Leu Lys Leu Gly Gly Gly Gly Ser
                        435                 440                 445

Gly Gly Gly Gly Ser Gly Gly Gly Ser Glu Ser Lys Tyr Gly Pro
                450                 455                 460

Pro Cys Pro Pro Cys Pro Ala Pro Glu Phe Leu Gly Gly Pro Ser Val
        465                 470                 475                 480

Phe Leu Phe Pro Pro Lys Pro Lys Asp Thr Leu Met Ile Ser Arg Thr
                        485                 490                 495

Pro Glu Val Thr Cys Val Val Val Asp Val Ser Gln Glu Asp Pro Glu
                        500                 505                 510

Val Gln Phe Asn Trp Tyr Val Asp Gly Val Glu Val His Asn Ala Lys
                        515                 520                 525

Thr Lys Pro Arg Glu Glu Gln Phe Asn Ser Thr Tyr Arg Val Val Ser
                530                 535                 540

Val Leu Thr Val Leu His Gln Asp Trp Leu Asn Gly Lys Glu Tyr Lys
        545                 550                 555                 560

Cys Lys Val Ser Asn Lys Gly Leu Pro Ser Ser Ile Glu Lys Thr Ile
                        565                 570                 575

Ser Lys Ala Lys Gly Gln Pro Arg Glu Pro Gln Val Tyr Thr Leu Pro
                        580                 585                 590

Pro Ser Gln Glu Glu Met Thr Lys Asn Gln Val Ser Leu Thr Cys Leu
                        595                 600                 605

Val Lys Gly Phe Tyr Pro Ser Asp Ile Ala Val Glu Trp Glu Ser Asn
                        610                 615                 620

Gly Gln Pro Glu Asn Asn Tyr Lys Thr Thr Pro Pro Val Leu Asp Ser
        625                 630                 635                 640

Asp Gly Ser Phe Phe Leu Tyr Ser Arg Leu Thr Val Asp Lys Ser Arg
                        645                 650                 655

Trp Gln Glu Gly Asn Val Phe Ser Cys Ser Val Met His Glu Ala Leu
                        660                 665                 670

His Asn His Tyr Thr Gln Lys Ser Leu Ser Leu Ser Leu Gly Lys
                        675                 680                 685

<210> SEQ ID NO 10
<211> LENGTH: 699
<212> TYPE: PRT
<213> ORGANISM: Artificial Sequence
<220> FEATURE:
<223> OTHER INFORMATION: scCD40L-IgG4P-FP7

<400> SEQUENCE: 10

Asn Pro Gln Ile Ala Ala His Val Ile Ser Glu Ala Ser Ser Lys Thr
        1               5                   10                  15

Thr Ser Val Leu Gln Trp Ala Glu Lys Gly Tyr Tyr Thr Met Ser Asn
                        20                  25                  30

Asn Leu Val Thr Leu Glu Asn Gly Lys Gln Leu Thr Val Lys Arg Gln
                        35                  40                  45

Gly Leu Tyr Tyr Ile Tyr Ala Gln Val Thr Phe Cys Ser Asn Arg Glu
                50                  55                  60

Ala Ser Ser Gln Ala Pro Phe Ile Ala Ser Leu Trp Leu Lys Ser Pro
```

-continued

```
             65                  70                  75                  80
Gly Arg Phe Glu Arg Ile Leu Leu Arg Ala Ala Asn Thr His Ser Ser
                     85                  90                  95
Ala Lys Pro Cys Gly Gln Gln Ser Ile His Leu Gly Gly Val Phe Glu
                    100                 105                 110
Leu Gln Pro Gly Ala Ser Val Phe Val Asn Val Thr Asp Pro Ser Gln
                    115                 120                 125
Val Ser His Gly Thr Gly Phe Thr Ser Phe Gly Leu Leu Lys Leu Gly
                    130                 135                 140
Gly Gly Ser Gly Gly Gly Ser Gly Gly Gly Ser Gln Ile
145                 150                 155                 160
Ala Ala His Val Ile Ser Glu Ala Ser Ser Lys Thr Thr Ser Val Leu
                    165                 170                 175
Gln Trp Ala Glu Lys Gly Tyr Tyr Thr Met Ser Asn Asn Leu Val Thr
                    180                 185                 190
Leu Glu Asn Gly Lys Gln Leu Thr Val Lys Arg Gln Gly Leu Tyr Tyr
                    195                 200                 205
Ile Tyr Ala Gln Val Thr Phe Cys Ser Asn Arg Glu Ala Ser Ser Gln
                    210                 215                 220
Ala Pro Phe Ile Ala Ser Leu Trp Leu Lys Ser Pro Gly Arg Phe Glu
225                 230                 235                 240
Arg Ile Leu Leu Arg Ala Ala Asn Thr His Ser Ser Ala Lys Pro Cys
                    245                 250                 255
Gly Gln Gln Ser Ile His Leu Gly Gly Val Phe Glu Leu Gln Pro Gly
                    260                 265                 270
Ala Ser Val Phe Val Asn Val Thr Asp Pro Ser Gln Val Ser His Gly
                    275                 280                 285
Thr Gly Phe Thr Ser Phe Gly Leu Leu Lys Leu Gly Gly Gly Ser
                    290                 295                 300
Gly Gly Gly Gly Ser Gly Gly Gly Ser Gln Ile Ala Ala His Val
305                 310                 315                 320
Ile Ser Glu Ala Ser Ser Lys Thr Thr Ser Val Leu Gln Trp Ala Glu
                    325                 330                 335
Lys Gly Tyr Tyr Thr Met Ser Asn Asn Leu Val Thr Leu Glu Asn Gly
                    340                 345                 350
Lys Gln Leu Thr Val Lys Arg Gln Gly Leu Tyr Tyr Ile Tyr Ala Gln
                    355                 360                 365
Val Thr Phe Cys Ser Asn Arg Glu Ala Ser Ser Gln Ala Pro Phe Ile
                    370                 375                 380
Ala Ser Leu Trp Leu Lys Ser Pro Gly Arg Phe Glu Arg Ile Leu Leu
385                 390                 395                 400
Arg Ala Ala Asn Thr His Ser Ser Ala Lys Pro Cys Gly Gln Gln Ser
                    405                 410                 415
Ile His Leu Gly Gly Val Phe Glu Leu Gln Pro Gly Ala Ser Val Phe
                    420                 425                 430
Val Asn Val Thr Asp Pro Ser Gln Val Ser His Gly Thr Gly Phe Thr
                    435                 440                 445
Ser Phe Gly Leu Leu Lys Leu Gly Gly Gly Ser Gly Gly Gly
                    450                 455                 460
Ser Gly Gly Gly Ser Glu Ser Lys Tyr Gly Pro Pro Cys Pro Pro
465                 470                 475                 480
Cys Pro Ala Pro Glu Phe Leu Gly Gly Pro Ser Val Phe Leu Phe Pro
                    485                 490                 495
```

```
Pro Lys Pro Lys Asp Thr Leu Met Ile Ser Arg Thr Pro Glu Val Thr
            500                 505                 510

Cys Val Val Asp Val Ser Gln Glu Asp Pro Glu Val Gln Phe Asn
        515                 520                 525

Trp Tyr Val Asp Gly Val Glu Val His Asn Ala Lys Thr Lys Pro Arg
530                 535                 540

Glu Glu Gln Phe Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Gly Leu Pro Ser Ser Ile Glu Lys Thr Ile Ser Lys Ala Lys
                580                 585                 590

Gly Gln Pro Arg Glu Pro Gln Val Tyr Thr Leu Pro Pro Ser Gln Glu
            595                 600                 605

Glu Met Thr Lys Asn Gln Val Ser Leu Thr Cys Leu Val Lys Gly Phe
610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Arg Leu Thr Val Asp Lys Ser Arg Trp Gln Glu Gly
                660                 665                 670

Asn Val Phe Ser Cys Ser Val Met His Glu Ala Leu His Asn His Tyr
                675                 680                 685

Thr Gln Lys Ser Leu Ser Leu Ser Leu Gly Lys
            690                 695

<210> SEQ ID NO 11
<211> LENGTH: 681
<212> TYPE: PRT
<213> ORGANISM: Artificial Sequence
<220> FEATURE:
<223> OTHER INFORMATION: FP5-like, mouse IgG1 D265A

<400> SEQUENCE: 11

Asp Pro Gln Ile Ala Ala His Val Val Ser Glu Ala Asn Ser Asn Ala
1               5                   10                  15

Ala Ser Val Leu Gln Trp Ala Lys Lys Gly Tyr Tyr Thr Met Lys Ser
            20                  25                  30

Asn Leu Val Met Leu Glu Asn Gly Lys Gln Leu Thr Val Lys Arg Glu
        35                  40                  45

Gly Leu Tyr Tyr Val Tyr Thr Gln Val Thr Phe Cys Ser Asn Arg Glu
    50                  55                  60

Pro Ser Ser Gln Arg Pro Phe Ile Val Gly Leu Trp Leu Lys Pro Ser
65                  70                  75                  80

Ser Gly Ser Glu Arg Ile Leu Leu Lys Ala Ala Asn Thr His Ser Ser
                85                  90                  95

Ser Gln Leu Cys Glu Gln Gln Ser Val His Leu Gly Gly Val Phe Glu
            100                 105                 110

Leu Gln Ala Gly Ala Ser Val Phe Val Asn Val Thr Glu Ala Ser Gln
        115                 120                 125

Val Ile His Arg Val Gly Phe Ser Ser Phe Gly Leu Leu Lys Leu Gly
    130                 135                 140

Gly Gly Ser Gly Gly Ser Gln Ile Ala Ala His Val Val Ser Glu Ala
145                 150                 155                 160
```

```
Asn Ser Asn Ala Ala Ser Val Leu Gln Trp Ala Lys Lys Gly Tyr Tyr
            165                 170                 175

Thr Met Lys Ser Asn Leu Val Met Leu Glu Asn Gly Lys Gln Leu Thr
            180                 185                 190

Val Lys Arg Glu Gly Leu Tyr Tyr Val Tyr Thr Gln Val Thr Phe Cys
            195                 200                 205

Ser Asn Arg Glu Pro Ser Ser Gln Arg Pro Phe Ile Val Gly Leu Trp
            210                 215                 220

Leu Lys Pro Ser Ser Gly Ser Glu Arg Ile Leu Leu Lys Ala Ala Asn
225                 230                 235                 240

Thr His Ser Ser Ser Gln Leu Cys Glu Gln Gln Ser Val His Leu Gly
            245                 250                 255

Gly Val Phe Glu Leu Gln Ala Gly Ala Ser Val Phe Val Asn Val Thr
            260                 265                 270

Glu Ala Ser Gln Val Ile His Arg Val Gly Phe Ser Ser Phe Gly Leu
            275                 280                 285

Leu Lys Leu Gly Gly Gly Ser Gly Gly Ser Gln Ile Ala Ala His Val
            290                 295                 300

Val Ser Glu Ala Asn Ser Asn Ala Ala Ser Val Leu Gln Trp Ala Lys
305                 310                 315                 320

Lys Gly Tyr Tyr Thr Met Lys Ser Asn Leu Val Met Leu Glu Asn Gly
            325                 330                 335

Lys Gln Leu Thr Val Lys Arg Glu Gly Leu Tyr Tyr Val Tyr Thr Gln
            340                 345                 350

Val Thr Phe Cys Ser Asn Arg Glu Pro Ser Ser Gln Arg Pro Phe Ile
            355                 360                 365

Val Gly Leu Trp Leu Lys Pro Ser Ser Gly Ser Glu Arg Ile Leu Leu
            370                 375                 380

Lys Ala Ala Asn Thr His Ser Ser Ser Gln Leu Cys Glu Gln Gln Ser
385                 390                 395                 400

Val His Leu Gly Gly Val Phe Glu Leu Gln Ala Gly Ala Ser Val Phe
            405                 410                 415

Val Asn Val Thr Glu Ala Ser Gln Val Ile His Arg Val Gly Phe Ser
            420                 425                 430

Ser Phe Gly Leu Leu Lys Leu Gly Gly Gly Ser Gly Gly Gly Gly
            435                 440                 445

Ser Gly Gly Gly Gly Ser Val Pro Arg Asp Cys Gly Cys Lys Pro Cys
450                 455                 460

Ile Cys Thr Val Pro Glu Val Ser Ser Val Phe Ile Phe Pro Pro Lys
465                 470                 475                 480

Pro Lys Asp Val Leu Thr Ile Thr Leu Thr Pro Lys Val Thr Cys Val
            485                 490                 495

Val Val Ala Ile Ser Lys Asp Asp Pro Glu Val Gln Phe Ser Trp Phe
            500                 505                 510

Val Asp Asp Val Glu Val His Thr Ala Gln Thr Gln Pro Arg Glu Glu
            515                 520                 525

Gln Phe Asn Ser Thr Phe Arg Ser Val Ser Glu Leu Pro Ile Met His
            530                 535                 540

Gln Asp Trp Leu Asn Gly Lys Glu Phe Lys Cys Arg Val Asn Ser Ala
545                 550                 555                 560

Ala Phe Pro Ala Pro Ile Glu Lys Thr Ile Ser Lys Thr Lys Gly Arg
            565                 570                 575
```

```
Pro Lys Ala Pro Gln Val Tyr Thr Ile Pro Pro Lys Glu Gln Met
            580                 585                 590
Ala Lys Asp Lys Val Ser Leu Thr Cys Met Ile Thr Asp Phe Phe Pro
        595                 600                 605
Glu Asp Ile Thr Val Glu Trp Gln Trp Asn Gly Gln Pro Ala Glu Asn
    610                 615                 620
Tyr Lys Asn Thr Gln Pro Ile Met Asp Thr Asp Gly Ser Tyr Phe Val
625                 630                 635                 640
Tyr Ser Lys Leu Asn Val Gln Lys Ser Asn Trp Glu Ala Gly Asn Thr
            645                 650                 655
Phe Thr Cys Ser Val Leu His Glu Gly Leu His Asn His His Thr Glu
        660                 665                 670
Lys Ser Leu Ser His Ser Pro Gly Lys
            675                 680

<210> SEQ ID NO 12
<211> LENGTH: 261
<212> TYPE: PRT
<213> ORGANISM: Homo sapiens

<400> SEQUENCE: 12

Met Ile Glu Thr Tyr Asn Gln Thr Ser Pro Arg Ser Ala Ala Thr Gly
1               5                   10                  15
Leu Pro Ile Ser Met Lys Ile Phe Met Tyr Leu Leu Thr Val Phe Leu
            20                  25                  30
Ile Thr Gln Met Ile Gly Ser Ala Leu Phe Ala Val Tyr Leu His Arg
        35                  40                  45
Arg Leu Asp Lys Ile Glu Asp Glu Arg Asn Leu His Glu Asp Phe Val
    50                  55                  60
Phe Met Lys Thr Ile Gln Arg Cys Asn Thr Gly Glu Arg Ser Leu Ser
65                  70                  75                  80
Leu Leu Asn Cys Glu Glu Ile Lys Ser Gln Phe Glu Gly Phe Val Lys
            85                  90                  95
Asp Ile Met Leu Asn Lys Glu Glu Thr Lys Lys Glu Asn Ser Phe Glu
        100                 105                 110
Met Gln Lys Gly Asp Gln Asn Pro Gln Ile Ala Ala His Val Ile Ser
    115                 120                 125
Glu Ala Ser Ser Lys Thr Thr Ser Val Leu Gln Trp Ala Glu Lys Gly
130                 135                 140
Tyr Tyr Thr Met Ser Asn Asn Leu Val Thr Leu Glu Asn Gly Lys Gln
145                 150                 155                 160
Leu Thr Val Lys Arg Gln Gly Leu Tyr Tyr Ile Tyr Ala Gln Val Thr
            165                 170                 175
Phe Cys Ser Asn Arg Glu Ala Ser Ser Gln Ala Pro Phe Ile Ala Ser
        180                 185                 190
Leu Cys Leu Lys Ser Pro Gly Arg Phe Glu Arg Ile Leu Leu Arg Ala
    195                 200                 205
Ala Asn Thr His Ser Ser Ala Lys Pro Cys Gly Gln Gln Ser Ile His
210                 215                 220
Leu Gly Gly Val Phe Glu Leu Gln Pro Gly Ala Ser Val Phe Val Asn
225                 230                 235                 240
Val Thr Asp Pro Ser Gln Val Ser His Gly Thr Gly Phe Thr Ser Phe
            245                 250                 255
Gly Leu Leu Lys Leu
        260
```

<210> SEQ ID NO 13
<211> LENGTH: 149
<212> TYPE: PRT
<213> ORGANISM: Homo sapiens

<400> SEQUENCE: 13

```
Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
            20                  25                  30

Tyr Tyr Thr Met Ser Asn Asn Leu Val Thr Leu Glu Asn Gly Lys Gln
        35                  40                  45

Leu Thr Val Lys Arg Gln Gly Leu Tyr Tyr Ile Tyr Ala Gln Val Thr
    50                  55                  60

Phe Cys Ser Asn Arg Glu Ala Ser Ser Gln Ala Pro Phe Ile Ala Ser
65                  70                  75                  80

Leu Cys Leu Lys Ser Pro Gly Arg Phe Glu Arg Ile Leu Leu Arg Ala
                85                  90                  95

Ala Asn Thr His Ser Ser Ala Lys Pro Cys Gly Gln Gln Ser Ile His
            100                 105                 110

Leu Gly Gly Val Phe Glu Leu Gln Pro Gly Ala Ser Val Phe Val Asn
        115                 120                 125

Val Thr Asp Pro Ser Gln Val Ser His Gly Thr Gly Phe Thr Ser Phe
    130                 135                 140

Gly Leu Leu Lys Leu
145
```

<210> SEQ ID NO 14
<211> LENGTH: 277
<212> TYPE: PRT
<213> ORGANISM: Homo sapiens

<400> SEQUENCE: 14

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175
```

```
Ala Gly Thr Asn Lys Thr Asp Val Val Cys Gly Pro Gln Asp Arg Leu
            180                 185                 190

Arg Ala Leu Val Val Ile Pro Ile Phe Gly Ile Leu Phe Ala Ile
        195                 200                 205

Leu Leu Val Leu Val Phe Ile Lys Lys Val Ala Lys Lys Pro Thr Asn
210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
            275

<210> SEQ ID NO 15
<211> LENGTH: 176
<212> TYPE: PRT
<213> ORGANISM: Homo sapiens

<400> SEQUENCE: 15

Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
            20                  25                  30

Val Thr Ser Glu His Glu Leu Thr Cys Gln Ala Glu Gly Tyr Pro Lys
        35                  40                  45

Ala Glu Val Ile Trp Thr Ser Ser Asp His Gln Val Leu Ser Gly Lys
    50                  55                  60

Thr Thr Thr Thr Asn Ser Lys Arg Glu Glu Lys Leu Phe Asn Val Thr
65                  70                  75                  80

Ser Thr Leu Arg Ile Asn Thr Thr Asn Glu Ile Phe Tyr Cys Thr
                85                  90                  95

Phe Arg Arg Leu Asp Pro Glu Glu Asn His Thr Ala Glu Leu Val Ile
                100                 105                 110

Pro Glu Leu Pro Leu Ala His Pro Pro Asn Glu Arg Thr His Leu Val
            115                 120                 125

Ile Leu Gly Ala Ile Leu Leu Cys Leu Gly Val Ala Leu Thr Phe Ile
        130                 135                 140

Phe Arg Leu Arg Lys Gly Arg Met Met Asp Val Lys Lys Cys Gly Ile
145                 150                 155                 160

Gln Asp Thr Asn Ser Lys Lys Gln Ser Asp Thr His Leu Glu Glu Thr
                165                 170                 175

<210> SEQ ID NO 16
<211> LENGTH: 108
<212> TYPE: PRT
<213> ORGANISM: Homo sapiens

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45
```

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 17
<211> LENGTH: 121
<212> TYPE: PRT
<213> ORGANISM: Homo sapiens

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 18
<211> LENGTH: 10
<212> TYPE: PRT
<213> ORGANISM: Homo sapiens

<400> SEQUENCE: 18

Gly Phe Thr Phe Ser Arg Tyr Trp Met Ser
1               5                   10

<210> SEQ ID NO 19
<211> LENGTH: 17
<212> TYPE: PRT
<213> ORGANISM: Homo sapiens

<400> SEQUENCE: 19

Asn Ile Lys Gln Asp Gly Ser Glu Lys Tyr Tyr Val Asp Ser Val Lys
1               5                   10                  15

Gly

<210> SEQ ID NO 20
<211> LENGTH: 12
<212> TYPE: PRT
<213> ORGANISM: Homo sapiens

<400> SEQUENCE: 20

Glu Gly Gly Trp Phe Gly Glu Leu Ala Phe Asp Tyr
1               5                   10

<210> SEQ ID NO 21
<211> LENGTH: 12
<212> TYPE: PRT
<213> ORGANISM: Homo sapiens

<400> SEQUENCE: 21

Arg Ala Ser Gln Arg Val Ser Ser Tyr Leu Ala
1               5                   10

<210> SEQ ID NO 22
<211> LENGTH: 7
<212> TYPE: PRT
<213> ORGANISM: Homo sapiens

<400> SEQUENCE: 22

Asp Ala Ser Ser Arg Ala Thr
1               5

<210> SEQ ID NO 23
<211> LENGTH: 9
<212> TYPE: PRT
<213> ORGANISM: Homo sapiens

<400> SEQUENCE: 23

Gln Gln Tyr Gly Ser Leu Pro Trp Thr
1               5

<210> SEQ ID NO 24
<211> LENGTH: 288
<212> TYPE: PRT
<213> ORGANISM: Homo sapiens

<400> SEQUENCE: 24

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro

```
                195                 200                 205
Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 25
<211> LENGTH: 223
<212> TYPE: PRT
<213> ORGANISM: Homo sapiens

<400> SEQUENCE: 25

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220
```

<210> SEQ ID NO 26
<211> LENGTH: 139
<212> TYPE: PRT
<213> ORGANISM: Homo sapiens

<400> SEQUENCE: 26

```
Pro Ser Ser Leu Ser Ala Ser Val Gly Asp Arg Val Thr Ile Thr Cys
1               5                   10                  15

Arg Ala Ser Gln Ser Ile Asn Ser Tyr Leu Asp Trp Tyr Gln Gln Lys
```

```
                    20                  25                  30

Pro Gly Lys Ala Pro Lys Leu Leu Ile Tyr Ala Ala Ser Ser Leu Gln
            35                  40                  45

Ser Gly Val Pro Ser Arg Phe Ser Gly Ser Gly Ser Gly Thr Asp Phe
        50                  55                  60

Thr Leu Thr Ile Ser Ser Leu Gln Pro Glu Asp Phe Ala Thr Tyr Tyr
 65                 70                  75                  80

Cys Gln Gln Tyr Tyr Ser Thr Pro Phe Thr Phe Gly Pro Gly Thr Lys
                85                  90                  95

Val Glu Ile Lys Arg Thr Val Ala Ala Pro Ser Val Phe Ile Phe Pro
            100                 105                 110

Pro Ser Asp Glu Gln Leu Lys Ser Gly Thr Ala Ser Val Val Cys Leu
        115                 120                 125

Leu Asn Asn Phe Tyr Pro Arg Glu Ala Lys Val
    130                 135

<210> SEQ ID NO 27
<211> LENGTH: 167
<212> TYPE: PRT
<213> ORGANISM: Homo sapiens

<400> SEQUENCE: 27

Gly Val Val Gln Pro Gly Arg Ser Leu Arg Leu Ser Cys Ala Ala Ser
 1               5                  10                  15

Gly Phe Thr Phe Ser Ser Tyr Gly Met His Trp Val Arg Gln Ala Pro
            20                  25                  30

Gly Lys Gly Leu Glu Trp Val Ala Val Ile Trp Tyr Asp Gly Ser Asn
        35                  40                  45

Lys Tyr Tyr Ala Asp Ser Val Lys Gly Arg Phe Thr Ile Ser Arg Asp
    50                  55                  60

Asn Ser Lys Asn Thr Leu Tyr Leu Gln Met Asn Ser Leu Arg Ala Glu
 65                 70                  75                  80

Asp Thr Ala Val Tyr Tyr Cys Ala Arg Asp Pro Arg Gly Ala Thr Leu
                85                  90                  95

Tyr Tyr Tyr Tyr Tyr Gly Met Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His
                165

<210> SEQ ID NO 28
<211> LENGTH: 10
<212> TYPE: PRT
<213> ORGANISM: Homo sapiens

<400> SEQUENCE: 28

Gly Phe Thr Phe Ser Ser Tyr Gly Met His
 1               5                  10

<210> SEQ ID NO 29
<211> LENGTH: 15
<212> TYPE: PRT
```

```
<213> ORGANISM: Homo sapiens

<400> SEQUENCE: 29

Val Ile Trp Tyr Asp Gly Ser Asn Lys Tyr Tyr Ala Asp Ser Val
1               5                   10                  15

<210> SEQ ID NO 30
<211> LENGTH: 16
<212> TYPE: PRT
<213> ORGANISM: Homo sapiens

<400> SEQUENCE: 30

Asp Pro Arg Gly Ala Thr Leu Tyr Tyr Tyr Tyr Tyr Gly Met Asp Val
1               5                   10                  15

<210> SEQ ID NO 31
<211> LENGTH: 11
<212> TYPE: PRT
<213> ORGANISM: Homo sapiens

<400> SEQUENCE: 31

Arg Ala Ser Gln Ser Ile Asn Ser Tyr Leu Asp
1               5                   10

<210> SEQ ID NO 32
<211> LENGTH: 7
<212> TYPE: PRT
<213> ORGANISM: Homo sapiens

<400> SEQUENCE: 32

Ala Ala Ser Ser Leu Gln Ser
1               5

<210> SEQ ID NO 33
<211> LENGTH: 9
<212> TYPE: PRT
<213> ORGANISM: Homo sapiens

<400> SEQUENCE: 33

Gln Gln Tyr Tyr Ser Thr Pro Phe Thr
1               5

<210> SEQ ID NO 34
<211> LENGTH: 5
<212> TYPE: PRT
<213> ORGANISM: Artificial Sequence
<220> FEATURE:
<223> OTHER INFORMATION: Peptide linker
<220> FEATURE:
<221> NAME/KEY: misc_feature
<222> LOCATION: (5)..(5)
<223> OTHER INFORMATION: Xaa is any of Ala, Gly, Leu, Ile, Ser and Val

<400> SEQUENCE: 34

Gly Gly Gly Gly Xaa
1               5

<210> SEQ ID NO 35
<211> LENGTH: 5
<212> TYPE: PRT
<213> ORGANISM: Artificial Sequence
<220> FEATURE:
<223> OTHER INFORMATION: Peptide linker

<400> SEQUENCE: 35

Gly Gly Gly Gly Gly
```

```
1               5

<210> SEQ ID NO 36
<211> LENGTH: 5
<212> TYPE: PRT
<213> ORGANISM: Artificial Sequence
<220> FEATURE:
<223> OTHER INFORMATION: Peptide linker

<400> SEQUENCE: 36

Gly Gly Gly Gly Ala
1               5

<210> SEQ ID NO 37
<211> LENGTH: 7
<212> TYPE: PRT
<213> ORGANISM: Artificial Sequence
<220> FEATURE:
<223> OTHER INFORMATION: Peptide linker

<400> SEQUENCE: 37

Gly Gly Gly Ser Gly Gly Ser
1               5
```

CD40L-FC FUSION POLYPEPTIDES AND METHODS OF USE THEREOF

CROSS-REFERENCE TO RELATED APPLICATIONS

This patent application claims the benefit of U.S. Provisional Patent Application No. 62/336,129, filed May 13, 2016, which is incorporated by reference herein in its entirety.

REFERENCE TO SEQUENCE LISTING

This application incorporates by reference a Sequence Listing submitted with this application as a text filed entitled "CD40E-100-US-SeqListing.txt" created on May 11, 2017, and having a size of 41,546 bytes.

BACKGROUND OF THE INVENTION

Cancer continues to be a major global health burden. Despite progress in the treatment of cancer, there continues to be an unmet medical need for more effective and less toxic therapies, especially for those patients with advanced disease or cancers that are resistant to existing therapeutics.

The role of the immune system, in particular T cell-mediated cytotoxicity, in tumor control is well recognized. There is mounting evidence that T cells control tumor growth and survival in cancer patients, both in early and late stages of the disease. However, tumor-specific T-cell responses are difficult to mount and sustain in cancer patients.

T cell pathways receiving significant attention to date include signaling through cytotoxic T lymphocyte antigen-4 (CTLA-4, CD152) and programmed death ligand 1 (PD-L1, also known as B7-H1 or CD274). Recently however, CD40 ligand (CD40L) has generated interest as a mediator for tumor control.

CD40L is a member of the TNF family of molecules which is primarily expressed on activated T cells (including Th0, Th1, and Th2 subtypes), and forms homotrimers similar to other members of this family. Further, CD40L has also been found expressed on Mast cells, and activated basophils and eosinophils. CD40L binds to its receptor CD40 on antigen-presenting cells (APC), which leads to many effects depending on the target cell type. In general, CD40L plays the role of a costimulatory molecule and induces activation in APC in association with T cell receptor stimulation by MHC molecules on the APC.

Despite the significant progress made over the past decade in developing strategies for combatting cancer and other diseases, patients with advanced, refractory and metastatic disease have limited clinical options. Chemotherapy, irradiation, and high dose chemotherapy have become dose limiting. There remains a substantial unmet need for new less-toxic methods and therapeutics that have better therapeutic efficacy, longer clinical benefit, and improved safety profiles, particularly for those patients with advanced disease or cancers that are resistant to existing therapeutics.

SUMMARY OF THE INVENTION

In one aspect, the invention provides a fusion protein (e.g., a CD40L-Fc fusion protein) including a single chain fusion of three CD40 ligand (CD40L) subunits, or fragments thereof, (scCD40L) covalently linked to one another via peptide linkers; and an Fc monomer, where the scCD40L is covalently linked to the Fc monomer via a peptide linker.

In another aspect, the invention provides a dimer of two fusion proteins (e.g., a CD40L-Fc fusion protein), each fusion protein including a single chain fusion of three CD40 ligand (CD40L) subunits, or fragments thereof, (scCD40L) covalently linked to one another via peptide linkers; and an Fc monomer, where the scCD40L is covalently linked to the Fc monomer via a peptide linker, and wherein the dimer is formed via interaction of the Fc monomers.

In a specific aspect, the invention provides a fusion protein containing a single chain fusion including, from N-terminus to C-terminus, a first CD40L subunit having the amino acid sequence:

```
                                         (SEQ ID NO: 1)
NPQIAAHVISEASSKTTSVLQWAEKGYYTMSNNLVTLENGKQLTVKRQGL

YYIYAQVTFCSNREASSQAPFIASLWLKSPGRFERILLRAANTHSSAKPC

GQQSIHLGGVFELQPGASVFVNVTDPSQVSHGTGFTSFGLLKL
``` covalently linked to a first peptide linker having the amino acid sequence:

```
                                         (SEQ ID NO: 2)
                    GGGGSGGGS
``` covalently linked to a second CD40L subunit having the amino acid sequence:

```
                                         (SEQ ID NO: 3)
QIAAHVISEASSKTTSVLQWAEKGYYTMSNNLVTLENGKQLTVKRQGLYY

IYAQVTFCSNREASSQAPFIASLWLKSPGRFERILLRAANTHSSAKPCGQ

QSIHLGGVFELQPGASVFVNVTDPSQVSHGTGFTSFGLLKL
``` covalently linked to a second peptide linker having the amino acid sequence:

```
                                         (SEQ ID NO: 2)
                    GGGGSGGGS
``` covalently linked to a third CD40L subunit having the amino acid sequence:

```
                                         (SEQ ID NO: 3)
QIAAHVISEASSKTTSVLQWAEKGYYTMSNNLVTLENGKQLTVKRQGLYY

IYAQVTFCSNREASSQAPFIASLWLKSPGRFERILLRAANTHSSAKPCGQ

QSIHLGGVFELQPGASVFVNVTDPSQVSHGTGFTSFGLLKL
``` covalently linked to a third peptide linker having the amino acid sequence:

```
                                         (SEQ ID NO: 4)
                  GGGGSGGGSGGGGS
``` covalently linked to an Fc polypeptide.

In another aspect, the invention provides a method of activating a CD40 polypeptide, involving contacting the CD40 polypeptide with an isolated fusion protein according to any aspect delineated herein (e.g., a CD40L-Fc fusion protein).

In another aspect, the invention provides a method of enhancing an anti-tumor immune response in a subject involving administering to the subject an isolated fusion protein according to any aspect delineated herein (e.g., a CD40L-Fc fusion protein).

In another aspect, the invention provides a method of treating a subject having cancer involving administering to the subject an isolated fusion protein according to any aspect delineated herein (e.g., a CD40L-Fc fusion protein), and optionally one or more immune checkpoint inhibitors In another aspect, the invention provides a polynucleotide containing a nucleic acid molecule encoding the fusion protein according to any aspect delineated herein (e.g., a CD40L-Fc fusion protein).

In a related aspect, the invention provides a vector containing the polynucleotide according to any aspect delineated herein.

In another related aspect, the invention provides a host cell containing the vector according to any aspect delineated herein, including a host cell that expresses the isolated fusion protein according to any aspect delineated herein (e.g., a CD40L-Fc fusion protein).

In another aspect, the invention provides a method of making the fusion protein according to any aspect delineated herein (e.g., a CD40L-Fc fusion protein), involving culturing the host cell according to any aspect delineated herein; and isolating the fusion protein.

In another aspect, the invention provides a kit containing an isolated fusion protein (e.g., a CD40L-Fc fusion protein), polynucleotide, the vector, or the host cell of any aspect delineated herein.

In various embodiments of any aspect delineated herein, the fusion protein (e.g., CD40L-Fc fusion protein) binds and activates CD40 (e.g., a CD40 agonist). In various embodiments, the scCD40L folds into a CD40L homotrimer. In various embodiments, the isolated fusion protein (e.g., CD40L-Fc fusion protein) is a dimer. In various embodiments, the ratio of the CD40L subunits to the Fc monomer is 3:1. In various embodiments, the isolated fusion protein has less than about 10% aggregation for at least 3 days at about 21° C. or more. In various embodiments, the isolated fusion protein has less than about 1% aggregation for at least 7 days or more at about 21° C.

In certain embodiments, the isolated fusion protein has less than about 10% aggregation for at least 3 days or more at about 45° C.

In various embodiments of any aspect delineated herein, the CD40L-Fc fusion protein or CD40L subunit includes an amino acid sequence having at least about 85% amino acid sequence identity to (SEQ ID NO: 3)
QIAAHVISEASSKTTSVLQWAEKGYYTMSNNLVTLENGKQLTVKRQGLYY

IYAQVTFCSNREASSQAPFIASLWLKSPGRFERILLRAANTHSSAKPCGQ

QSIHLGGVFELQPGASVFVNVTDPSQVSHGTGFTSFGLLKL.

In various embodiments of any aspect delineated herein, one or more CD40L subunits has a Trp residue at position 74 (e.g., corresponding to a C→W substitution at position 194 of full-length membrane bound CD40L). In various embodiments of any aspect delineated herein, one or more CD40L subunits has a human CD40L sequence.

In various embodiments of any aspect delineated herein, the scCD40L is linked to the N-terminus or C-terminus of the Fc monomer. In certain embodiments, the Fc monomer contains a hinge region. In various embodiments of any aspect delineated herein, the Fc monomer comprises a human Fc sequence (e.g., an IgG4 amino acid sequence).

In various embodiments of any aspect delineated herein, the peptide linkers covalently linking the CD40L subunits, or fragments thereof, contain about 9 to about 20 amino acids.

In certain embodiments, the peptide linkers covalently linking the CD40L subunits, or fragments thereof, contain about 9 to about 15 amino acids. In particular embodiments, the peptide linkers covalently linking the CD40L subunits, or fragments thereof, contain 9 amino acids.

In various embodiments of any aspect delineated herein, the peptide linkers contain one or more glycine (Gly) or serine (Ser) amino acid residues. In various embodiments, the linker between CD40L subunits is $(Gly_4Ser)_n$ (SEQ ID NO: 5), where n is a positive integer selected from 2, 3, and 4; $(Gly_3Ser)_n$ (SEQ ID NO: 6), where n is selected from 3, 4, and 5; $Gly(Gly_3Ser)_n$ (SEQ ID NO: 7), where n is selected from 2, 3, and 4; or $Gly(Gly_2Ser)_n$ (SEQ ID NO: 8), where n is selected from 3, 4, 5, and 6. In particular embodiments, the linker is GGGGSGGGGSGGGGS (SEQ ID NO: 4) or GGGGSGGGS (SEQ ID NO: 2).

In various embodiments of any aspect delineated herein, the fusion protein (e.g., CD40L-Fc fusion protein) contains the amino acid sequence:

NPQIAAHVISEASSKTTSVLQWAEKGYYTMSNNLVTLENGKQLTVKRQGL

YYIYAQVTFCSNREASSQAPFIASLWLKSPGRFERILLRAANTHSSAKPC

GQQSIHLGGVFELQPGASVFVNVTDPSQVSHGTGFTSFGLLKLGGGGSGG

GSQIAAHVISEASSKTTSVLQWAEKGYYTMSNNLVTLENGKQLTVKRQGL

YYIYAQVTFCSNREASSQAPFIASLWLKSPGRFERILLRAANTHSSAKPC

GQQSIHLGGVFELQPGASVFVNVTDPSQVSHGTGFTSFGLLKLGGGGSGG

GSQIAAHVISEASSKTTSVLQWAEKGYYTMSNNLVTLENGKQLTVKRQGL

YYIYAQVTFCSNREASSQAPFIASLWLKSPGRFERILLRAANTHSSAKPC

GQQSIHLGGVFELQPGASVFVNVTDPSQVSHGTGFTSFGLLKLGGGGSGG

GGSGGGGSESKYGPPCPPCPAPEFLGGPSVFLFPPKPKDTLMISRTPEVT

CVVVDVSQEDPEVQFNWYVDGVEVHNAKTKPREEQFNSTYRVVSVLTVLH

QDWLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYSRL

TVDKSRWQEGNVFSCSVMHEALHNHYTQKSLSLSLGK; (SEQ ID NO:

9; scCD40L-IgG4P-FP6; MEDI5083)

NPQIAAHVISEASSKTTSVLQWAEKGYYTMSNNLVTLENGKQLTVKRQGL

YYIYAQVTFCSNREASSQAPFIASLWLKSPGRFERILLRAANTHSSAKPC

GQQSIHLGGVFELQPGASVFVNVTDPSQVSHGTGFTSFGLLKLGGGGSGG

GGSGGGGSQIAAHVISEASSKTTSVLQWAEKGYYTMSNNLVTLENGKQLT

VKRQGLYYIYAQVTFCSNREASSQAPFIASLWLKSPGRFERILLRAANTH

SSAKPCGQQSIHLGGVFELQPGASVFVNVTDPSQVSHGTGFTSFGLLKLG

GGGSGGGSGGGGSQIAAHVISEASSKTTSVLQWAEKGYYTMSNNLVTLE

NGKQLTVKRQGLYYIYAQVTFCSNREASSQAPFIASLWLKSPGRFERILL

RAANTHSSAKPCGQQSIHLGGVFELQPGASVFVNVTDPSQVSHGTGFTSF

```
-continued
GLLKLGGGGSGGGGSGGGGSESKYGPPCPPCPAPEFLGGPSVFLFPPKPK

DTLMISRTPEVTCVVVDVSQEDPEVQFNWYVDGVEVHNAKTKPREEQFNS

TYRVVSVLTVLHQDWLNGKEYKCKVSNKGLPSSIEKTISKAKGQPREPQV

YTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK (SEQ ID NO: 10; scCD40L-IgG4P-FP7);
or

DPQIAAHVVSEANSNAASVLQWAKKGYYTMKSNLVMLENGKQLTVKREGL

YYVYTQVTFCSNREPSSQRPFIVGLWLKPSSGSERILLKAANTHSSSQLC

EQQSVHLGGVFELQAGASVFVNVTEASQVIHRVGFSSFGLLKLGGGSGGS

QIAAHVVSEANSNAASVLQWAKKGYYTMKSNLVMLENGKQLTVKREGLYY

VYTQVTFCSNREPSSQRPFIVGLWLKPSSGSERILLKAANTHSSSQLCEQ

QSVHLGGVFELQAGASVFVNVTEASQVIHRVGFSSFGLLKLGGGSGGSQI

AAHVVSEANSNAASVLQWAKKGYYTMKSNLVMLENGKQLTVKREGLYYVY

TQVTFCSNREPSSQRPFIVGLWLKPSSGSERILLKAANTHSSSQLCEQQS

VHLGGVFELQAGASVFVNVTEASQVIHRVGFSSFGLLKLGGGSGGGGSG

GGGSVPRDCGCKPCICTVPEVSSVFIFPPKPKDVLTITLTPKVTCVVVAI

SKDDPEVQFSWFVDDVEVHTAQTQPREEQFNSTFRSVSELPIMHQDWLNG

KEFKCRVNSAAFPAPIEKTISKTKGRPKAPQVYTIPPPKEQMAKDKVSLT

CMITDFFPEDITVEWQWNGQPAENYKNTQPIMDTDGSYFVYSKLNVQKSN

WEAGNTFTCSVLHEGLHNHHTEKSLSHSPGK (SEQ ID NO: 11; the murine surrogate FP5-like, mouse IgG1 D265A Fc).
```

In various embodiments of any aspect delineated herein, the fusion protein (e.g., CD40L-Fc fusion protein) binds up to six CD40 polypeptides. In various embodiments, the CD40 polypeptide is on a cell. In various embodiments, the cell expresses a CD40 polypeptide. In certain embodiments, the cell is an antigen presenting cell, macrophage, B-cell, or dendritic cell. In various embodiments, the cell is in a subject. In certain embodiments, the subject has cancer.

In various embodiments of any aspect delineated herein, the one or more immune checkpoint inhibitors comprises a PD-L1 or CTLA-4 antagonist. In various embodiments, the PD-L1 or CTLA-4 antagonist is an antibody. In certain embodiments, the anti-PD-L1 antibody is durvalumab. In certain embodiments, the anti-CTLA-4 antibody is tremelimumab. In various embodiments of any aspect delineated herein, an immune response and/or an anti-cancer response is enhanced. In various embodiments of any aspect delineated herein, immunosuppression of a tumor microenvironment is reduced.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "anti-tumor activity" is meant any biological activity that reduces or stabilizes the proliferation or survival of a tumor cell. In one embodiment, the anti-tumor activity is an anti-tumor immune response.

By "immunomodulatory agent" is meant an agent that enhances an immune response (e.g., anti-tumor immune response). Exemplary immunomodulatory agents of the invention include antibodies, such as an anti-CTLA-4 antibody, an anti-PD-L1 antibody, and fragments thereof, as well as proteins, such as CD40L-Fc fusion protein, or fragments thereof.

By "CD40L polypeptide" is meant a polypeptide or fragment thereof having at least about 85% amino acid identity to NCBI Accession No. NP_000065 and having CD40 binding activity. The term "CD40L" refers both to the full length CD40L and to soluble fragments, e.g., extracellular domain forms of CD40L resulting from proteolysis, and to monomeric forms of CD40L as well as oligomeric forms, e.g., trimeric CD40L. Amino acid sequences of membrane-bound and soluble forms of human CD40L are shown below:

CD40L Sp|P29965|CD40L_HUMAN—Membrane Bound Form (SEQ ID NO: 12)

Cytoplasmic domain=1-20; Signal anchor type II membrane protein region=21-46; soluble form=113-261

```
MIETYNQTSPRSAATGLPISMKIFMYLLTVFLITQMIGSALFAVYLHRRL

DKIEDERNLHEDFVFMKTIQRCNTGERSLSLLNCEEIKSQFEGFVKDIML

NKEETKKENSFEMQKGDQNPQIAAHVISEASSKTTSVLQWAEKGYYTMSN

NLVTLENGKQLTVKRQGLYYIYAQVTFCSNREASSQAPFIASLCLKSPGR

FERILLRAANTHSSAKPCGQQSIHLGGVFELQPGASVFVNVTDPSQVSHG

TGFTSFGLLKL
```

CD40L—Soluble Form (SEQ ID NO: 13)

```
MQKGDQNPQIAAHVISEASSKTTSVLQWAEKGYYTMSNNLVTLENGKQLT

VKRQGLYYIYAQVTFCSNREASSQAPFIASLCLKSPGRFERILLRAANTH

SSAKPCGQQSIHLGGVFELQPGASVFVNVTDPSQVSHGTGFTSFGLLKL
```

By "CD40L nucleic acid molecule" is meant a polynucleotide encoding a CD40L polypeptide. An exemplary CD40L nucleic acid molecule sequence is provided at NCBI Accession No. NM_000074.

By "CD40 polypeptide" is meant a polypeptide or fragment thereof having at least about 85% amino acid identity to NCBI Accession No. NP_001241 and having CD40L binding activity. An exemplary CD40 amino acid sequence is provided below (SEQ ID NO: 14):

```
MVRLPLQCVLWGCLLTAVHPEPPTACREKQYLINSQCCSLCQPGQKLVSD

CTEFTETECLPCGESEFLDTWNRETHCHQHKYCDPNLGLRVQQKGTSETD

TICTCEEGWHCTSEACESCVLHRSCSPGFGVKQIATGVSDTICEPCPVGF

FSNVSSAFEKCHPWTSCETKDLVVQQAGTNKTDVVCGPQDRLRALVVIPI
```

IFGILFAILLVLVFIKKVAKKPTNKAPHPKQEPQEINFPDDLPGSNTAAP

VQETLHGCQPVTQEDGKESRISVQERQ

By "CD40 nucleic acid molecule" is meant a polynucleotide encoding a CD40 polypeptide. An exemplary CD40 nucleic acid molecule sequence is provided at NCBI Accession No. NM_001250.

By "PD-L1 polypeptide" is meant a polypeptide or fragment thereof having at least about 85% amino acid identity to NCBI Accession No. NP_001254635 and having PD-1 and CD80 binding activity. An exemplary PD-L1 amino acid sequence is provided below (SEQ ID NO: 15):

MRIFAVFIFMTYWHLLNAPYNKINQRILVVDPVTSEHELTCQAEGYPKAE

VIWTSSDHQVLSGKTTTTNSKREEKLFNVTSTLRINTTTNEIFYCTFRRL

DPEENHTAELVIPELPLAHPPNERTHLVILGAILLCLGVALTFIFRLRKG

RMMDVKKCGIQDTNSKKQSDTHLEET

By "PD-L1 nucleic acid molecule" is meant a polynucleotide encoding a PD-L1 polypeptide. An exemplary PD-L1 nucleic acid molecule sequence is provided at NCBI Accession No. NM_001267706.

By "anti-PD-L1 antibody" is meant an antibody that selectively binds a PD-L1 polypeptide. Exemplary anti-PD-L1 antibodies are described for example at US20130034559/ U.S. Pat. No. 8,779,108 and US20140356353, which is herein incorporated by reference. Durvalumab (MEDI4736) is an exemplary anti-PD-L1 antibody. Other anti-PD-L1 antibodies include BMS-936559 (Bristol-Myers Squibb) and MPDL3280A (Roche).

Durvalumab VL
(SEQ ID NO: 16)
EIVLTQSPGTLSLSPGERATLSCRASQRVSSSYLAWYQQKPGQAPRLLIY

DASSRATGIPDRFSGSGSGTDFTLTISRLEPEDFAVYYCQQYGSLPWTFG

QGTKVEIK

Durvalumab VH
(SEQ ID NO: 17)
EVQLVESGGGLVQPGGSLRLSCAASGFTFSRYWMSWVRQAPGKGLEWVAN

IKQDGSEKYYVDSVKGRFTISRDNAKNSLYLQMNSLRAEDTAVYYCAREG

GWFGELAFDYWGQGTLVTVSS

Durvalumab VH CDR1
(SEQ ID NO: 18)
GFTFSRYWMS

Durvalumab VH CDR2
(SEQ ID NO: 19)
NIKQDGSEKYYVDSVKG

Durvalumab VH CDR3
(SEQ ID NO: 20)
EGGWFGELAFDY

Durvalumab VL CDR1
(SEQ ID NO: 21)
RASQRVSSSYLA

Durvalumab VL CDR2
(SEQ ID NO: 22)
DASSRAT

Durvalumab VL CDR3
(SEQ ID NO: 23)
QQYGSLPWT

By "PD-1 polypeptide" is meant a polypeptide or fragment thereof having at least about 85% amino acid identity to NCBI Accession No. NP_005009 and having PD-L1 binding activity. An exemplary PD-1 amino acid sequence is provided below (SEQ ID NO: 24):

MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQFQTLVVGVVGGLLGSLVLLVWVLAVICSRAARGTI

GARRTGQPLKEDPSAVPVFSVDYGELDFQWREKTPEPPVPCVPEQTEYAT

IVFPSGMGTSSPARRGSADGPRSAQPLRPEDGHCSWPL

By "PD-1 nucleic acid molecule" is meant a polynucleotide encoding a PD-1 polypeptide. An exemplary PD-1 nucleic acid molecule sequence is provided at NCBI Accession No. NM_005018.

By "CTLA-4 polypeptide" is meant a polypeptide having at least 85% amino acid sequence identity to GenBank Accession No. AAL07473.1 or a fragment thereof having T cell inhibitory activity. An exemplary CTLA-4 amino acid sequence is provided below (SEQ ID NO: 25):

gi|15778586|gb|AAL07473.1|AF414120_1

CTLA-4 [Homo sapiens]

MACLGFQRHKAQLNLATRTWPCTLLFFLLFIPVFCKAMHVAQPAVVLASS

RGIASFVCEYASPGKATEVRVTVLRQADSQVTEVCAATYMMGNELTFLDD

SICTGTSSGNQVNLTIQGLRAMDTGLYICKVELMYPPPYYLGIGNGTQIY

VIDPEPCPDSDFLLWILAAVSSGLFFYSFLLTAVSLSKMLKKRSPLTTGV

YVKMPPTEPECEKQFQPYFIPIN

By "CTLA-4 nucleic acid molecule" is meant a polynucleotide encoding a CTLA-4 polypeptide. An exemplary CTLA-4 nucleic acid molecule is provided at GenBank Accession No. AF414120.1.

By "anti-CTLA-4 antibody" is meant an antibody that selectively binds a CTLA-4 polypeptide. Exemplary anti-CTLA-4 antibodies are described for example at U.S. Pat. Nos. 6,682,736; 7,109,003; 7,123,281; 7,411,057; 7,824,679; 8,143,379; 7,807,797; and 8,491,895 (Tremelimumab is 11.2.1, therein), which are herein incorporated by reference. Tremelimumab is an exemplary anti-CTLA-4 antibody. Tremelimumab sequences are provided below.

Tremelimumab U.S. Pat. No. 6,682,736
Tremelimumab VL
(SEQ ID NO: 26)
PSSLSASVGDRVTITCRASQSINSYLDWYQQKPGKAPKLLIYAASSLQSG

VPSRFSGSGSGTDFTLTISSLQPEDFATYYCQQYYSTPFTFGPGTKVEIK

RTVAAPSVFIFPPSDEQLKSGTASVVCLLNNFYPREAKV

-continued

Tremelimumab VH
(SEQ ID NO: 27)
GVVQPGRSLRLSCAASGFTFSSYGMHWVRQAPGKGLEWVAVIWYDGSNKY

YADSVKGRFTISRDNSKNTLYLQMNSLRAEDTAVYYCARDPRGATLYYYY

YGMDVWGQGTTVTVSSASTKGPSVFPLAPCSRSTSESTAALGCLVKDYFP

EPVTVSWNSGALTSGVH

Tremelimumab VH CDR1
(SEQ ID NO: 28)
GFTFSSYGMH

Tremelimumab VH CDR2
(SEQ ID NO: 29)
VIWYDGSNKYYADSV

Tremelimumab VH CDR3
(SEQ ID NO: 30)
DPRGATLYYYYGMDV

Tremelimumab VL CDR1
(SEQ ID NO: 31)
RASQSINSYLD

Tremelimumab VL CDR2
(SEQ ID NO: 32)
AASSLQS

Tremelimumab VL CDR3
(SEQ ID NO: 33)
QQYYSTPFT

The term "antibody," as used in this disclosure, refers to an immunoglobulin or a fragment or a derivative thereof, and encompasses any polypeptide comprising an antigen-binding site, regardless of whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also includes antibody fragments such as Fab, F(ab')2, Fv, scFv, Fd, dAb, and other antibody fragments that retain antigen-binding function, i.e., the ability to bind, for example, CTLA-4 or PD-L1, specifically. Typically, such fragments would comprise an antigen-binding domain.

The terms "antigen-binding domain," "antigen-binding fragment," and "binding fragment" refer to a part of an antibody molecule that comprises amino acids responsible for the specific binding between the antibody and the antigen. In instances, where an antigen is large, the antigen-binding domain may only bind to a part of the antigen. A portion of the antigen molecule that is responsible for specific interactions with the antigen-binding domain is referred to as "epitope" or "antigenic determinant." An antigen-binding domain typically comprises an antibody light chain variable region ($V_L$) and an antibody heavy chain variable region ($V_H$), however, it does not necessarily have to comprise both. For example, a so-called Fd antibody fragment consists only of a $V_H$ domain, but still retains some antigen-binding function of the intact antibody.

Binding fragments of an antibody are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a F(ab')2 fragment in which the two arms of the antibody molecule remain linked and comprise two-antigen binding sites. The F(ab')2 fragment has the ability to crosslink antigen. "Fv" when used herein refers to the minimum fragment of an antibody that retains both antigen-recognition and antigen-binding sites. "Fab" when used herein refers to a fragment of an antibody that comprises the constant domain of the light chain and the CHI domain of the heavy chain.

The term "mAb" refers to monoclonal antibody. Antibodies of the invention comprise without limitation whole native antibodies, bispecific antibodies; chimeric antibodies; Fab, Fab', single chain V region fragments (scFv), fusion polypeptides, and unconventional antibodies.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the terms "determining", "assessing", "assaying", "measuring" and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

As used herein, the term "Fc domain" domain refers to a portion of an antibody constant region. Traditionally, the term Fc domain refers to a protease (e.g., papain) cleavage product encompassing the paired CH2, CH3 and hinge regions of an antibody. In the context of this disclosure, the term Fc domain or Fc refers to any polypeptide (or nucleic acid encoding such a polypeptide), regardless of the means of production, that includes all or a portion of the CH2, CH3 and hinge regions of an immunoglobulin polypeptide.

By "fusion polypeptide" or "fusion protein", is meant a polypeptide comprising two or more different polypeptides or active fragments thereof that are not naturally present in the same polypeptide. In various embodiments, the two or more different polypeptides are operatively linked together covalently, e.g., chemically linked or fused in frame by a peptide bond or a peptide linker.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences (see e.g., Karlin et al., 1990, *Proc. Natl. Acad. Sci.*, 87:2264-2268, as modified in Karlin et al., 1993, *Proc. Natl. Acad. Sci.*, 90:5873-5877, and incorporated into the NBLAST and XBLAST programs (Altschul et al., 1991, *Nucleic Acids Res.*, 25:3389-3402). In certain embodiments, Gapped BLAST can be used as described in Altschul et al., 1997, *Nucleic Acids Res.* 25:3389-3402. BLAST-2, WU-BLAST-2 (Altschul et al., 1996, *Methods in Enzymology*, 266:460-480), ALIGN, ALIGN-2 (Genentech, South San Francisco, Calif.) or Megalign (DNASTAR).

The term "isolated" refers to a molecule that is substantially free of other elements present in its natural environment. For instance, an isolated protein is substantially free of cellular material or other proteins from the cell or tissue source from which it is derived. The term "isolated" also refers to preparations where the isolated protein is sufficiently pure to be administered as a pharmaceutical composition, or at least 70-80% (w/w) pure, more preferably, at least 80-90% (w/w) pure, even more preferably, 90-95% pure; and, most preferably, at least 95%, 96%, 97%, 98%, 99%, or 100% (w/w) pure.

By "reference" is meant a standard of comparison.

By "specifically binds" is meant an agent (e.g., CD40L) that recognizes and binds a molecule (e.g., CD40 polypeptide), but which does not substantially recognize and bind other molecules in a sample, for example, a biological sample. For example, two molecules that specifically bind form a complex that is relatively stable under physiologic conditions. Specific binding is characterized by a high affinity and a low to moderate capacity as distinguished from nonspecific binding which usually has a low affinity with a moderate to high capacity.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A," (alone) and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 17 is a series of graphs depicting the anti-tumor activity of mouse surrogate CD40L-FP in combination with α-CTLA-4 in a B16-F10 tumor model. Responses of individual mice are plotted on the graphs.

DETAILED DESCRIPTION OF THE INVENTION

Figure 1:
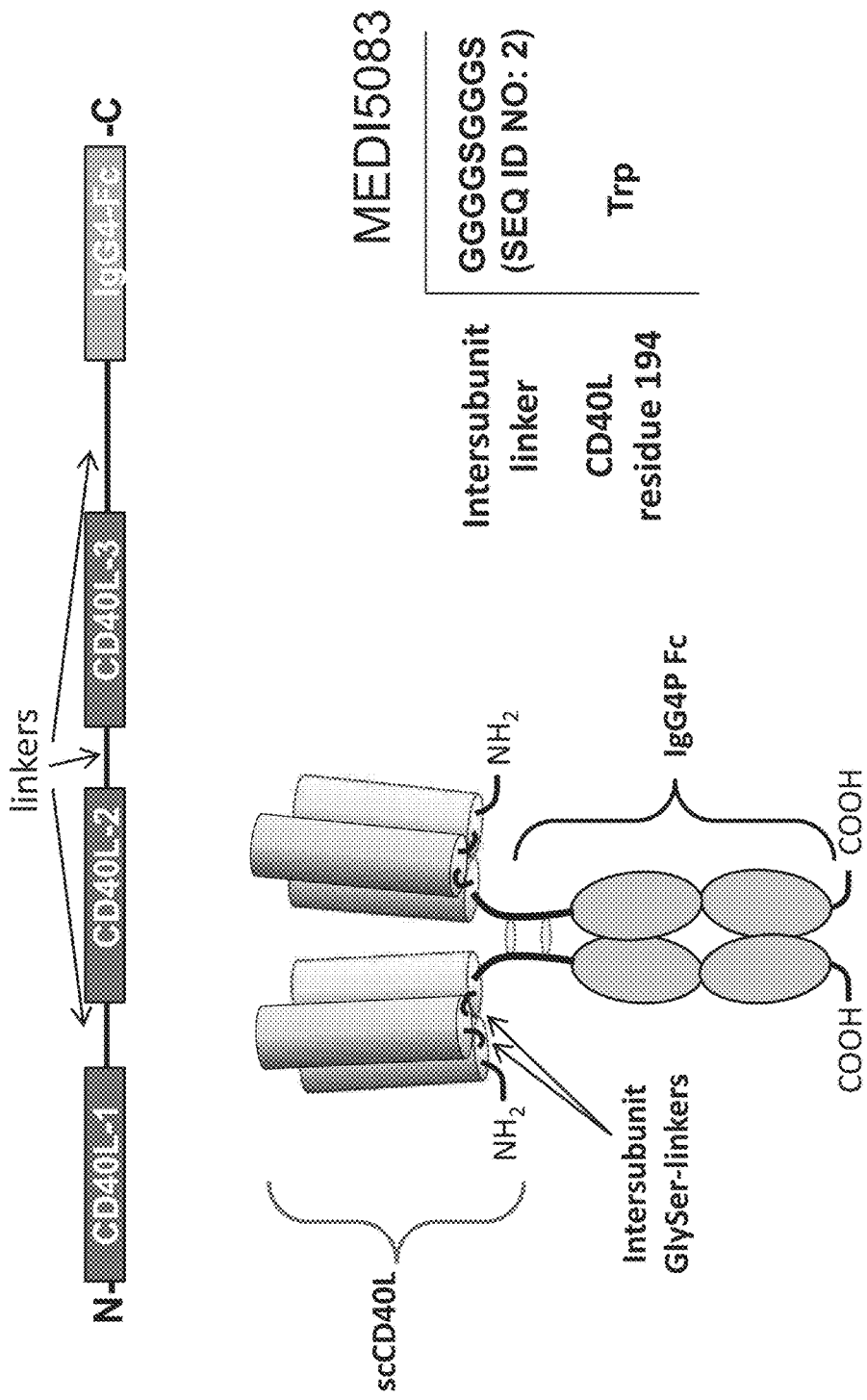
FIG. 1 depicts schematic representation of the CD40L-Fc fusion proteins of the invention comprising human amino acid sequences. As depicted, MEDI5083 CD40L-FP comprises a single chain fusion of 3×CD40L subunits+IgG4P Fc (148 kDa), 9-GlySer linker regions, and residue 194 (unpaired Cys) mutated for development. Intersubunit linker: SEQ ID NO: 2.

The invention features fusion proteins comprising three CD40 ligand (CD40L) subunits and an Fc polypeptide (CD40L-Fc). In one aspect, the CD40L-Fc fusion protein comprises a single chain fusion of three CD40 ligand (CD40L) subunits and an Fc monomer linked via peptide linkers. It has been found that peptide linkers having a length of 9 amino acids or more between the CD40L subunits retained stability and/or did not cause aggregation of such fusion proteins. This is in contrast to other TNF family ligands, which are prone to aggregation when linked via peptide linkers greater than 8 amino acids in length. Thus, the invention is based at least in part on these discoveries.

The present invention also features compositions and methods that are useful for treating cancer comprising a CD40L-Fc fusion protein (e.g., MEDI5083). In various embodiments, the CD40L-Fc fusion protein (e.g., MEDI5083) is administered in combination with an immune checkpoint inhibitor, including one or more of an anti-CTLA-4 antibody and/or an anti-PD-L1 antibody. As reported herein below, treatment with these agents reduced tumor volume and/or delayed tumor growth in a mouse tumor model.

CD40L-Fc Fusion Proteins

The invention provides CD40L-Fc fusion proteins comprising a single chain fusion of three CD40 ligand (CD40L) subunits, or fragments thereof, (scCD40L) covalently linked to one another via peptide linkers and an Fc monomer which is covalently linked to the scCD40L via a peptide linker. In various aspects, the three CD40L subunits of the fusion protein are arranged such that the peptide linker connects the C-terminus of a CD40L subunit to the N-terminus of another CD40L subunit. Thus, the fusion protein of the invention comprises a portion, from N-terminus to C-terminus, that comprises the C-terminus of a first CD40L subunit connected to the N-terminus of a second CD40L subunit via a peptide linker and the C-terminus of the second CD40L subunit connected to the N-terminus of a third CD40L subunit. In various embodiments, the single chain fusion of the three CD40L subunits is connected to the Fc polypeptide via a peptide linker at the C-terminus or N-terminus. That is, the N-terminus of the N-terminus of the Fc polypeptide is connected to the C-terminus of the third CD40L subunit of the single chain fusion of the three CD40L subunits or the C-terminus of the Fc polypeptide is connected to the N-terminus of the first CD40L subunit of the single chain fusion of the three CD40L subunits.

CD40L (also known as CD154, CD40 ligand, gp39 or TBAM) is a 33 kDa, Type II membrane glycoprotein (Swiss-ProtAcc-No P29965). Additionally, shorter 18 kDa CD40L soluble forms exist, (also known as sCD40L or soluble CD40L). These soluble forms of CD40L are generated by proteolytic processing of the membrane bound protein, but the cellular activity of the soluble species is weak in the absence of higher order oligomerization (e.g., trimerization). CD40L binds and activates CD40. In various embodiments, a CD40L-Fc fusion protein comprises a region of three CD40L subunit that self-assembles into a CD40L trimer. In one aspect, the CD40L-Fc fusion protein assembles into a multimeric form, capable of binding to CD40 and stimulating at least one CD40 mediated activity. In various embodiments, a CD40L subunit has an amino acid sequence from human CD40L. Additional CD40L homologs include those from mouse, chicken, Rhesus, cynomolgus, rat, and rabbit. Combinations of CD40L subunits in the CD40L-Fc fusion protein can be homomeric or heteromeric. In some embodiments, the amino acid sequences of all CD40L subunits in the CD40L-Fc fusion protein are identical. In other embodiments, the amino acid sequences of at least two of the CD40L subunits in the CD40L-Fc fusion protein are different.

The CD40L-Fc fusion protein of the invention comprises a CD40L trimer fused to a domain or fragment of an antibody (e.g., an IgG), including, but not limited to, an Fc domain. In a specific embodiment, the CD40L-Fc fusion protein of the invention comprises a CD40L trimer fused to an Fc domain. In some embodiments, the CD40L-Fc fusion protein of the invention dimerizes via the Fc domain. In certain embodiments, the Fc domain has an amino acid sequence of an IgG4P Fc domain. IgG4P Fc is an IgG4 fragment crystallizable gamma (Fcγ) domain containing a serine to proline substitution in the hinge region at position 228 (according to EU numbering). The serine to proline substitution in IgG4P Fc promotes stability, confers complete inter-heavy chain disulfide bond formation, and/or prevents recombination of the dimer via "half-antibody exchange" (Nirula et al. (2011) *Curr. Opin. Rheumatol.* 23(1):119-124; Aalberse et al. (2009) Clin. Exp. Allergy 39(4):469-477). In particular embodiments, the amino acid sequence of the IgG4P Fc domain is a human sequence. It is known in the art that variants of the Fc region (e.g., amino acid substitutions and/or additions and/or deletions) enhance or diminish effector function of the antibody. Thus, in certain embodiments, the CD40L-Fc fusion proteins of the invention comprises an Fc domain with one or more alterations made in the Fc region to change functional properties of the CD40L-Fc fusion protein. In certain embodiments, the CD40L-Fc fusion proteins of the invention comprise an Fc domain with one or more alterations made in the Fc region in order reduce or eliminate at least one FcγR-mediated effector function.

In various aspects, the present disclosure provides a CD40L-Fc fusion protein with an IgG4 Fc that comprises at least one modification at one or more positions selected from the group consisting of 228 and 235 as numbered by the EU index as set forth in Kabat. In still another specific aspect, the Fc region is an IgG4 Fc region and variant amino acids are one or more of 228P, 235E and 235Y as numbered by the EU index as set forth in Kabat.

The CD40L subunits and Fc polypeptide in the CD40L-Fc fusion proteins of the invention are connected by polypeptide linkers, wherein each linker is fused to at least two polypeptides or subunits. Combinations of linkers in the CD40L-Fc fusion protein can be homomeric or heteromeric. In some embodiments, the amino acid sequences of all peptide linkers present in a CD40L-Fc fusion protein of the invention are identical. In other embodiments, the amino acid sequences of at least two of the peptide linkers present in a CD40L-Fc fusion protein of the invention are different. The linker polypeptide should have a length, which is adequate to link two or more monomer subunits in such a way that they assume the correct conformation relative to one another so that they retain the desired activity. The use of naturally occurring as well as artificial peptide linkers to connect polypeptides into novel linked fusion polypeptides is well known in the literature. Accordingly, the linkers fusing two or more monomer subunits are natural linkers, artificial linkers, or combinations thereof.

As described herein, it has been found that peptide linkers having a length of 9 amino acids or more between the CD40L subunits retained stability and/or did not cause aggregation of such fusion proteins. Thus, the polypeptide linker comprises 9 to about 20 amino acids residues, 9 to about 15 amino acid residues, or 9 amino acid residues. The amino acid residues selected for inclusion in the polypeptide linker should exhibit properties that do not interfere significantly with the activity or function of the CD40L-Fc fusion protein of the invention. Thus, a polypeptide linker should on the whole not exhibit a charge which would be inconsistent with the activity or function of the CD40L-Fc fusion protein of the invention, or interfere with internal folding, or form bonds or other interactions with amino acid residues in one or more of the monomer subunits which would seriously impede the binding In various embodiments, a polypeptide linker possesses conformational flexibility. Suitable flexible linkers include those having a combination of Gly and Ser residues, where the ratio of Gly to Ser is ≥1. In some embodiments, a polypeptide linker sequence comprises a $(G-G-G-G-X)_n$ (SEQ ID NO: 34) amino acid sequence where X is Alanine (A), Serine (S), Glycine (G), Isoleucine (I), Leucine (L) or Valine (V) and n is a positive integer. In certain embodiments, a polypeptide linker sequence comprises a $(G-G-G-S)_n$ (SEQ ID NO: 6), $(G-G-G-G-S)_n$ (SEQ ID NO: 5), $G(G-G-G-S)_n$ (SEQ ID NO: 7), $(G-G-G-G-G)_n$ (SEQ ID NO: 35), or $(G-G-G-G-A)_n$ (SEQ ID NO: 36), amino acid sequence where n is a positive integer. In some embodiments, a polypeptide linker is an inherently unstructured natural or artificial polypeptide (see, e.g., Schellenberger et al., Nature Biotechnol. 27:1186-1190, 2009; see also, Sickmeier et al., Nucleic Acids Res. 35:D786-93, 2007).

In certain embodiments, the linker between CD40L subunits is $(Gly_4Ser)_n$ (SEQ ID NO: 5), where n is a positive integer selected from 2, 3, and 4; $(Gly_3Ser)_n$ (SEQ ID NO: 6), where n is selected from 3, 4, and 5; $Gly(Gly_3Ser)_n$ (SEQ ID NO: 7), where n is selected from 2, 3, and 4; or $Gly(Gly_2Ser)_n$ (SEQ ID NO: 8), where n is selected from 3, 4, 5, and 6. In particular embodiments, the linker is GGGGSGGGGSGGGGS (SEQ ID NO: 4) or GGGGSGGGS (SEQ ID NO: 2).

In certain embodiments, the CD40L Fc fusion protein contains a single chain fusion including, from N-terminus to C-terminus, a first CD40L subunit having the amino acid sequence:

```
                                          (SEQ ID NO: 1)
NPQIAAHVISEASSKTTSVLQWAEKGYYTMSNNLVTLENGKQLTVKRQGL

YYIYAQVTFCSNREASSQAPFIASLWLKSPGRFERILLRAANTHSSAKPC

GQQSIHLGGVFELQPGASVFVNVTDPSQVSHGTGFTSFGLLKL
``` covalently linked to a first peptide linker having the amino acid sequence:

```
                                          (SEQ ID NO: 2)
              GGGGSGGGS
``` covalently linked to a second CD40L subunit having the amino acid sequence:

```
                                          (SEQ ID NO: 3)
QIAAHVISEASSKTTSVLQWAEKGYYTMSNNLVTLENGKQLTVKRQGLYY

IYAQVTFCSNREASSQAPFIASLWLKSPGRFERILLRAANTHSSAKPCGQ

QSIHLGGVFELQPGASVFVNVTDPSQVSHGTGFTSFGLLKL
``` covalently linked to a second peptide linker having the amino acid sequence:

```
                                          (SEQ ID NO: 2)
              GGGGSGGGS
``` covalently linked to a third CD40L subunit having the amino acid sequence:

(SEQ ID NO: 3)
QIAAHVISEASSKTTSVLQWAEKGYYTMSNNLVTLENGKQLTVKRQGLYY

IYAQVTFCSNREASSQAPFIASLWLKSPGRFERILLRAANTHSSAKPCGQ

QSIHLGGVFELQPGASVFVNVTDPSQVSHGTGFTSFGLLKL covalently linked to a third peptide linker having the amino acid sequence:

(SEQ ID NO: 4)
GGGGSGGGGSGGGGS covalently linked to an Fc polypeptide.

In particular embodiments, CD40L Fc fusion protein comprises or consists of one of the following amino acid sequences:

(SEQ ID NO: 9; scCD40L-IgG4P-FP6; MEDI5083)
NPQIAAHVISEASSKTTSVLQWAEKGYYTMSNNLVTLENGKQLTVKRQGL

YYIYAQVTFCSNREASSQAPFIASLWLKSPGRFERILLRAANTHSSAKPC

GQQSIHLGGVFELQPGASVFVNVTDPSQVSHGTGFTSFGLLKLGGGGSGG

GSGIAAHVISEASSKTTSVLQWAEKGYYTMSNNLVTLENGKQLTVKRQGL

YYIYAQVTFCSNREASSQAPFIASLWLKSPGRFERILLRAANTHSSAKPC

GQQSIHLGGVFELQPGASVFVNVTDPSQVSHGTGFTSFGLLKLGGGGSGG

GSQIAAHVISEASSKTTSVLQWAEKGYYTMSNNLVTLENGKQLTVKRQGL

YYIYAQVTFCSNREASSQAPFIASLWLKSPGRFERILLRAANTHSSAKPC

GQQSIHLGGVFELQPGASVFVNVTDPSQVSHGTGFTSFGLLKLGGGGSGG

GGSGGGGSESKYGPPCPPCPAPEFLGGPSVFLFPPKPKDTLMISRTPEVT

CVVVDVSQEDPEVQFNWYVDGVEVHNAKTKPREEQFNSTYRVVSVLTVLH

QDWLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYSRL

TVDKSRWQEGNVFSCSVMHEALHNHYTQKSLSLSLGK;;

(SEQ ID NO: 10; scCD40L-IgG4P-FP7)
NPQIAAHVISEASSKTTSVLQWAEKGYYTMSNNLVTLENGKQLTVKRQGL

YYIYAQVTFCSNREASSQAPFIASLWLKSPGRFERILLRAANTHSSAKPC

GQQSIHLGGVFELQPGASVFVNVTDPSQVSHGTGFTSFGLLKLGGGGSGG

GGSGGGGSQIAAHVISEASSKTTSVLQWAEKGYYTMSNNLVTLENGKQLT

VKRQGLYYIYAQVTFCSNREASSQAPFIASLWLKSPGRFERILLRAANTH

SSAKPCGQQSIHLGGVFELQPGASVFVNVTDPSQVSHGTGFTSFGLLKLG

GGGSGGGGSGGGGSQIAAHVISEASSKTTSVLQWAEKGYYTMSNNLVTLE

NGKQLTVKRQGLYYIYAQVTFCSNREASSQAPFIASLWLKSPGRFERILL

RAANTHSSAKPCGQQSIHLGGVFELQPGASVFVNVTDPSQVSHGTGFTSF

GLLKLGGGGSGGGGSGGGGSESKYGPPCPPCPAPEFLGGPSVFLFPPKPK

DTLMISRTPEVTCVVVDVSQEDPEVQFNWYVDGVEVHNAKTKPREEQFNS

TYRVVSVLTVLHQDWLNGKEYKCKVSNKGLPSSIEKTISKAKGQPREPQV

YTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLG

K;;
or

DPQIAAHVVSEANSNAASVLQWAKKGYYTMKSNLVMLENGKQLTVKREGL

YYVYTQVTFCSNREPSSQRPFIVGLWLKPSSGSERILLKAANTHSSSQLC

EQQSVHLGGVFELQAGASVFVNVTEASQVIHRVGFSSFGLLKLGGGSGGS

QIAAHVVSEANSNAASVLQWAKKGYYTMKSNLVMLENGKQLTVKREGLYY

VYTQVTFCSNREPSSQRPFIVGLWLKPSSGSERILLKAANTHSSSQLCEQ

QSVHLGGVFELQAGASVFVNVTEASQVIHRVGFSSFGLLKLGGGSGGSQI

AAHVVSEANSNAASVLQWAKKGYYTMKSNLVMLENGKQLTVKREGLYYVY

TQVTFCSNREPSSQRPFIVGLWLKPSSGSERILLKAANTHSSSQLCEQQS

VHLGGVFELQAGASVFVNVTEASQVIHRVGFSSFGLLKLGGGGSGGGGSG

GGGSVPRDCGCKPCICTVPEVSSVFIFPPKPKDVLTITLTPKVTCVVVAI

SKDDPEVQFSWFVDDVEVHTAQTQPREEQFNSTFRSVSELPIMHQDWLNG

KEFKCRVNSAAFPAPIEKTISKTKGRPKAPQVYTIPPPKEQMAKDKVSLT

CMITDFFPEDITVEWQWNGQPAENYKNTQPIMDTDGSYFVYSKLNVQKSN

WEAGNTFTCSVLHEGLHNHHTEKSLSHSPGK (SEQ ID NO: 11;

Murine surrogate FP5-like, mouse IgG1 D265A Fc).

Anti-Tumor Therapy

Provided herein are methods for treating cancer, comprising administration of CD40L-Fc fusion protein (e.g., MEDI5083) alone or in combination with an immune checkpoint inhibitor (e.g., an anti-CTLA4 antibody, anti-PD-L1 antibody, and/or anti-PD-1 antibody, or antigen-binding fragments thereof). As shown herein, administration of CD40L-Fc fusion protein (e.g., MEDI5083) alone or in combination with anti-CTLA4 antibody, anti-PD-L1 antibody, and/or anti-PD-1 antibody resulted in a reduction in tumor volume in a mouse tumor model. In certain aspects, a patient presenting with a solid tumor is administered CD40L-Fc fusion protein (e.g., MEDI5083) alone or in combination with anti-CTLA4 antibody, anti-PD-L1 antibody, and/or anti-PD-1 antibody.

Treatment with a cancer therapy includes a CD40L-Fc fusion protein (e.g., MEDI5083) alone or in combination with anti-CTLA4 antibody, anti-PD-L1 antibody, and/or anti-PD-1 antibody includes, for example, reducing the rate of progression of the cancer, retardation or stabilization of tumor growth, tumor shrinkage, and/or tumor regression. In some aspects the reduction or retardation of tumor growth can be statistically significant. A reduction in tumor growth can be measured by comparison to the growth of patient's tumor at baseline, against an expected tumor growth, against an expected tumor growth based on a large patient population, or against the tumor growth of a control population. In other embodiments, the methods of the invention increase survival.

Clinical response to administration of a cancer therapy can be assessed using diagnostic techniques known to clinicians, including but not limited to magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, and chromatography.

T-Cell Modulatory Pathways

There is mounting evidence that T cells control tumor growth and survival in cancer patients, both in early and late stages of the disease. However, tumor-specific T-cell responses are difficult to mount and sustain in cancer patients.

T cell modulatory pathways receiving significant attention signal through cytotoxic T lymphocyte antigen-4 (CTLA-4, CD152) and programmed death ligand 1 (PD-L1, also known as B7H-1 or CD274).

CTLA-4 is expressed on activated T cells and serves as a co-inhibitor to keep T-cell responses in check following CD28-mediated T-cell activation. CTLA-4 is believed to regulate the amplitude of the early activation of naïve and memory T cells following TCR engagement and to be part of a central inhibitory pathway that affects both antitumor immunity and autoimmunity. CTLA-4 is expressed on T cells, and the expression of its ligands CD80 (B7.1) and CD86 (B7.2), is largely restricted to antigen-presenting cells, T cells, and other immune mediating cells. Antagonistic anti-CTLA-4 antibodies that block the CTLA-4 signaling pathway have been reported to enhance T cell activation. One such antibody, ipilimumab, was approved by the FDA in 2011 for the treatment of metastatic melanoma. Another anti-CTLA-4 antibody, tremelimumab, was tested in phase III trials for the treatment of advanced melanoma but did not significantly increase the overall survival of patients compared to the standard of care (temozolomide or dacarbazine) at that time.

PD-L1 is also part of a complex system of receptors and ligands that are involved in controlling T cell activation. In normal tissue, PD-L1 is expressed on T cells, B cells, dendritic cells, macrophages, mesenchymal stem cells, bone marrow-derived mast cells, as well as various non-hematopoietic cells. Its normal function is to regulate the balance between T-cell activation and tolerance through interaction with its two receptors: programmed death 1 (also known as PD-1 or CD279) and CD80 (also known as B7-1 or B7.1). PD-L1 is also expressed by tumors and acts at multiple sites to help tumors evade detection and elimination by the host immune system. PD-L1 is expressed in a broad range of cancers with a high frequency. In some cancers, expression of PD-L1 has been associated with reduced survival and unfavorable prognosis. Antibodies that block the interaction between PD-L1 and its receptors (e.g., PD-1) are able to relieve PD-L1-dependent immunosuppressive effects and enhance the cytotoxic activity of antitumor T cells in vitro.

CD40L is a member of the TNF family of molecules which is primarily expressed on activated T cells (including Th0, Th1, and Th2 subtypes), and forms homotrimers similar to other members of this family. Further, CD40L has also been found expressed on Mast cells, and activated basophils and eosinophils. CD40L binds to the receptor CD40 on antigen-presenting cells (APC), which leads to many effects depending on the target cell type. In general, CD40L plays the role of a costimulatory molecule and induces activation in APC in association with T cell receptor stimulation by MHC molecules on the APC.

Signaling through the receptor CD40 by CD40L initiates a cascade of events that result in the activation of the CD40-bearing cells and optimal T cell priming. More specifically, the cognate interaction between CD40L and CD40 promotes the differentiation of B cells into antibody secreting cells and memory B cells (Burkly, In Adv. Exp. Med. Bio., Vol. 489., D. M. Monroe, U. Hedner, M. R. Hoffman, C. Negrier, G. F. Savidge, and G. C. I. White, eds. Klower Academic/Plenum Publishers, 2001, p. 135). Additionally, the interaction between CD40L and the CD40 promotes cell-mediated immunity through the activation of macrophages and dendritic cells and the generation of natural killer cells and cytotoxic T lymphocytes (see Burkly, supra).

Single-Chain Fc Fusion Proteins

Single chain CD40L Fc fusion proteins of the invention demonstrated stability and bioactivity. As described herein, CD40L stability and activity was due at least in part to the length of the linkers used in the CD40L Fc fusion proteins of the invention. This was surprising and unexpected, as other TNF ligand Fc fusion proteins have been generated, but tended to aggregate when peptide linkers greater than 8 amino acids in length were used. The CD40L Fc fusion proteins of the invention also provide other features and advantages of single chain Fc proteins.

It is known that naturally occurring soluble cytokine members of the TNF ligand family exhibit their bioactivity as homotrimers. However, trimeric complexes of TNF ligands tend to denature via dissociation of their monomers and are difficult to prepare from recombinant monomeric units. To prevent the dissociation of the homotrimers into monomers at least three monomers of a TNF ligand are covalently linked to one another via their C terminals and N terminals by means of peptide linkers to form a "single-chain (sc)" molecule. Therefore, the entire molecule (at least three monomers of a member of the TNF ligand family with the two peptide linkers) consists of a single protein strand, so that dissociation into monomers can no longer occur.

In addition, fusion of the TNF ligand to an Fc domain, as in the single-chain fusion proteins of the invention, may be used to obtain dimerization trimers. The dimerization of soluble domains is accomplished by assembly of two Fc-domains via disulfide bridges. The local enrichment of single chain TNF ligands on cells or neighboring cells has the potential to increase the bioactivity of these fusion proteins.

Anti-PD-L1 Antibodies

Durvalumab (MEDI4736) is an exemplary anti-PD-L1 antibody that is selective for PD-L1 and blocks the binding of PD-L1 to the PD-1 and CD80 receptors. Durvalumab can relieve PD-L1-mediated suppression of human T-cell activation in vitro and inhibits tumor growth in a xenograft model via a T-cell dependent mechanism.

Information regarding durvalumab (or fragments thereof) for use in the methods provided herein can be found in U.S. Pat. No. 8,779,108, the disclosure of which is incorporated herein by reference in its entirety. The fragment crystallizable (Fc) domain of durvalumab contains a triple mutation in the constant domain of the IgG1 heavy chain that reduces binding to the complement component C1q and the Fcγ receptors responsible for mediating antibody-dependent cell-mediated cytotoxicity (ADCC).

Durvalumab and antigen-binding fragments thereof for use in the methods provided herein comprises a heavy chain and a light chain or a heavy chain variable region and a light chain variable region. In a specific aspect, durvalumab or an antigen-binding fragment thereof for use in the methods provided herein comprises a light chain variable region and a heavy chain variable region. In a specific aspect, durvalumab or an antigen-binding fragment thereof for use in the methods provided herein comprises a heavy chain variable region and a light chain variable region, wherein the heavy chain variable region comprises the Kabat-defined CDR1, CDR2, and CDR3 sequences shown herein above, and wherein the light chain variable region comprises the Kabat-defined CDR1, CDR2, and CDR3 sequences shown herein above. Those of ordinary skill in the art would easily be able to identify Chothia-defined, Abm-defined or other CDR definitions known to those of ordinary skill in the art. In a specific aspect, durvalumab or an antigen-binding fragment thereof for use in the methods provided herein comprises the variable heavy chain and variable light chain CDR sequences of the 2.14H9OPT antibody as disclosed in U.S. Pat. No. 8,779,108, which is herein incorporated by reference in its entirety.

Anti-CTLA-4 Antibodies

Antibodies that specifically bind CTLA-4 and inhibit CTLA-4 activity are useful for enhancing an anti-tumor immune response. Information regarding tremelimumab (or antigen-binding fragments thereof) for use in the methods provided herein can be found in U.S. Pat. No. 6,682,736 (where it is referred to as 11.2.1), the disclosure of which is incorporated herein by reference in its entirety. Tremelimumab (also known as CP-675,206, CP-675, CP-675206, and ticilimumab) is a human IgG2 monoclonal antibody that is highly selective for CTLA-4 and blocks binding of CTLA-4 to CD80 (B7.1) and CD86 (B7.2). It has been shown to result in immune activation in vitro and some patients treated with tremelimumab have shown tumor regression.

Tremelimumab for use in the methods provided herein comprises a heavy chain and a light chain or a heavy chain variable region and a light chain variable region. In a specific aspect, tremelimumab or an antigen-binding fragment thereof for use in the methods provided herein comprises a light chain variable region comprising the amino acid sequences shown herein above and a heavy chain variable region comprising the amino acid sequence shown herein above. In a specific aspect, tremelimumab or an antigen-binding fragment thereof for use in the methods provided herein comprises a heavy chain variable region and a light chain variable region, wherein the heavy chain variable region comprises the Kabat-defined CDR1, CDR2, and CDR3 sequences shown herein above, and wherein the light chain variable region comprises the Kabat-defined CDR1, CDR2, and CDR3 sequences shown herein above. Those of ordinary skill in the art would easily be able to identify Chothia-defined, Abm-defined or other CDR definitions known to those of ordinary skill in the art. In a specific aspect, tremelimumab or an antigen-binding fragment thereof for use in the methods provided herein comprises the variable heavy chain and variable light chain CDR sequences of the 11.2.1 antibody as disclosed in U.S. Pat. No. 6,682,736, which is herein incorporated by reference in its entirety.

Other anti-CTLA-4 antibodies are described, for example, in US 20070243184. In one embodiment, the anti-CTLA-4 antibody is Ipilimumab, also termed MDX-010; BMS-734016.

Antibodies

Antibodies that selectively bind CTLA-4 and PD-L1, and inhibit the binding or activation of CTLA-4 and PD-L1 are useful in the methods of the invention.

In general, antibodies can be made, for example, using traditional hybridoma techniques (Kohler and Milstein (1975) Nature, 256: 495-499), recombinant DNA methods (U.S. Pat. No. 4,816,567), or phage display performed with antibody libraries (Clackson et al. (1991) Nature, 352: 624-628; Marks et al. (1991) J. Mol. Biol., 222: 581-597). For other antibody production techniques, see also Antibodies: A Laboratory Manual, eds. Harlow et al., Cold Spring Harbor Laboratory, 1988. The invention is not limited to any particular source, species of origin, method of production.

Intact antibodies, also known as immunoglobulins, are typically tetrameric glycosylated proteins composed of two light (L) chains of approximately 25 kDa each and two heavy (H) chains of approximately 50 kDa each. Two types of light chain, designated as the λ chain and the κ chain, are found in antibodies. Depending on the amino acid sequence of the constant domain of heavy chains, immunoglobulins can be assigned to five major classes: A, D, E, G, and M, and several of these may be further divided into subclasses (isotypes), e.g., IgG1, IgG2, IgG3, IgG4, IgA1, and IgA2.

The subunit structures and three-dimensional configurations of different classes of immunoglobulins are well known in the art. For a review of antibody structure, see Harlow et al., supra. Briefly, each light chain is composed of an N-terminal variable domain (VL) and a constant domain (CL). Each heavy chain is composed of an N-terminal variable domain (VH), three or four constant domains (CH), and a hinge region. The CH domain most proximal to VH is designated as CH1. The VH and VL domains consist of four regions of relatively conserved sequence called framework regions (FR1, FR2, FR3, and FR4), which form a scaffold for three regions of hypervariable sequence called complementarity determining regions (CDRs). The CDRs contain most of the residues responsible for specific interactions with the antigen. The three CDRs are referred to as CDR1, CDR2, and CDR3. CDR constituents on the heavy chain are referred to as H1, H2, and H3, while CDR constituents on the light chain are referred to as L1, L2, and L3, accordingly. CDR3 and, particularly H3, are the greatest source of molecular diversity within the antigen-binding domain. H3, for example, can be as short as two amino acid residues or greater than 26.

The Fab fragment (Fragment antigen-binding) consists of the VH-CH1 and VL-CL domains covalently linked by a disulfide bond between the constant regions. To overcome the tendency of non-covalently linked VH and VL domains in the Fv to dissociate when co-expressed in a host cell, a so-called single chain (sc) Fv fragment (scFv) can be constructed. In a scFv, a flexible and adequately long polypeptide links either the C-terminus of the VH to the N-terminus of the VL or the C-terminus of the VL to the N-terminus of the VH. Most commonly, a 15-residue (Gly4Ser)3 peptide is used as a linker but other linkers are also known in the art.

Antibody diversity is a result of combinatorial assembly of multiple germline genes encoding variable regions and a variety of somatic events. The somatic events include recombination of variable gene segments with diversity (D) and joining (J) gene segments to make a complete VH region and the recombination of variable and joining gene segments to make a complete VL region. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation.

Based on the estimated number of germline gene segments, the random recombination of these segments, and random VH-VL pairing, up to $1.6 \times 10^7$ different antibodies could be produced (Fundamental Immunology, 3rd ed., ed. Paul, Raven Press, New York, N.Y., 1993). When other processes which contribute to antibody diversity (such as somatic mutation) are taken into account, it is thought that upwards of $1 \times 10^{10}$ different antibodies could be potentially generated (Immunoglobulin Genes, 2nd ed., eds. Jonio et al., Academic Press, San Diego, Calif., 1995). Because of the many processes involved in antibody diversity, it is highly unlikely that independently generated antibodies will have identical or even substantially similar amino acid sequences in the CDRs.

The sequences of exemplary anti-CTLA-4 and anti-PD-L1 CDRs are provided herein. The structure for carrying a CDR will generally be an antibody heavy or light chain or a portion thereof, in which the CDR is located at a location corresponding to the CDR of naturally occurring VH and VL. The structures and locations of immunoglobulin variable domains may be determined, for example, as described in Kabat et al., Sequences of Proteins of Immunological Interest, No. 91-3242, National Institutes of Health Publications, Bethesda, Md., 1991.

Antibodies of the invention (e.g., anti-CTLA-4, anti-PD-L1) may optionally comprise antibody constant regions or parts thereof. For example, a VL domain may have attached, at its C terminus, antibody light chain constant domains including human Cκ or Cλ chains. Similarly, a specific antigen-binding domain based on a VH domain may have attached all or part of an immunoglobulin heavy chain derived from any antibody isotype, e.g., IgG, IgA, IgE, and IgM and any of the isotype sub-classes, which include but are not limited to, IgG1 and IgG4.

One of ordinary skill in the art will recognize that the antibodies of this invention may be used to detect, measure, and inhibit proteins that differ somewhat from CTLA-4 and PD-L1. The antibodies are expected to retain the specificity of binding so long as the target protein comprises a sequence which is at least about 60%, 70%, 80%, 90%, 95%, or more identical to any sequence of at least 100, 80, 60, 40, or 20 of contiguous amino acids described herein. The percent identity is determined by standard alignment algorithms such as, for example, Basic Local Alignment Tool (BLAST) described in Altshul et al. (1990) J. Mol. Biol., 215: 403-410, the algorithm of Needleman et al. (1970) J. Mol. Biol., 48: 444-453, or the algorithm of Meyers et al. (1988) Comput. Appl. Biosci., 4: 11-17.

In addition to the sequence homology analyses, epitope mapping (see, e.g., Epitope Mapping Protocols, ed. Morris, Humana Press, 1996) and secondary and tertiary structure analyses can be carried out to identify specific 3D structures assumed by the disclosed antibodies and their complexes with antigens. Such methods include, but are not limited to, X-ray crystallography (Engstom (1974) Biochem. Exp. Biol., 11:7-13) and computer modeling of virtual representations of the presently disclosed antibodies (Fletterick et al. (1986) Computer Graphics and Molecular Modeling, in Current Communications in Molecular Biology, Cold Spring Harbor Laboratory, Cold Spring Harbor, N.Y.).

Derivatives

Polypeptides (e.g., CD40L) and antibodies of the invention (e.g., anti-CTLA-4, anti-PD-L1) may include variants of these sequences that retain the ability to specifically bind their targets. Such variants may be derived from the sequence of these polypeptides or antibodies by a skilled artisan using techniques well known in the art. For example, amino acid substitutions, deletions, or additions, can be made in the FRs and/or in the CDRs. While changes in the FRs are usually designed to improve stability and immunogenicity of the antibody, changes in the CDRs are typically designed to increase affinity of the antibody for its target. Variants of FRs also include naturally occurring immunoglobulin allotypes. Such affinity-increasing changes may be determined empirically by routine techniques that involve altering the CDR and testing the affinity antibody for its target. For example, conservative amino acid substitutions can be made within any one of the disclosed CDRs. Various alterations can be made according to the methods described in Antibody Engineering, 2nd ed., Oxford University Press, ed. Borrebaeck, 1995. These include but are not limited to nucleotide sequences that are altered by the substitution of different codons that encode a functionally equivalent amino acid residue within the sequence, thus producing a "silent" change. For example, the nonpolar amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid.

Derivatives and analogs of polypeptides and/or antibodies of the invention can be produced by various techniques well known in the art, including recombinant and synthetic methods (Maniatis (1990) Molecular Cloning, A Laboratory Manual, 2nd ed., Cold Spring Harbor Laboratory, Cold Spring Harbor, N.Y., and Bodansky et al. (1995) The Practice of Peptide Synthesis, 2nd ed., Spring Verlag, Berlin, Germany).

In one embodiment, a method for making a VH domain which is an amino acid sequence variant of a VH domain of the invention comprises a step of adding, deleting, substituting, or inserting one or more amino acids in the amino acid sequence of the presently disclosed VH domain, optionally combining the VH domain thus provided with one or more VL domains, and testing the VH domain or VH/VL combination or combinations for specific binding to the antigen. An analogous method can be employed in which one or more sequence variants of a VL domain disclosed herein are combined with one or more VH domains.

Analogous shuffling or combinatorial techniques are also disclosed by Stemmer (Nature (1994) 370: 389-391), who describes the technique in relation to a β-lactamase gene but observes that the approach may be used for the generation of antibodies.

In further embodiments, one may generate novel VH or VL regions carrying one or more sequences derived from the sequences disclosed herein using random mutagenesis of one or more selected VH and/or VL genes. One such technique, error-prone PCR, is described by Gram et al. (Proc. Nat. Acad. Sci. U.S.A. (1992) 89: 3576-3580).

Another method that may be used is to direct mutagenesis to CDRs of VH or VL genes. Such techniques are disclosed by Barbas et al. (Proc. Nat. Acad. Sci. U.S.A. (1994) 91: 3809-3813) and Schier et al. (J. Mol. Biol. (1996) 263: 551-567).

Similarly, one or more, or all three CDRs may be grafted into a repertoire of VH or VL domains, which are then screened for an antigen-binding fragment specific for CTLA-4 or PD-L1.

A portion of an immunoglobulin variable domain will comprise at least one of the CDRs substantially as set out herein and, optionally, intervening framework regions from the scFv fragments as set out herein. The portion may include at least about 50% of either or both of FR1 and FR4, the 50% being the C-terminal 50% of FR1 and the N-terminal 50% of FR4. Additional residues at the N-terminal or C-terminal end of the substantial part of the variable domain may be those not normally associated with naturally occurring variable domain regions. For example, construction of antibodies by recombinant DNA techniques may result in the introduction of N- or C-terminal residues encoded by linkers introduced to facilitate cloning or other manipulation steps. Other manipulation steps include the introduction of linkers to join variable domains to further protein sequences including immunoglobulin heavy chain constant regions, other variable domains (for example, in the production of diabodies), or proteinaceous labels as discussed in further detail below.

A skilled artisan will recognize that antibodies of the invention may comprise antigen-binding fragments containing only a single CDR from either VL or VH domain. Either one of the single chain specific binding domains can be used to screen for complementary domains capable of forming a two-domain specific antigen-binding fragment capable of, for example, binding to CTLA-4 and PD-L1.

Antibodies of the invention (e.g., anti-CTLA-4 and/or anti-PD-L1) described herein can be linked to another functional molecule, e.g., another peptide or protein (albumin, another antibody, etc.). For example, the antibodies can be linked by chemical cross-linking or by recombinant methods. The antibodies may also be linked to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337. The antibodies can be chemically modified by covalent conjugation to a polymer, for example, to increase their circulating half-life. Exemplary polymers and methods to attach them are also shown in U.S. Pat. Nos. 4,766,106; 4,179,337; 4,495,285, and 4,609,546.

The disclosed antibodies may also be altered to have a glycosylation pattern that differs from the native pattern. For example, one or more carbohydrate moieties can be deleted and/or one or more glycosylation sites added to the original antibody. Addition of glycosylation sites to the presently disclosed antibodies may be accomplished by altering the amino acid sequence to contain glycosylation site consensus sequences known in the art. Another means of increasing the number of carbohydrate moieties on the antibodies is by chemical or enzymatic coupling of glycosides to the amino acid residues of the antibody. Such methods are described in WO 87/05330, and in Aplin et al. (1981) CRC Crit. Rev. Biochem., 22: 259-306. Removal of any carbohydrate moieties from the antibodies may be accomplished chemically or enzymatically, for example, as described by Hakimuddin et al. (1987) Arch. Biochem. Biophys., 259: 52; and Edge et al. (1981) Anal. Biochem., 118: 131 and by Thotakura et al. (1987) Meth. Enzymol., 138: 350. The antibodies may also be tagged with a detectable, or functional, label. Detectable labels include radiolabels such as 131I or 99Tc, which may also be attached to antibodies using conventional chemistry. Detectable labels also include enzyme labels such as horseradish peroxidase or alkaline phosphatase. Detectable labels further include chemical moieties such as biotin, which may be detected via binding to a specific cognate detectable moiety, e.g., labeled avidin.

Antibodies, in which CDR sequences differ only insubstantially from those set forth herein are encompassed within the scope of this invention. Typically, an amino acid is substituted by a related amino acid having similar charge, hydrophobic, or stereochemical characteristics. Such substitutions would be within the ordinary skills of an artisan. Unlike in CDRs, more substantial changes can be made in FRs without adversely affecting the binding properties of an antibody. Changes to FRs include, but are not limited to, humanizing a non-human derived or engineering certain framework residues that are important for antigen contact or for stabilizing the binding site, e.g., changing the class or subclass of the constant region, changing specific amino acid residues which might alter the effector function such as Fc receptor binding, e.g., as described in U.S. Pat. Nos. 5,624,821 and 5,648,260 and Lund et al. (1991) J. Immun. 147: 2657-2662 and Morgan et al. (1995) Immunology 86: 319-324, or changing the species from which the constant region is derived.

One of skill in the art will appreciate that the modifications described above are not all-exhaustive, and that many other modifications would obvious to a skilled artisan in light of the teachings of the present disclosure.

Co-Therapy

Treatment of a patient with a solid tumor using a combination of the invention, such as an CD40L-Fc fusion protein alone or in combination with an immune checkpoint inhibitor (e.g., an anti-CTLA4 antibody, anti-PD-L1 antibody, and/or anti-PD-1 antibody, or antigen-binding fragments thereof), as provided herein can result in an additive or synergistic effect. As used herein, the term "synergistic" refers to a combination of therapies (e.g., a combination of a CD40L-Fc fusion protein, anti-CTLA-4 antibody, and anti-PD-L1 antibody).

In some embodiments, a synergistic effect of a combination of therapies (e.g., a combination of a CD40L-Fc fusion protein, anti-CTLA-4 antibody, and anti-PD-L1 antibody) may permit the use of lower dosages of one or more of the therapeutic agents and/or less frequent administration of said therapeutic agents to a patient with a solid tumor. For example, the ability to utilize lower dosages of therapeutic agents and/or to administer said therapies less frequently has the potential to reduce the toxicity associated with the administration of said therapies to a subject without reducing the efficacy of said therapies in the treatment of a solid tumor.

In co-therapy, a combination of a CD40L-Fc fusion protein, anti-CTLA-4 antibody, and anti-PD-L1 antibody may be administered together in one administration in one or more separate administrations. In addition, a synergistic effect can result in improved efficacy of therapeutic agents in the management, treatment, or amelioration of an solid tumor. The synergistic effect of a combination of therapeutic agents can avoid or reduce adverse or unwanted side effects associated with the use of any single therapy.

CD40L-Fc Fusion Protein Production

Recombinant expression of a CD40L-Fc fusion protein of the invention requires construction of an expression vector containing a polynucleotide that encodes the CD40L-Fc fusion protein. Once a polynucleotide encoding a CD40L-Fc fusion protein has been obtained, the vector for the production of the CD40L-Fc fusion protein may be produced by recombinant DNA technology using techniques well known in the art. Thus, methods are provided for preparing a protein by expressing a polynucleotide containing a CD40L-Fc fusion protein encoding nucleotide sequence. Methods that are well known to those skilled in the art can be used to construct expression vectors containing CD40L or Fc polypeptide coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding a CD40L-Fc fusion protein of the invention, operably linked to a promoter.

The expression vector is transferred to a host cell by conventional techniques and the transfected cells are then cultured by conventional techniques to produce a CD40L-Fc fusion protein of the invention. Thus, the invention includes host cells containing a polynucleotide encoding a CD40L-Fc fusion protein of the invention, operably linked to a heterologous promoter. Suitable host cells include, but are not limited to, microorganisms such as bacteria (e.g., *E. coli* and *B. subtilis*).

A variety of host-expression vector systems may be utilized to express the CD40L-Fc fusion protein of the invention. Such host-expression systems represent vehicles by which the coding sequences of interest may be produced and subsequently purified, but also represent cells which may, when transformed or transfected with the appropriate nucleotide coding sequences, express a CD40L-Fc fusion protein of the invention in situ. These include but are not limited to microorganisms such as bacteria (e.g., *E. coli* and *B. subtilis*) transformed with recombinant bacteriophage DNA, plasmid DNA or cosmid DNA expression vectors containing CD40L-Fc fusion protein coding sequences or mammalian cell systems (e.g., COS, CHO, BHK, 293, NSO, and 3T3 cells). Once a CD40L-Fc fusion protein of the invention has been produced by recombinant expression, it may be purified by any method known in the art for purification of a protein.

Assaying CD40L-Fc Fusion Protein Properties and Activities

The stability of the CD40L-Fc monomer subunits of the invention, isolated or as part of a multimer, can be readily measured by techniques well known in the art, such as thermal ($T_m$) and chaotropic denaturation (such as treatment with urea, or guanidine salts), protease treatment (such as treatment with thermolysin) or another art accepted methodology to determine protein stability. A comprehensive review of techniques used to measure protein stability can be found, for example in "Current Protocols in Molecular Biology" and "Current Protocols in Protein Science" by John Wiley and Sons. 2007.

The binding affinity and other binding properties of a CD40L-Fc fusion proteins to CD40 may be determined by a variety of in vitro assay methods known in the art including for example, equilibrium methods (e.g., enzyme-linked immunoabsorbent assay (ELISA) or kinetics (e.g., BIACORE® analysis), and other methods such as indirect binding assays, competitive binding assays, gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999).

Additional in vitro and in vivo methods for determining the function or activity of CD40L-Fc fusion proteins are described herein. These assays may be used to determine one or more of an immune response (e.g., one or more of T-cell function and memory, B-cell activation or proliferation, dendritic cell maturation or activation, Th1 cytokine or chemokine response, monocyte-derived macrophage M1/M2 polarization, antigen presentation and/or immunosuppression of a tumor microenvironment). In vivo, various animal models for assaying anti-cancer or anti-tumor activity are known in the art, including for example, the B16-F10 tumor mouse model. Additional, methods of assessing pharmacodynamic and pharmacokinetic properties are also well-known.

Kits

The invention provides kits for enhancing anti-tumor activity. In various embodiments, the kit includes a CD40L-Fc fusion protein (e.g., MEDI5083). The kit may comprise additional therapeutic compositions including for example an anti-CTLA-4 antibody (e.g., tremelimumab), anti-PD-L1 antibody (e.g., durvalumab), and/or an anti-PD-1 antibody.

In some embodiments, the kit comprises a sterile container which contains a therapeutic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, the kit further comprises instructions for administering the therapeutic combinations of the invention. In particular embodiments, the instructions include at least one of the following: description of the therapeutic agent; dosage schedule and administration for enhancing anti-tumor activity; precautions; warnings; indications; counter-indications; over dosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Examples

The invention is now described with reference to the following examples. These examples are illustrative only and the invention should in no way be construed as being limited to these examples but rather should be construed to encompass any and all variations which become evident as a result of the teachings provided herein.

Example 1. Generation of CD40L-Fc and Stability Study

CD40L plays the role of a costimulatory molecule and binds to the receptor CD40 on antigen-presenting cells (APC), which leads to many effects depending on the target cell type, including B-cell activation and presentation of anti-tumor antibody immune responses, activation of macrophages and dendritic cells, and the generation of natural killer cells and cytotoxic T lymphocytes.

Fusion proteins were constructed comprising a single chain fusion of three CD40 ligand (CD40L) subunits and an Fc monomer (IgG4P Fc) linked via peptide linkers (CD40L-Fc) (FIG. 1). The CD40L-Fc fusion proteins included scCD40L-IgG4P-FP6 (MEDI5083), scCD40L-IgG4P-FP7, and a Murine surrogate (FP5-like, mouse IgG1 D265A Fc). The physical properties of CD40L-Fc constructs were tested and were observed to be similar (Table 1).

TABLE 1

Comparison of CD40L-Fc Constructs

| Construct | Inter-unit Linker sequence | % non-aggregate from protein A. | MW from light scattering (kDa) | Final yield (mg/L) |
|---|---|---|---|---|
| FP7 C194W | GGGGSGGGGSGGGGS (SEQ ID NO: 4) | 90 | 157 | 155 |
| FP6 C194W | GGGGSGGGS (SEQ ID NO: 2) | 87 | 157 | 78 |
| WT FP5 | GGGSGGS (SEQ ID NO: 37) | 85 | 143 | 101 |

Figure 2:
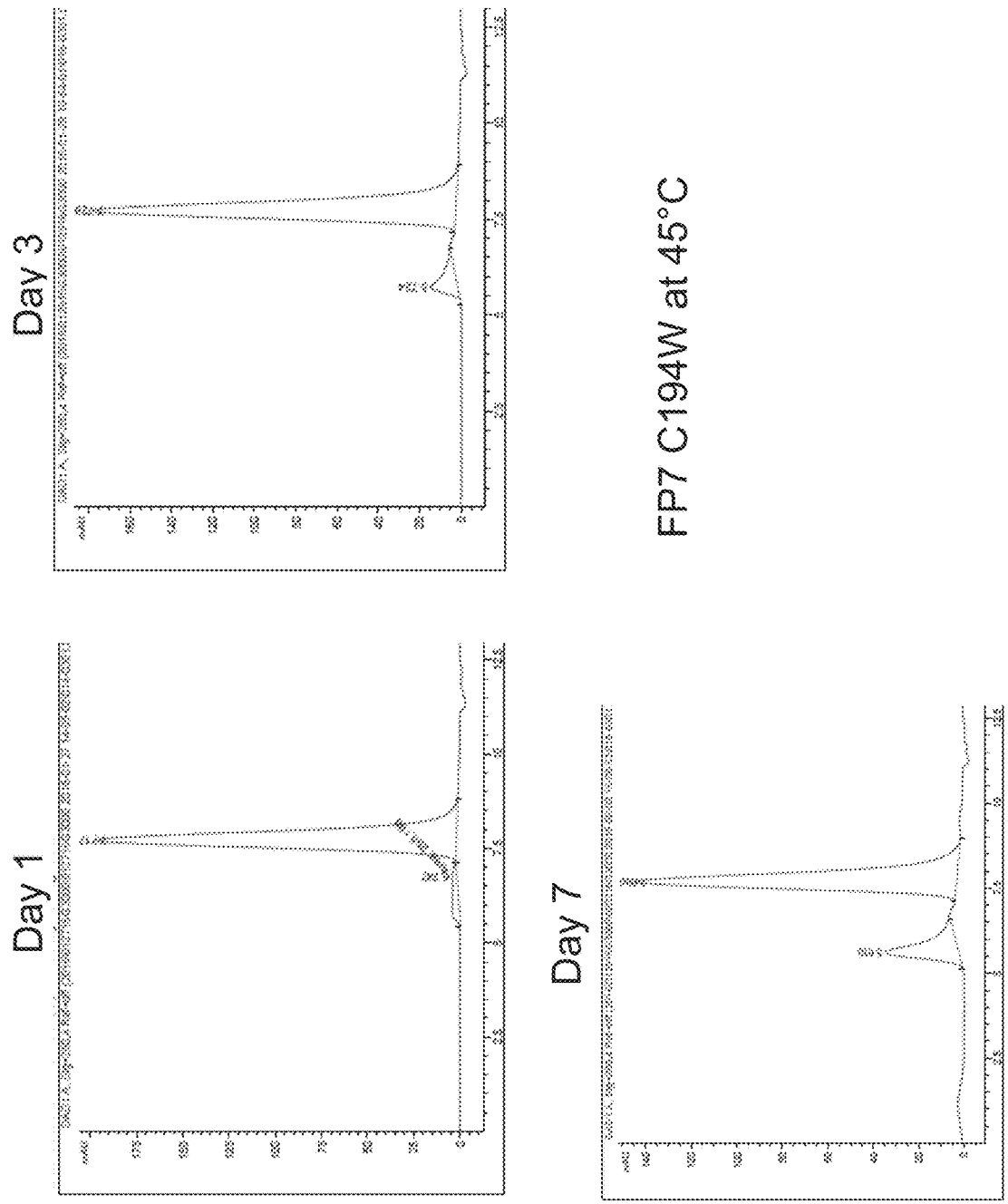
FIG. 2 is a series of representative high performance size exclusion chromatograpy (HPSEC) chromatograms depicting stability data for the CD40L-Fc fusion protein scCD40L-IgG4P-FP7, which comprises a C194W substitution (relative to the full-length membrane bound CD40L amino acid sequence), at 45° C. at day 1 (top left), day 3 (top right), and day 7 (bottom left).

Stability data were generated according to the following protocol. Samples were concentrated to 5 mg/mL in PBS, and incubated at room temperature and 45° C. The samples were tested by High Performance Size Exclusion Chromatography (HPSEC) at varying time points (e.g, Day 1, 3, 7, etc.). Representative HPSEC chromatograms for FP7 C194W are shown at FIG. 2. Stability data for the CD40L-Fc constructs showed minimal change over time at room temperature for up to 7 days and increased aggregation with time at 45° C. (Table 2).

TABLE 2

Stability data for CD40L-Fc Constructs

| Construct | Day 1 RT | Day 3 RT | Day 7 RT | Day 1 45° C. | Day 3 45° C. | Day 7 45° C. |
|---|---|---|---|---|---|---|
| FP7 C194W | 100 | 100 | 100 | 96 | 93 | 81 |
| FP6 C194W | 100 | 100 | 99 | 96 | 93 | 86 |
| WT FP5 | 100 | 99 | 100 | 96 | 82 | 76 |

Figure 3:
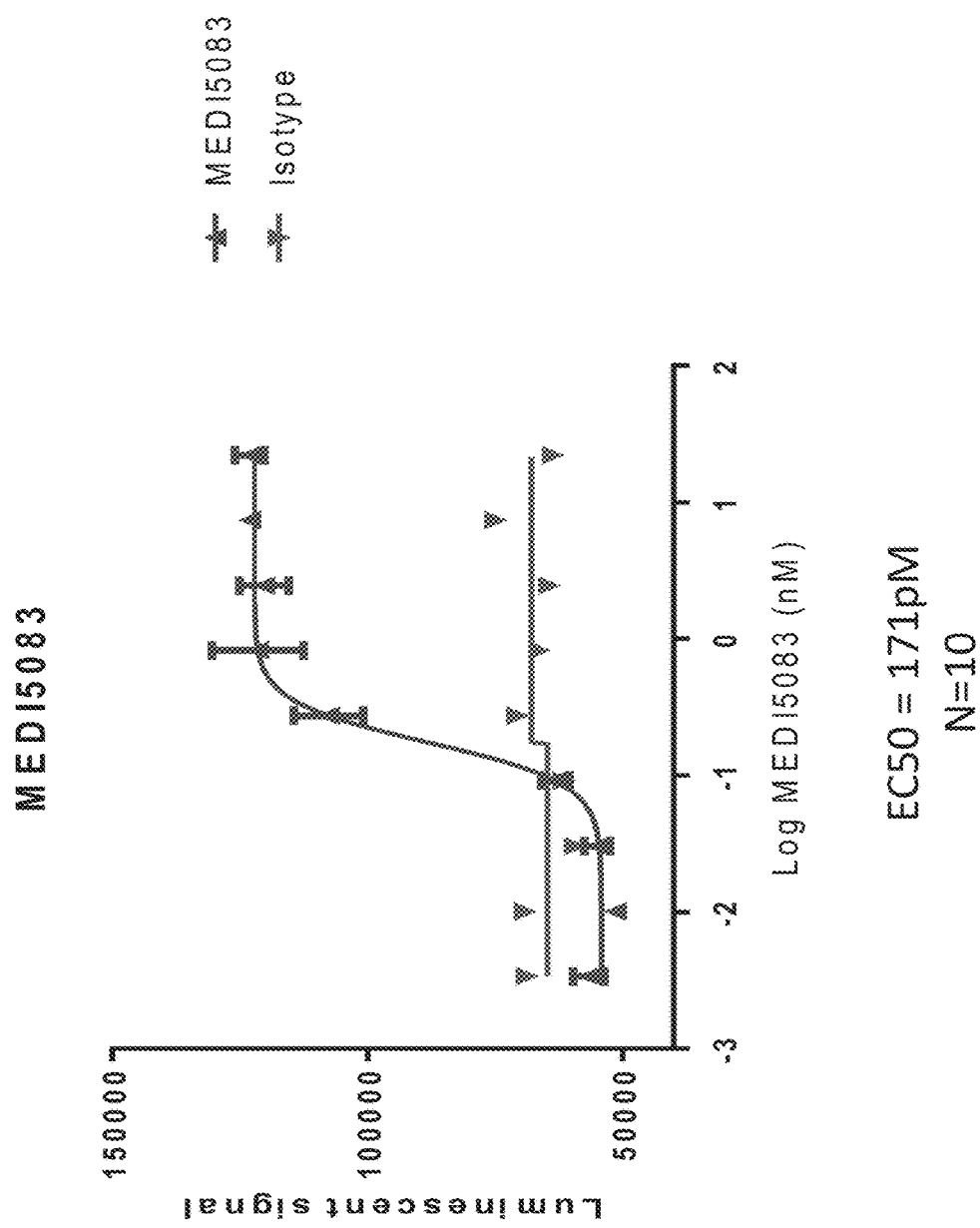
FIG. 3 is a graph showing MEDI5083 stability sample bioactivity, as measured by the NFκB Luciferase assay.

Samples of FP6 on a stability program were tested for bioactivity in the HEK293 human CD40 NFκB Luciferase reporter system, as described herein. MEDI5083 stability sample bioactivity, as measured by the NFκB Luciferase assay, was comparable to the control sample, both in the general shape and parameters of the curve and particularly in the IC50 value, scoring in the anticipated 100-200 pM range (FIG. 3).

Example 2. The CD40L-Fc Fusion Protein CD40L-FP7 has CD40L Bioactivity

The FP6 CD40L fusion protein (MEDI5083) exerts biological activity through binding and signaling through the surface bound human CD40 in immune system cells such as B-cells and dendritic cells. To determine CD40 mediated activity of CD40L fusion protein FP7, HEK293 CD40 NFκB-Luc cell line and Ramos-Blue NFκB/AP-1 reporter B-lymphocyte systems were used.

Rapid, simple surrogate assays have been developed using a human HEK cell transfected with human CD40 and an NFκB-Luciferase reporter system or Ramos-Blue cell transfected with an NFκB/AP-1 reporter system. In this study, the activity of FP7 CD40L fusion protein (MedImmune) was evaluated relative to MEDI5083 (MedImmune) and an isotype control (Isotype Human IgG4; MedImmune). FP7 CD40L and MEDI5083 were prepared according to the 2× and 1× drug dilution schemes. For 2× drug, the following dilution scheme was used: 200 nM, 66.7 nM, 22.2 nM, 7.4 nM, 2.5 nM, 823 pM, 274 pM, 92 pM, 31 pM, 10 pM, 3.4 pM, and 0 pM. For 1× drug, the following dilution scheme was used: 100 nM, 33.4 nM, 11.1 nM, 3.7 nM, 1.3 nM, 412 pM, 137 pM, 46 pM, 15 pM, 5 pM, 1.7 pM, 0 pM.

Materials and Methods

Hu CD40 HEK Bioactivity Assay Protocol

Hu CD40 293 HEK NFκB c3 cells were maintained in DMEM (GIBCO) plus 10% Heat-inactivated FBS (HI-FBS; GIBCO) and Pen Strep (GIBCO). The cells are adherent and tend to form stacks or islands of cells as confluency increases. Cells were split when approaching 75% confluency. To harvest cells, media was aspirated, 0.25% Trypsin-EDTA (5 mL; GIBCO) was added and the cell layer was coated with rocking. Trypsin was removed, media (10 mL) was added, and cells were removed by agitation. Harvested cells were adjusted to $5\times10^5$ cells/mL in DMEM plus 2% HI-FBS, added (100 μL) to the wells of a flat-bottomed Poly D-L Lysine Biocoat 96-well plate ($5\times10^4$ cells/well; Corning), and placed in a 37° C. incubator for 24 hours. After incubation, media was aspirated from the plate. One hundred (100) μL of 1× drug was carefully added to each well (e.g., down the side of the well) and care was taken to minimize detachment of the cells. The cells were returned to the 37° C. incubator for 24 hours. Luciferase reagent (Bright-Glo Luciferase Assay Substrate; Promega) was prepared, allowed to equilibrate to room temperature, and added (100 μL) to each well. The cells and reagent were mixed well to ensure complete cell lysis, and immediately read on a PerkinElmer Evision-02 Luminometer plate reader.

Ramos-Blue Bioactivity Assay Protocol

Ramos-Blue NFκB/AP-1 reporter B-lymphocytes (Invivogen) were maintained in IMDM GlutaMAX (GIBCO) plus 10% HI-FBS (GIBCO), Pen Strep (GIBCO) and Zeocin (100 μg/mL; InvivoGen) media. The cells are non-adherent, and cultures were initiate at $5\times10^5$ cells/mL and kept below $6\times10^6$/mL. On day −1, cells were split into IMDM GlutaMAX plus 10% HI-FBS and pen/strep (Zeo-free) media. Cells were harvested, adjusted to $4\times10^6$ cells/mL, and added (100 μL) to the wells of a flat-bottomed 96-well plate ($4\times10^5$ cells/well; Falcon). One hundred (100) μL 2× drug in Zeo-free media was added to each well, and the cells were placed in a 37° C. incubator for 24 hours. Supernatant from the Ramos-Blue cells (40 μL) was transferred to the wells of a flat-bottomed 96-well plate. AP-1 QUANTI-Blue reagent (one pouch dissolved in 100 mL sterile water; Invivogen) was prepared and the AP-1 QUANTI-Blue reagent (160 µL) was added to each well. The plate containing the cells and AP-1 QUANTI-Blue reagent was placed in a 37° C. incubator for up to 1 hour, and read on a SpectraMax M5 spectrophotometer at 655 nm.

Figure 4:
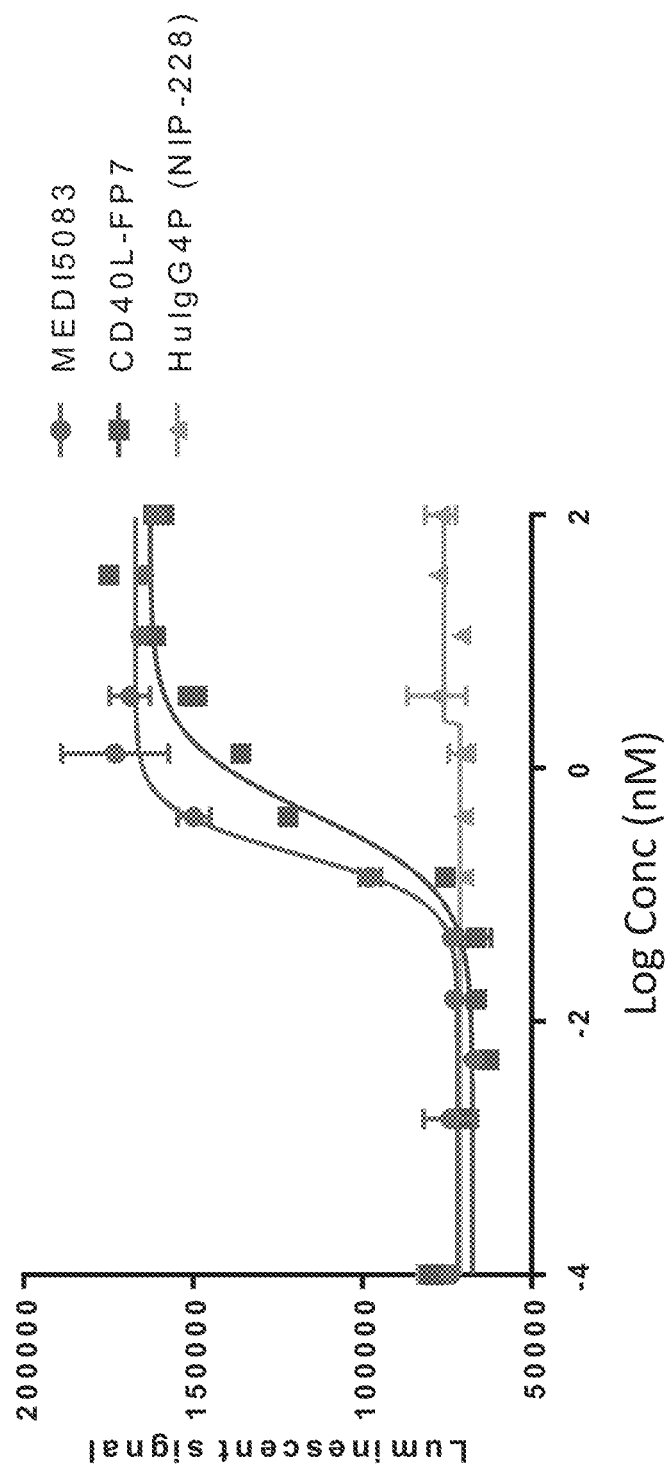
FIG. 4 is a graph depicting a bioactivity assessment of CD40L-FP7 referenced to MEDI5083 and a human IgG4P isotype control in a HuCD40 293 HEK NFκB c3 cell model.
Figure 5:
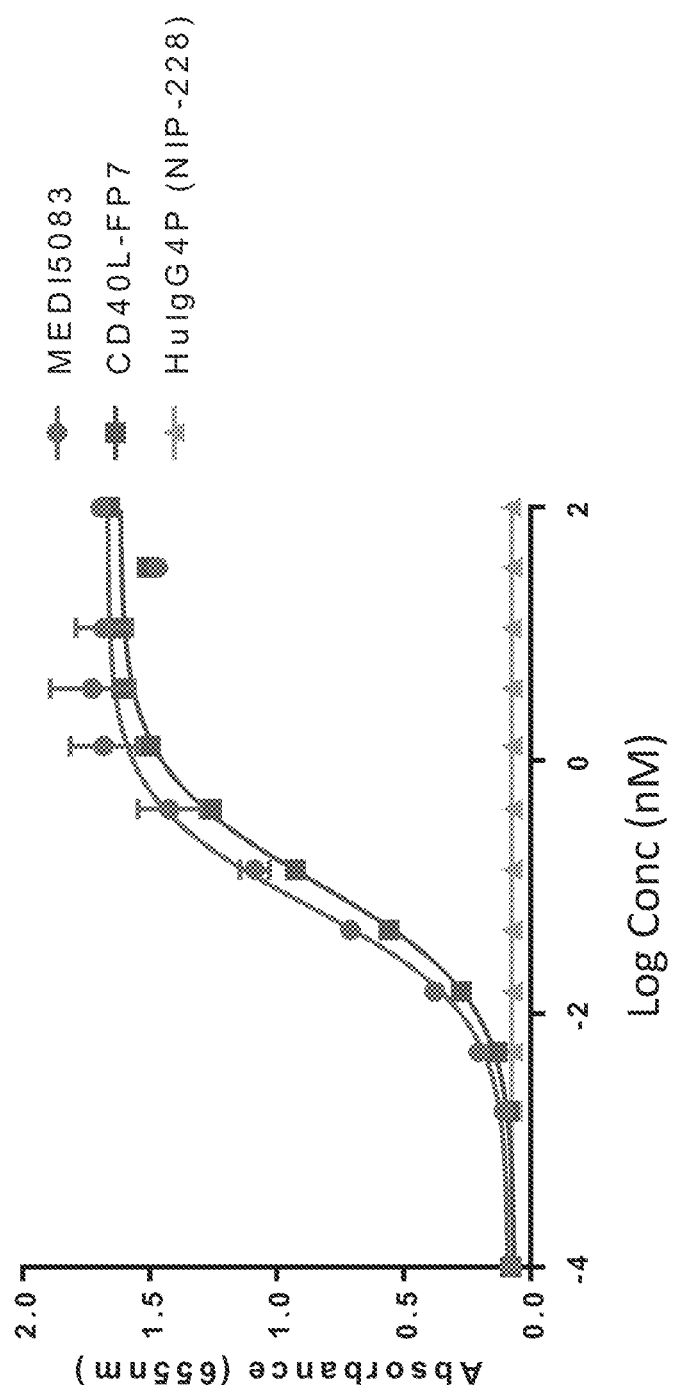
FIG. 5 is a graph depicting a bioactivity assessment of CD40L-FP7 referenced to MEDI5083 and a human IgG4P isotype control in a Ramos-Blue NFκB/AP-1 B-cells cell model.
Figure 6:
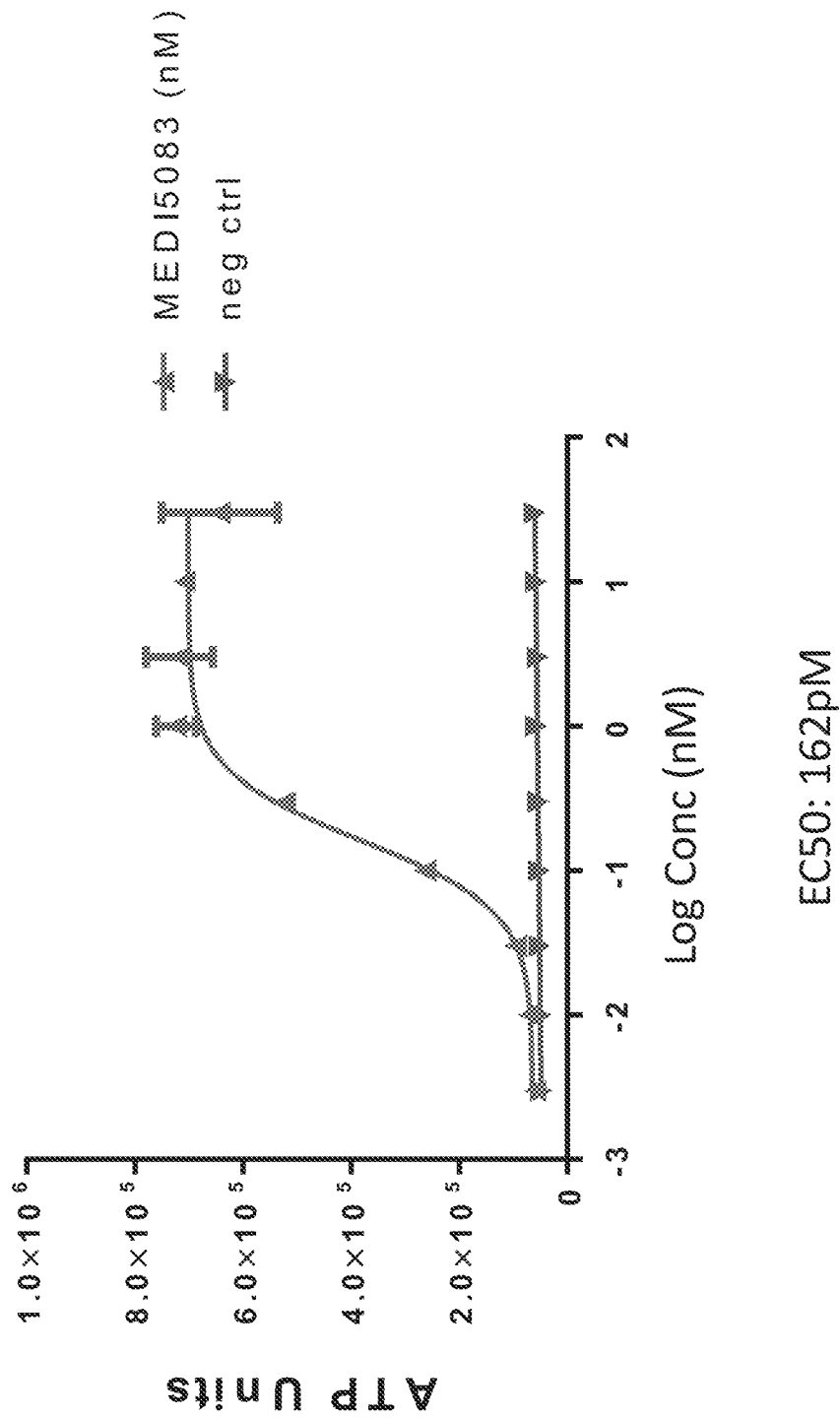
FIG. 6 is a graph showing that MEDI5083 stimulated human primary B cell proliferation.

CD40L-FP7 showed biological activity equivalent to MEDI5083 in both reporter cell line assays (FIGS. 4 and 5 and Tables 3 and 4). The CD40L subunits in the CD40L-FP7 fusion protein are linked via a 9-amino acid GlySer peptide linker. Surprisingly, despite having an increased linker length (>8 amino acids) relative to other single chain TNF ligand-Fc fusion proteins, the linker length of 9 amino acids did not reduce CD40L activity and there was no aggregation of the CD40L-FP7 fusion protein. The human IgG4P isotype control NIP-228 showed no activity over background in either reporter assay. For the Ramos-Blue reporter assay, incubation with QUANTI-Blue AP-1 detection medium for 60 min. (FIG. 5) and 30 min. displayed similar curves. However, incubation with QUANTI-Blue AP-1 detection medium for 60 min. resulted in a larger dynamic range than 30 min. In another experiment, MEDI5083 stimulated human primary B cell proliferation (FIG. 6). Thus, these experiments showed that MEDI5083 had bioactivity and can activate adaptive immunity.

TABLE 3

Bioavailability assessment of CD40L-FP7 referenced to MEDI5083 and a human IgG4P isotype control: HuCD40 293 HEK NFκB c3 cell model

| Best-fit values | Test sample description | | |
|---|---|---|---|
| | MEDI5083 | CD40L-FP7 | HuIgG4P |
| Bottom | 71966 | 67530 | 75990 |
| Top | 167096 | 162767 | 71170 |
| LogEC50 | −0.6775 | −0.3582 | ~−0.3561 |
| HillSlope | 2.397 | 1.424 | ~−60.20 |
| EC50 (nM) | 0.2102 | 0.4383 | ~2.270 |
| Span | 95130 | 95237 | −4820 |
| R Square | 0.9850 | 0.9695 | 0.2588 |

TABLE 4

Bioavailability assessment of CD40L-FP7 referenced to MEDI5083 and a human IgG4P isotype control: Ramos-Blue NFκB/AP-1 B-cells cell model

| Best-fit values | Test sample description | | |
|---|---|---|---|
| | MEDI5083 | CD40L-FP7 | HuIgG4P |
| Bottom | 0.08990 | 0.06519 | 0.07544 |
| Top | 1.667 | 1.618 | ~27.19 |
| LogEC50 | −1.146 | −0.9699 | ~2.317 |
| HillSlope | 1.023 | 0.9531 | ~12.20 |
| EC50 (nM) | 0.07153 | 0.1072 | ~207.5 |
| Span | 1.577 | 1.553 | ~27.11 |
| R Square | 0.9810 | 0.9965 | 0.1639 |

Example 3. The CD40L-Fc Fusion Protein MEDI5083 Activated Human Monocyte-Derived Dendritic Cells (MoDCs)

MEDI5083 exerts biological activity through the receptor CD40 in immune system cells such as dendritic cells, B-cells and macrophages. CD40L activators have been shown to increase cell surface activation markers and inflammatory cytokine secretion in dendritic cells detectable by FACS and ELISA respectively. This study was designed to determine whether pretreatment of MoDC with MEDI5083 enhanced response in human MoDCs.

Materials and Methods

MoDC Initiation and Culture

Human monocytes (e.g fresh) were cultured in RPMI (RPMI 1640+Glut media; GIBCO)+10% Heat-inactivated FBS (HI-FBS; GIBCO) (=cRPMI) supplemented with GM-CSF and IL-4 (both 100 ng/mL; R&D Systems) for 6 days, refeeding with cytokines every 48 hours. After 6 days, the monocyte-derived dendritic cells (MoDC) (characterized by loss of adherence and the appearance of cell membrane extrusions) were counted and adjusted to $1 \times 10^6$/mL in cRPMI. On day 6, characterization was performed by FACS (MACSQUANT Pippen) on a $1 \times 10^6$ mL aliquot from each donor.

MoDC Drug Treatment and Activation

For each donor, MoDCs (100 µL) in cRPMI were added to the wells of 96-well plates ($1 \times 10^5$ cells per well). Drug stocks (4×) of MEDI5083 (1:3 dilution) in cRPMI were generated to give a final concentration of FP6 ranging from 100 nM to 15 pM. For 4× drug, the following dilution scheme was used: 200 nM, 100 nM, 33.3 nM, 11.1 nM, 3.7 nM, 1.2 nM, 400 pM, 140 pM, 46 pM, 15 pM, 0 pM. Isotype control (100 nM) was used for no drug (0 pM). Additionally, for the fixed concentration of drug to be added in combination wells, 4× drug stocks in cRPMI were generated to give a final concentration of 4 nM MEDI5083. 4× drug (50 µL) and 50 µL cRPMI were added to the single drug treatment wells. After 24 hours, supernatants (130 µL) were harvested and transferred to labelled 96-well plates and frozen for subsequent cytokine analysis (IFN-γ, IL-10, IL-12p70, IL-13, IL-1β, IL-2, IL-4, IL-5, IL-8, TNF-α). Cells were processed by FACS.

Extracellular FACS Staining Protocol: Phenotypic/Functional Panel

After 24 hours, the MoDC cells have adhered to the plate. Add DPBS w/o Ca/Mg (DPBS; GIBCO) (200 µL) to the wells and spin at 1,500 rpm for 5 mins to wash. Prewarmed TrypLE Express (100 µL; GIBCO) was added and the cells were place at 37° C. for 15 min. FACS Buffer (DPBS supplemented with 5% HI-FBS and 0.1% sodium azide (SIGMA)) was added and the cells were washed twice. The cells were resuspended in 30 µL of 10 µg/mL human IgG and incubated at RT for 10 mins. During this time, MoDCs were added to the compensation plate and the appropriate antibody was added. Antibody mastermix in FACS buffer+azide (100 µL) and FMO (fluorescence minus one) controls were added, and the cells were incubated at 4° C. for 20 min. Antibodies to cell surface markers CD14, CD40, CD206, CD163, CD68, CD80, HLA-DR, CD274 (PD-L1) were used. Cells were washed twice with FACS Buffer then resuspended in FACS Buffer (100 µL) and samples were acquired on a flow cytometer. Data were analyzed on Flow Jo v9.

Figure 7:
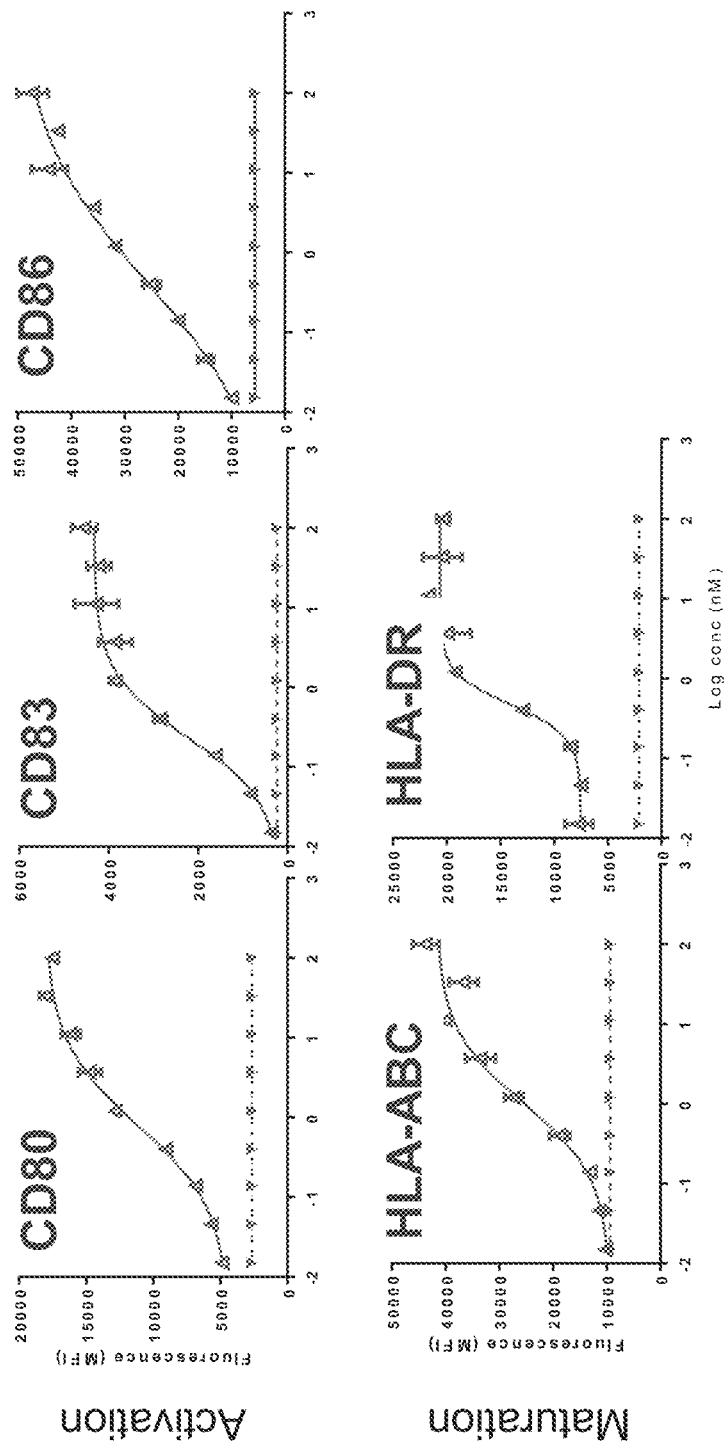
FIG. 7 is a set of graphs showing that MEDI5083 activated and matured human Monocyte-derived Dendritic Cells (MoDC). Activation was shown by increases in the markers CD80 (top left), CD83 (top center), and CD86 (top right). Maturation was shown by increases in the markers HLA-ABC (bottom left) and HLA-DR (bottom center).

MEDI5083 induced high levels of cell surface markers HLA-ABC, HLA-DR, CD80 and CD86, which are associated with antigen presentation, and CD83, an activation antigen (see FIG. 7 and Table 5).

TABLE 5

EC50 values

| Marker | EC50 (nM) |
|---|---|
| CD80 | 0.813 |
| CD83 | 0.234 |
| CD86 | 0.447 |
| HLA-ABC | 0.988 |
| HLA-DR | 0.473 |

High levels of additional cell surface markers were also observed, including CD40 and PD-L1, which are activation antigens, and the lymph node homing CCL19 and CCL21 receptor CCR7. Expression of all MoDC cell surface markers increased in a dose responsive manner, plateauing between 3.7 and 11.1 nM, though CD40 expressed appeared to be down regulated at high concentration. Thus, MEDI5083 was able to activate and mature human Monocyte-derived Dendritic Cells (MoDC). These experiments demonstrate that MEDI5083 can activate innate immunity.

Figure 8:
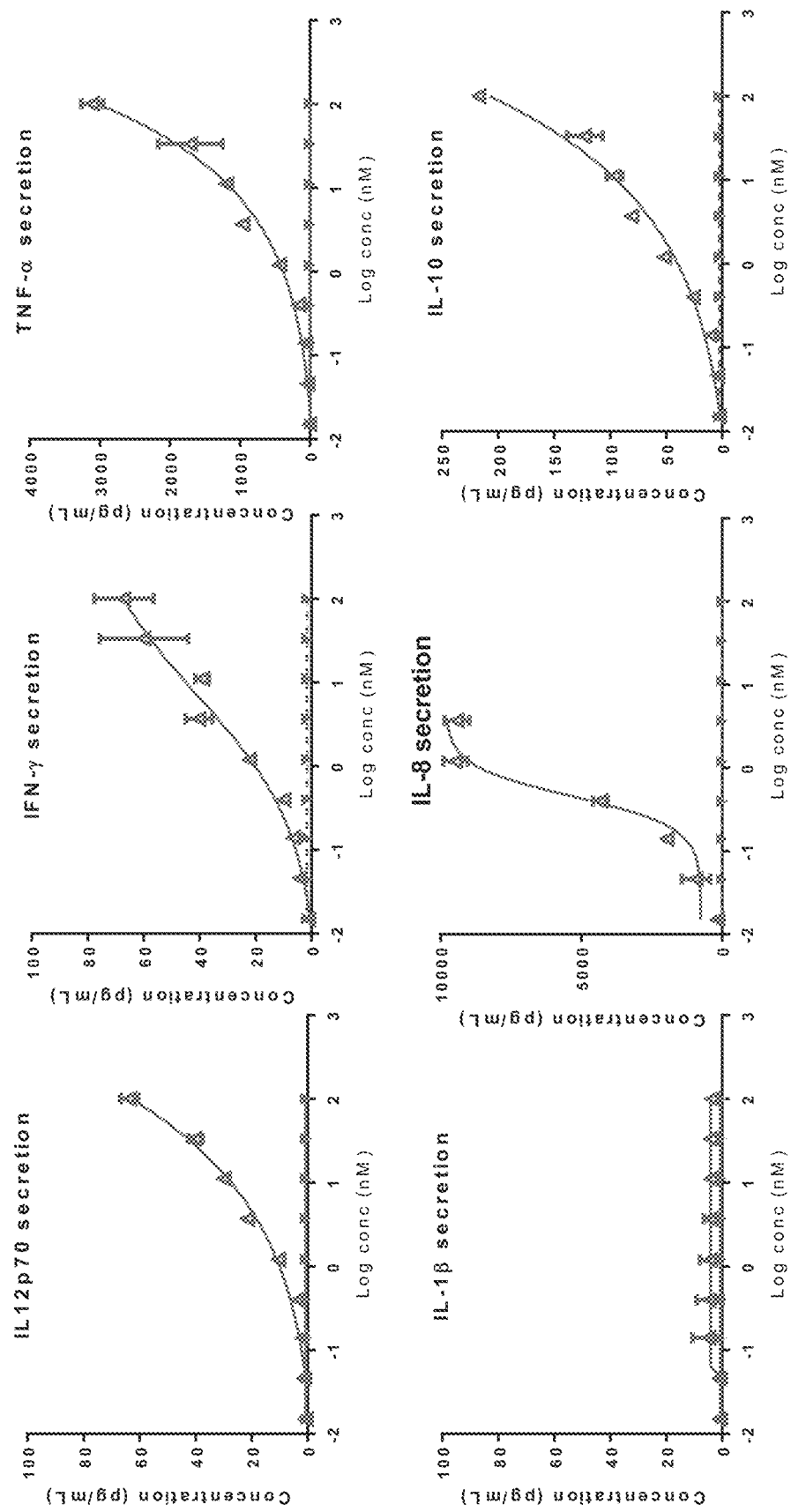
FIG. 8 is a set of graphs showing that MEDI5083 induced a Th1 Cytokine/Chemokine response in human Monocyte-derived Dendritic Cells (MoDC). Increases in secretion of IL12p70 (top left), IFNγ (top center), TNF-α (top, right), IL-8 (bottom center), and IL-10 (bottom right) are shown. No increase in secretion of IL-1β (bottom left) was observed.
Figure 9:
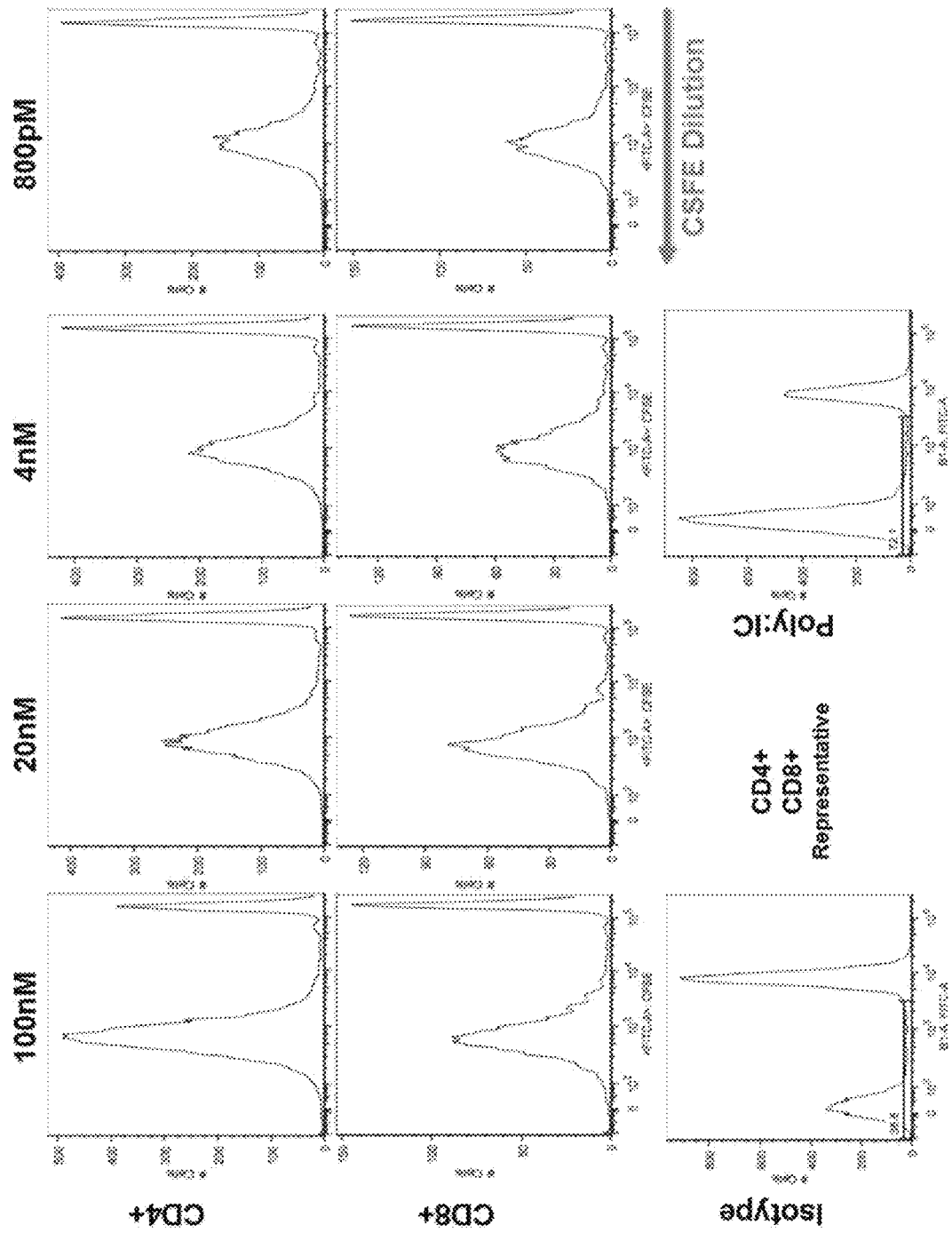
FIG. 9 is a set of fluorescence-activated cell sorting (FACS) histograms showing that MEDI5083 drove T cell proliferation via mDC activation and maturation in a dose dependent manner. In vitro proliferation of human CD4+ (top row) and CD8+(middle row) lymphocytes were monitored by flow cytometry with carboxyfluorescein diacetate succinimidyl ester (CFSE) dilution.

MEDI5083 induced a dose dependent increase in the secretion of IL-12p70, IFN-γ, TNF-α and IL-10 (FIG. 8). IL-8 secretion was initially induced but was inhibited at doses of 3.7 µM and above. No impact on IL-1β was observed for MEDI5083. In another experiment, mDC activation and maturation by MEDI5083 drove T cell proliferation in a dose dependent manner (FIG. 9). Thus, MEDI5083 was able to induce a Th1 cytokine/chemokine response in human MoDCs and to drive T cell proliferation. These experiments show that MEDI5083 has the potential to bridge innate and adaptive immune responses.

Example 4. The CD40L-Fc Fusion Protein MEDI5083 Activated Human Macrophage Polarization Monocytes are extremely plastic and can be differentiated macrophages with either a pro-inflammatory M1 phenotype or suppressor/wound healing M2 phenotype in-vitro. M1 macrophages are PDL1hi/CD80hi/CD40hi/HLA-DRhi/CD206lo/CD163lo/CD1410 while M2 macrophages are PDL1lo/CD80lo/CD40lo/HLA-DRlo/CD206hi/CD163hi/CD14hi. Additionally M1 macrophages produce the inflammatory cytokines TNF-α, IL-1β, IL-6, IL-12 and IL-23 while M2 macrophages produce the suppressive cytokines IL-10 and TGF-β. In a tumor setting, M2 macrophages may suppress the immune response to cancer antigens. Switching polarization towards an M1 phenotype could override this effect and enable tumor regression. This experiment was designed to evaluate the effects of MEDI5083, a human CD40L/human IgG4 fusion protein, on M1 and M2 polarized macrophages.

Materials and Methods

Monocyte handling and polarization protocol (Mia et al. (2014) Scan J Immunol 79: p 305-314)

Fresh human monocytes (Allcells) from 2 donors (D1: 8367; D2: 8375) were obtained for use in the experiment. A cell count was performed and a cell aliquot ($1 \times 10^6$) was removed for D0/resting monocyte FACS baseline. Remaining cells were split into two equal aliquots, the cells were spun down (1,500 rpm, 5 mins), and half were resuspended in M1 medium (RPMI (RPMI 1640+Glut media; GIBCO) supplemented with 10% Heat-inactivated FBS (HI-FBS; GIBCO), Pen Strep (GIBCO) (=cRPMI) and 50 ng/mL GM-CSF (R&D Systems)) and half were resuspended in M2 medium (cRPMI plus 50 ng/mL M-CSF (R&D Systems)). Aliquots (2 mL) were transferred to the wells of 6-well plates and the plates were incubated at 37° C. for 6 days, adding fresh cytokines every 2 days. An attachment step in serum-free media was removed from the published protocol. Each time cytokines were added cell morphology was noted and recorded.

After 6 days, the macrophages polarized towards either M1 or M2. Addition of activation stimulus resulted in characteristic cytokine secretion and cell surface marker upregulation. For this study, activation was performed in three ways:

(a) Standard activation (50 ng/mL LPS (LPS E. coli 0111:B4; SIGMA)+20 ng/mL IFN-γ (R&D Systems) to M1 plate and 20 ng/mL IL-4 (R&D Systems)+20 ng/mL IL-10 (R&D Systems) to M2 plate) added on day 6, with Fluorescence-activated cell sorting (FACS) analysis and harvest of supernatant after 24 hours.

(b) Standard activation plus simultaneous addition of MEDI5083 (4 nM; MedImmune) or isotype control (4 nM; MedImmune) added on day 6, with FACS analysis and harvest of supernatant after 24 hours.

(c) Standard activation added on day 6, MEDI5083 (4 nM; MedImmune) or isotype control (4 nM; MedImmune) added after 24 hours (day 7) with FACS analysis and harvest of supernatant after a further 24 hours.

At time of harvest, supernatant (500 µL) was removed and frozen for subsequent cytokine analysis by MSD (human TH1/TH2 10-plex plate IL-1β, IL-2, IL-4, IL-5, IL-8, IL-10, IL-12p70, IL-13, IFN-γ and TGF-β).

The remaining media was aspirated and plates were washed once with DPBS (DPBS w/o Ca/Mg; GIBCO) and pre-warmed TrypLE Express dissociation buffer (0.5 mL; GIBCO) was added to each well. The cells were placed in a 37° C. incubator for 20 min., plates were tapped to dislodge macrophages, cRPMI (2 mL) was added and aspirated vigorously using a 5 mL pipette to harvest cells. Following the procedure, wells were checked under a microscope for removal of the cells. Cells were spun down, adjusted to $1 \times 10^6$ cells/mL in cRPMI and processed for FACS.

Extracellular FACS Staining Protocol (4C)

Cells ($2 \times 10^5$) were added to the wells of a round bottomed 96-well plate and spun down at 1500 rpm for 5 mins. FACS Buffer (DPBS (DPBS w/o Ca/Mg; GIBCO) supplemented with 5% HI-FBS (GIBCO) and 0.1% sodium azide (SIGMA)) was added (200 µL) and the cells were washed once. The cells were resuspended in 50 µL of 1:4 TruStain FcX (BioLegend) Fc receptor block and incubated at room temperature for 10 min. Antibody panel mastermix (100 µL) was added to the wells and the cells were incubated at 4° C. for 20 min. Antibodies to cell surface markers CD14, CD40, CD206, CD163, CD68, CD80, HLA-DR, CD274 (PD-L1) were used. Cells were washed twice with FACS Buffer, resuspended in FACS Buffer (100 µL) and samples were acquired on a MACSQuant flow cytometer. The data were analyzed on Flow Jo v9.

Figure 10:
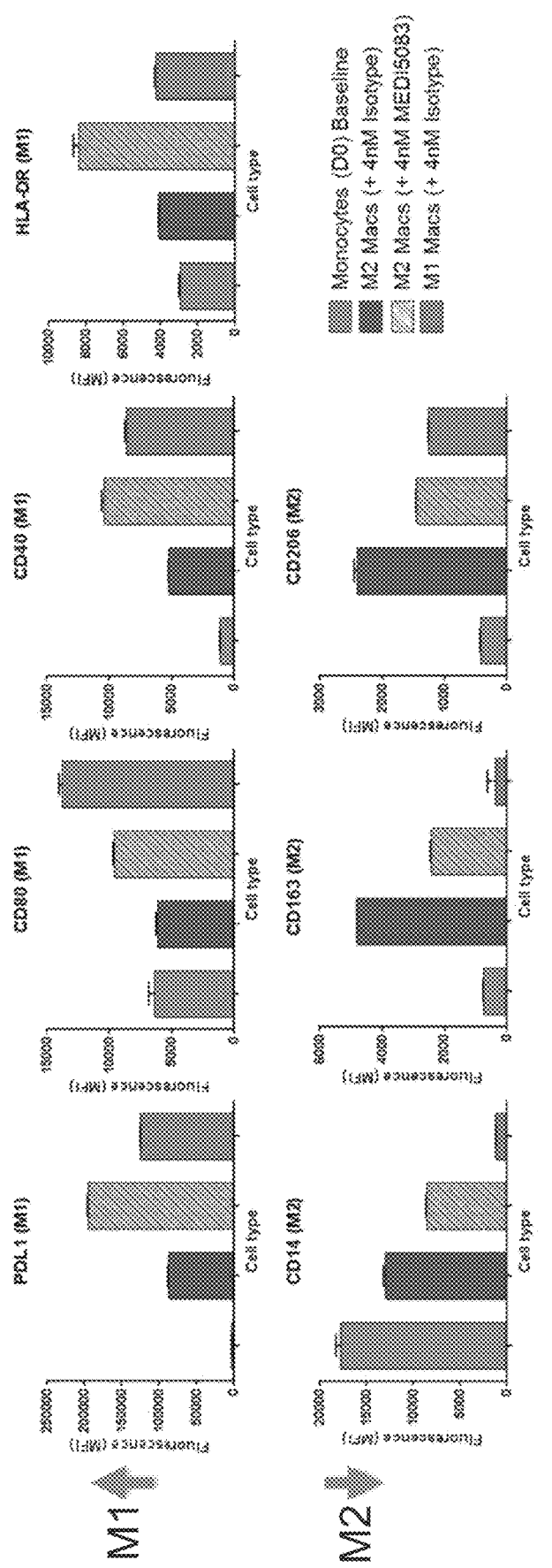
FIG. 10 is a set of graphs showing that MEDI5083 shifted human Suppressive (M2): Stimulatory (M1) macrophage ratios towards an immunostimulatory phenotype.
Figure 11:
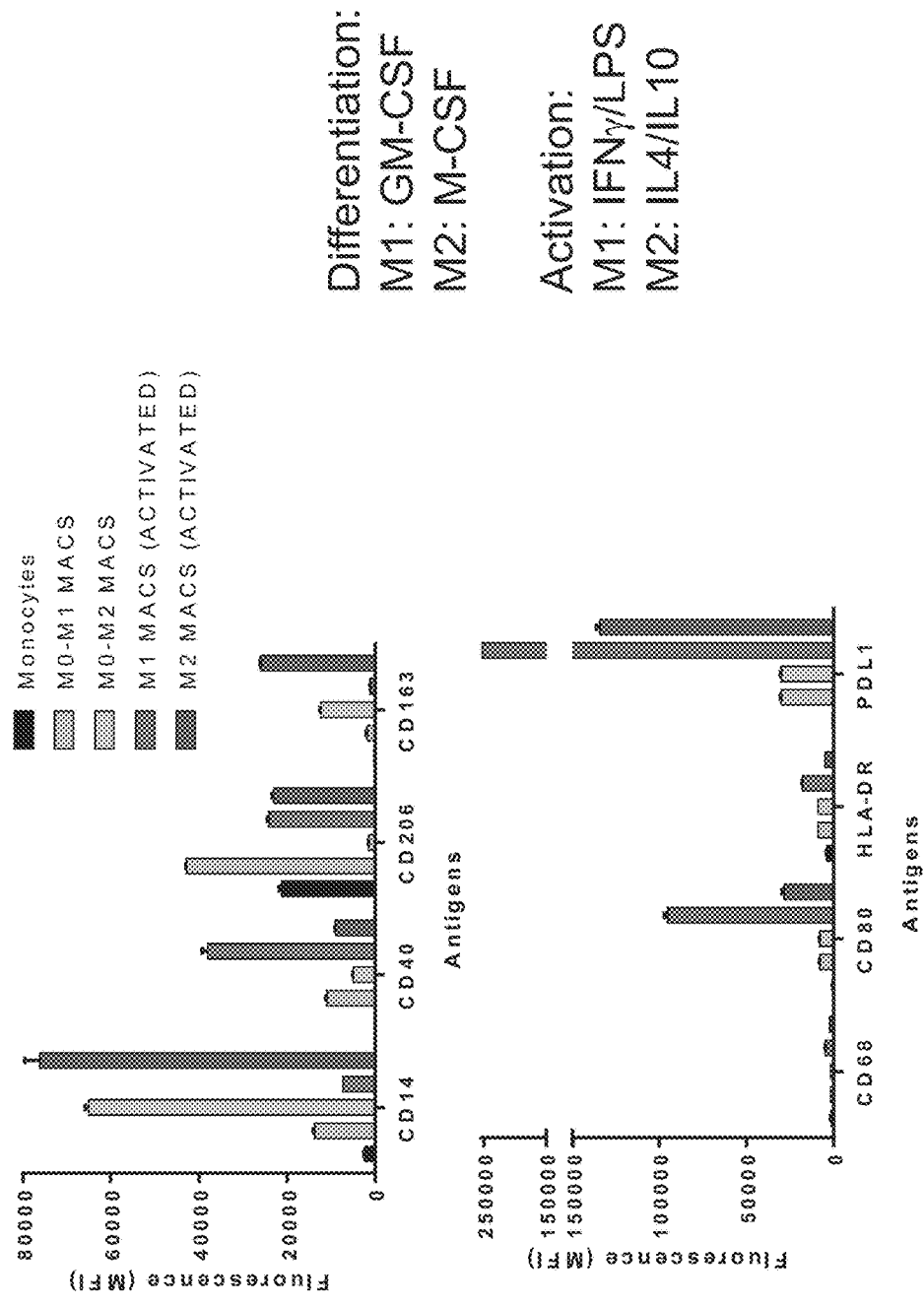
FIG. 11 are a set of graphs depicting human monocyte-derived macrophage M1/M2 polarization.

After 6 days in GM-CSF, macrophages are termed M0-M1. Activation for 24 hours with IFN-γ and LPS leads to full M1 polarization. Likewise, after 6 days in M-CSF, macrophages are termed M0-M2 and activation for 24 hours with IL-4 and IL-10 leads to full M2 polarization. Importantly, after 6 days (prior to activation) when viewed under the microscope, M0-M1 macrophages had the classic flattened down, pancaked morphology and M0-M2 macrophages had the classic adherent, spindle-like cells. In M2 macrophages, inclusion of MEDI5083 (4 nM) in the 24 hr activation phase increased M1 markers and decreased M2 markers shifting polarization away from M2 and towards M1 (FIG. 10, hatched bars; FIG. 11). Thus, these experiments showed that MEDI5083 was able to reverse immunosuppression.

Example 5. The CD40L-Fc Fusion Protein MEDI5083 Specifically Bound CD40

The mode of action of FP6 (MEDI5083) is largely through activation of CD40 expressing antigen presenting cells (dendritic cells, B-cells, monocytes and macrophages). FP6 does not bind other TNF receptor sub family proteins such as GITR, TRAIL and OX40 and is species specific (does not function in a mouse model).

A simple ELISA was developed to evaluate the human CD40 specificity of FP6 (MEDI5083). An earlier attempt to develop a simple ELISA based protocol demonstrated the need to use a more specific anti-human IgG4 secondary reagent to bypass non-specific binding to the Fc component of the receptor/Fc fusion proteins used to control the assay specificity. Additionally, effective lower concentrations of receptor and primary reagent were determined. In the present study, a more specific secondary reagent was evaluated.

Materials and Methods

TNF Receptor Binding Assay

Figure 12:
FIG. 12 is a graph showing that MEDI5083 is highly specific for human CD40.

Recombinant Fc chimera receptors, except for TRAIL, which has no Fc component, (50 μL of 5 μg/mL) were coated onto plates (1 hour, 37° C.), followed by a washing step (3× with PBS+0.05% Tween). Recombinant receptors included: rhCD40 (hIgG1 Fc); rmCD40 (hIgG1 Fc); rhGITR (hIgG1 Fc); rhTRAIL; rhOX40 (hIgG1 Fc) (R&D Systems). Recombinant receptors alone (no primary) were used as a control to check for direct binding to the Fc-HRP secondary reagent. The plates were blocked with 4% milk in PBS (1 hour, 37° C.), followed by a washing step (2× with PBS). Plates were incubated with primary reagent (50 μL of 20 nM) in 1% BSA PBS, e.g., freshly made, (1 hour, 37° C.), followed by a washing step (4× with PBS+0.05% Tween). Primary reagents included FP6 (hIgG4 Fc) and human IgG4 antibody, which was used as an isotype control. Plates were incubated with secondary reagent, HRP conjugated anti-Fc (100 μL of 1:25000) in 4% milk in PBS, followed by a washing step (4× with PBS+0.05% Tween). To prepare HRP conjugated anti-Fc, a 1:4 stock of mouse anti-human IgG4 (H+L) (Thermo cat no. MA1-34437) was made in 4% milk, diluted 1:5000, and 0.5 mg/mL was used at 1:25000. TMB (3,3',5,5'-tetramethylbenzidine) solution was added (100 μL/well). TMB solution was made by adding equal volumes of RT Solution A to Solution B (TMB substrate reagent kit; BD OptEIA cat. no. 3 555214) no more than 15 minutes prior to addition. The reactions were incubated at room temperature for 15 minutes and protected from light. Wells with HRP activity turned blue. Stop solution (2N sulphuric acid; 100 μL) was added, and wells that were turning blue turned bright yellow. The plates were read at 450 nm on a plate reader The FP6 (MEDI5083) ELISA assay worked well with high specificity for human CD40 (FIG. 12). Low background signal generated from the other human TNF receptor family members such as GITR, TRAIL and OX40, indicating that FP6 demonstrated high specificity for human CD40 over other human TNF receptor family members such as GITR, TRAIL and OX40. Thus, a simple ELISA was developed for assessment of the specificity of FP6 for human CD40.

The key component in this ELISA assay is the highly specific anti human IgG4 secondary reagent. Earlier attempts at generating an FP6-specific ELISA used a broader reactive anti human IgG secondary reagent that bound to the human Fc region of the receptor Fc fusion proteins used as target for FP6, leading to false positive signals.

A summary of the experiments described herein indicates that MEDI5083 specifically bound CD40 and activated key components of immune response in vitro (Table 6).

TABLE 6

MEDI5083 Specifically Binds CD40 and Activates Key Components of Immune Response

| In vitro assays | Potency |
|---|---|
| Human KinExA ($K_D$) | ND |
| Human CD40 NFκB (n = 10) | $EC_{50}$: 0.1 nM |
| Human B cell proliferation (n = 3) | $EC_{50}$: 0.2 nM |
| Human DC cell maturation/activation (n = 3) | Yes |
| Th-1 polarizing cytokine production by MoDC | Yes |
| Human monocyte/MF M2→M1 polarization | Yes |
| TNF Family Cross-reactivity (OX40, GITR, TRAIL) | None observed |

Example 6. MuCD40L-FP, a MEDI5083 Mouse Surrogate, Had Anti-Tumor Activity in a Mouse Tumor Model To study the effect of the CD40L-Fc fusion proteins in vivo in mice, a murine surrogate of MEDI5083, MuCD40L-FP, was constructed. Like MEDI5083, MuCD40L-FP comprises, from N- to C-terminus, a single chain fusion of 3× CD40L subunits connected via peptide linkers which is connected to an Fc polypeptide. However, in place of the human CD40L subunits and human IgG4P in MEDI5083, MuCD40L-FP comprises mouse CD40L subunits and a mouse IgG1 Fc. Additionally, in MuCD40L-FP, the intersubunit linkers between mouse CD40L subunits is GGGSGGS (SEQ ID NO: 37) compared to GGGGSGGGS (SEQ ID NO: 2).

Figure 13:
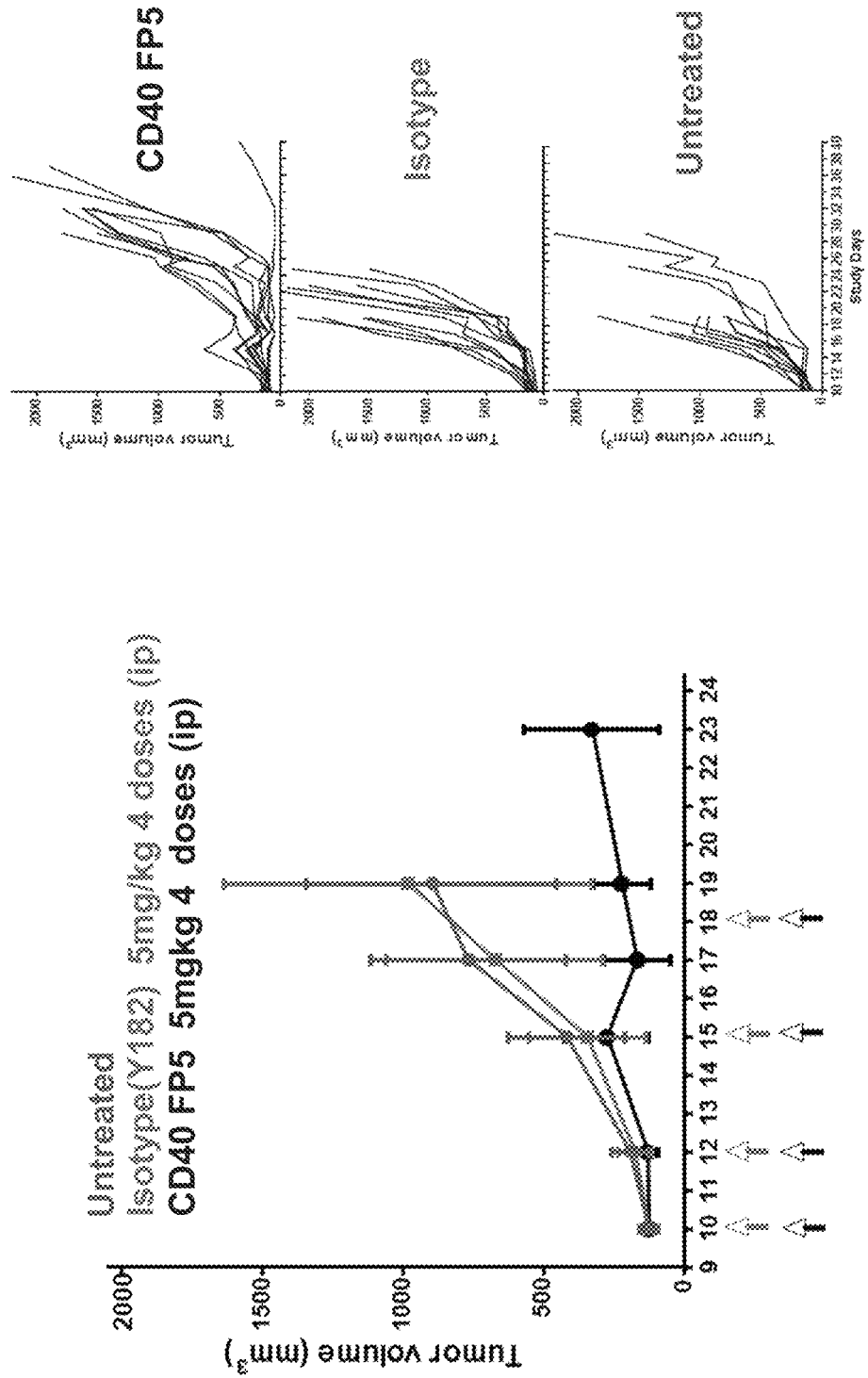
FIG. 13 is a series of graphs depicting that mouse surrogate CD40L-FP had significant anti-tumor activity in a low responsive tumor model. Average tumor volumes from each treatment group are plotted in the left and responses of individual mice are plotted on the graphs on the right.

Mouse surrogate CD40L FP was tested in a B16-F10 syngeneic mouse model. MuCD40L-FP decreased tumor volume and/or delayed tumor growth in the B16-F10 mouse model, compared to isotype and untreated controls (FIG. 13). Additionally, mice treated with MuCD40L-FP had no significant weight loss or other observable effects. Thus, MuCD40L-FP displayed significant anti-tumor activity in a low responsive tumor model.

Figure 14:
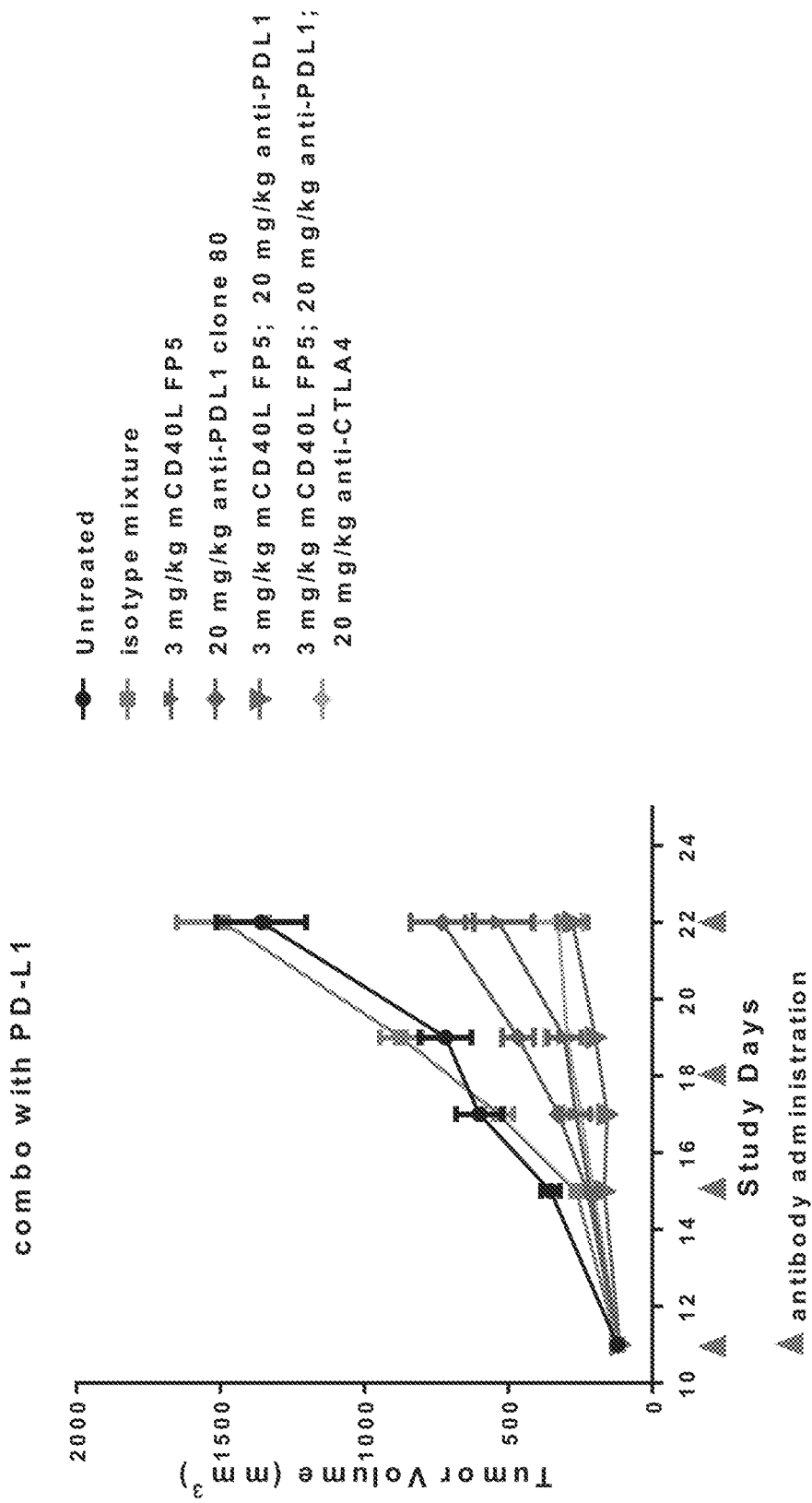
FIG. 14 is a graph depicting the anti-tumor activity of mouse surrogate CD40L-FP in combination with α-PD-L1 in a B16-F10 tumor model.
Figure 15:
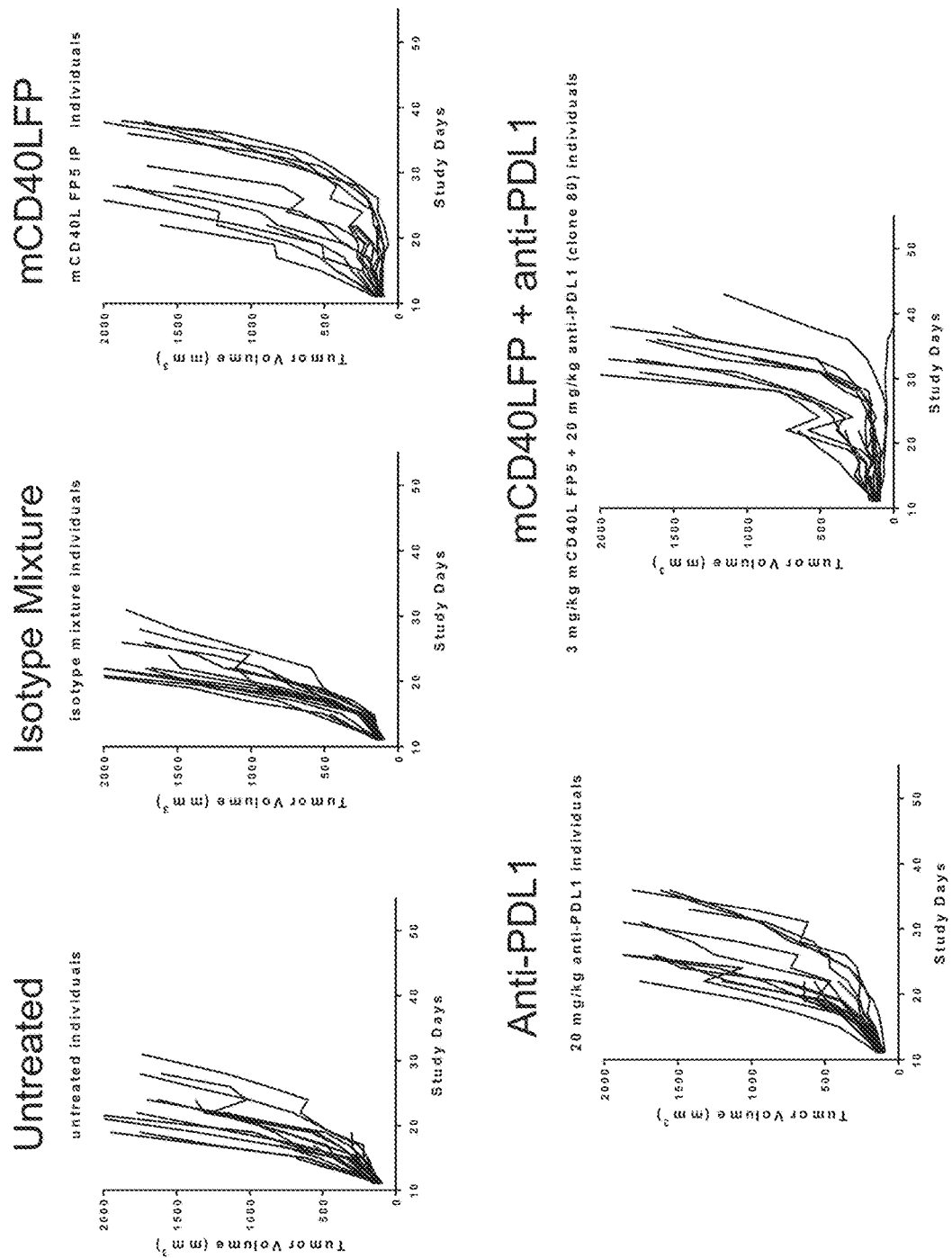
FIG. 15 is a series of graphs depicting the anti-tumor activity of mouse surrogate CD40L-FP in combination with α-PD-L1 in a B16-F10 tumor model. Responses of individual mice are plotted on the graphs.

Mouse surrogate CD40L FP was tested in combination with anti-PD-L1 in a B16-F10 syngeneic mouse model. MuCD40L-FP in combination with anti-PD-L1 decreased tumor volume and/or delayed tumor growth in individual mice in the B16-F10 mouse model, compared to anti-PD-L1 alone and isotype and untreated controls. (FIGS. 14 and 15).

Figure 16:
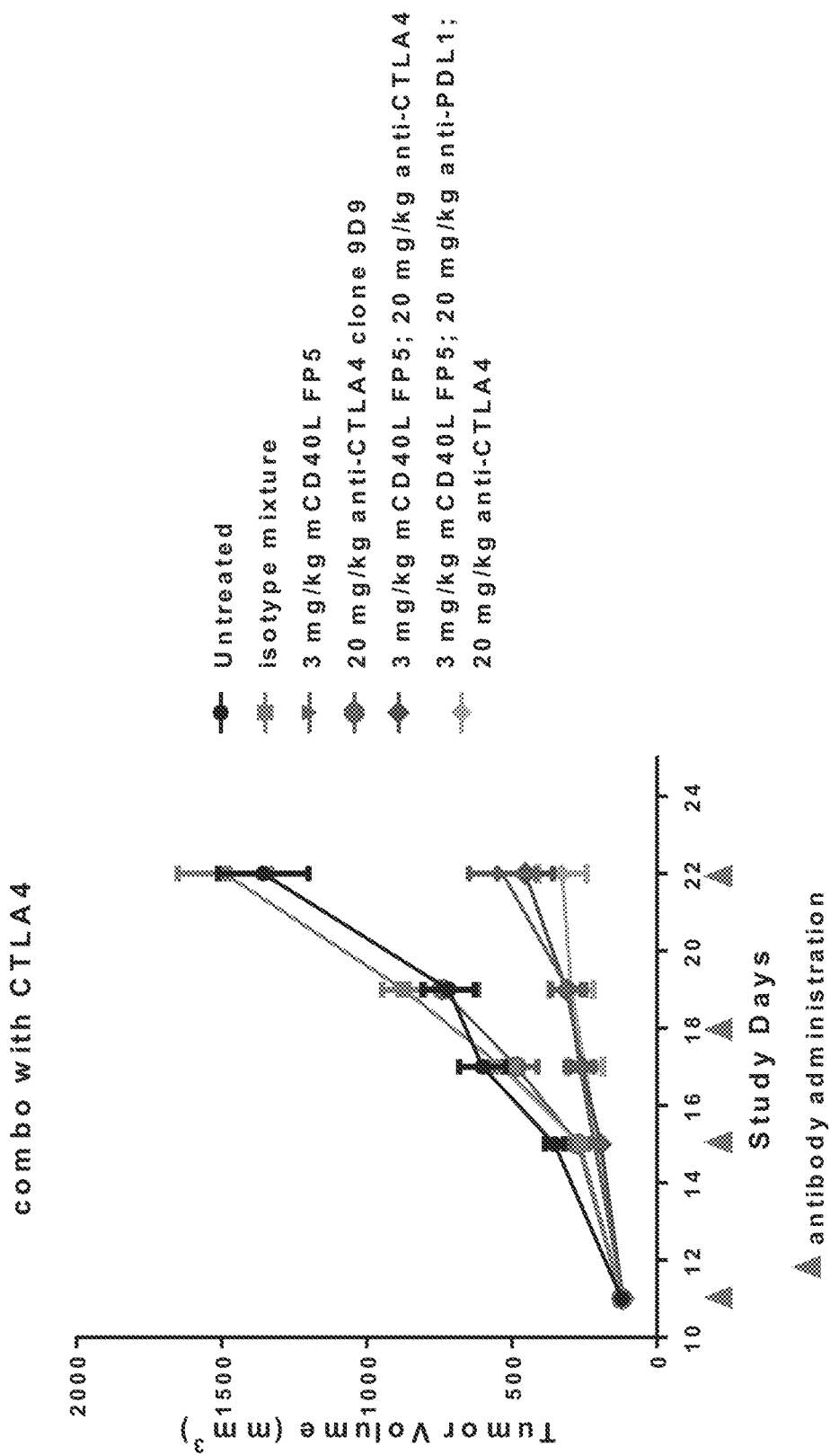
FIG. 16 is a graph depicting the anti-tumor activity of mouse surrogate CD40L-FP in combination with α-CTLA-4 in a B16-F10 tumor model.

Mouse surrogate CD40L FP was tested in combination with anti-CTLA-4 in a B16-F10 syngeneic mouse model. MuCD40L-FP in combination with anti-CTLA-4 decreased tumor volume and/or delayed tumor growth in individual mice in the B16-F10 mouse model, compared to anti-CTLA-4 alone and isotype and untreated controls. (FIGS. 16 and 17).

Figure 18:
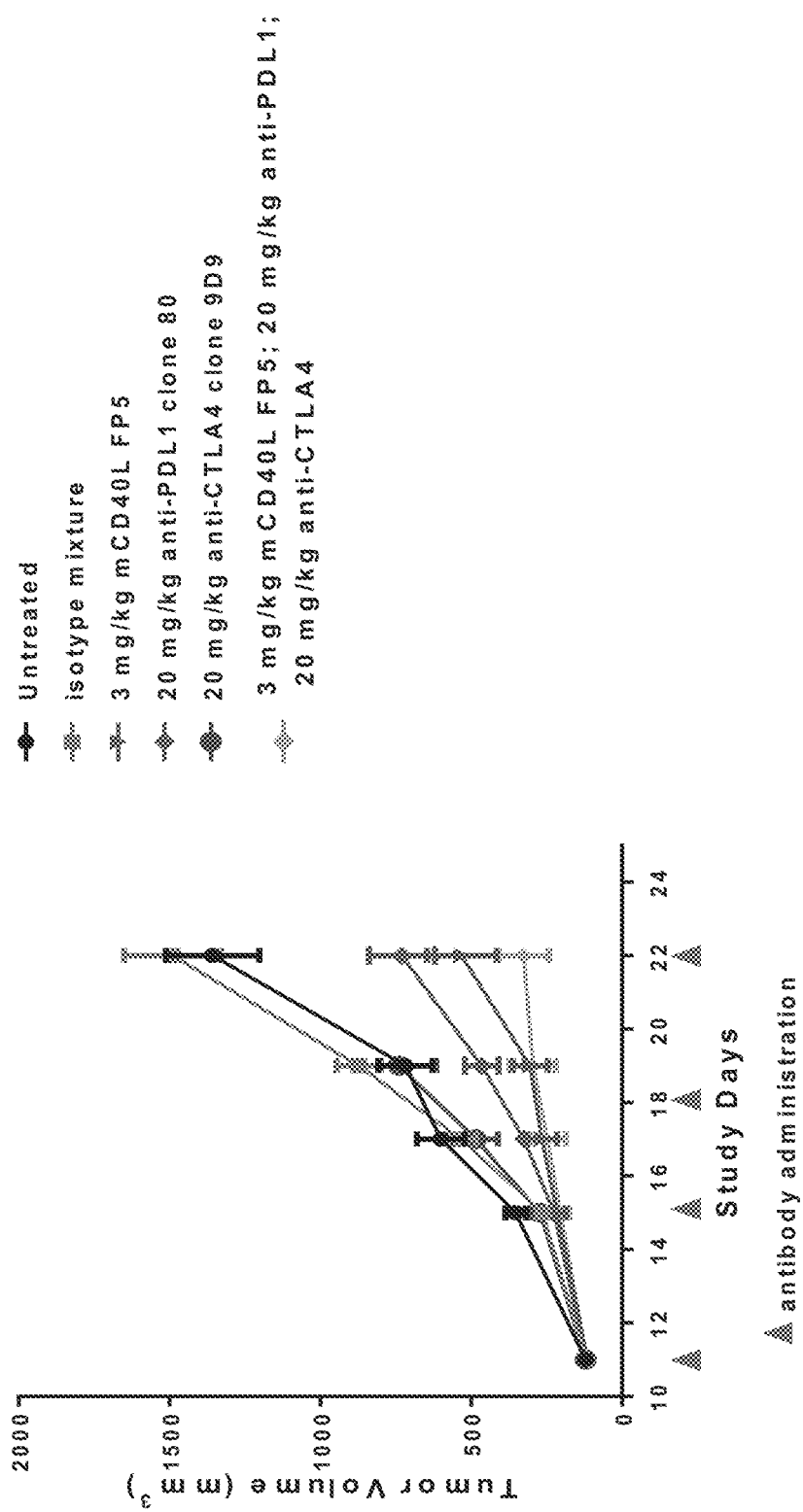
FIG. 18 is a graph depicting that mouse surrogate CD40L-FP in combination with α-PD-L1 halted tumor growth in a B16-F10 tumor model.
Figure 19:
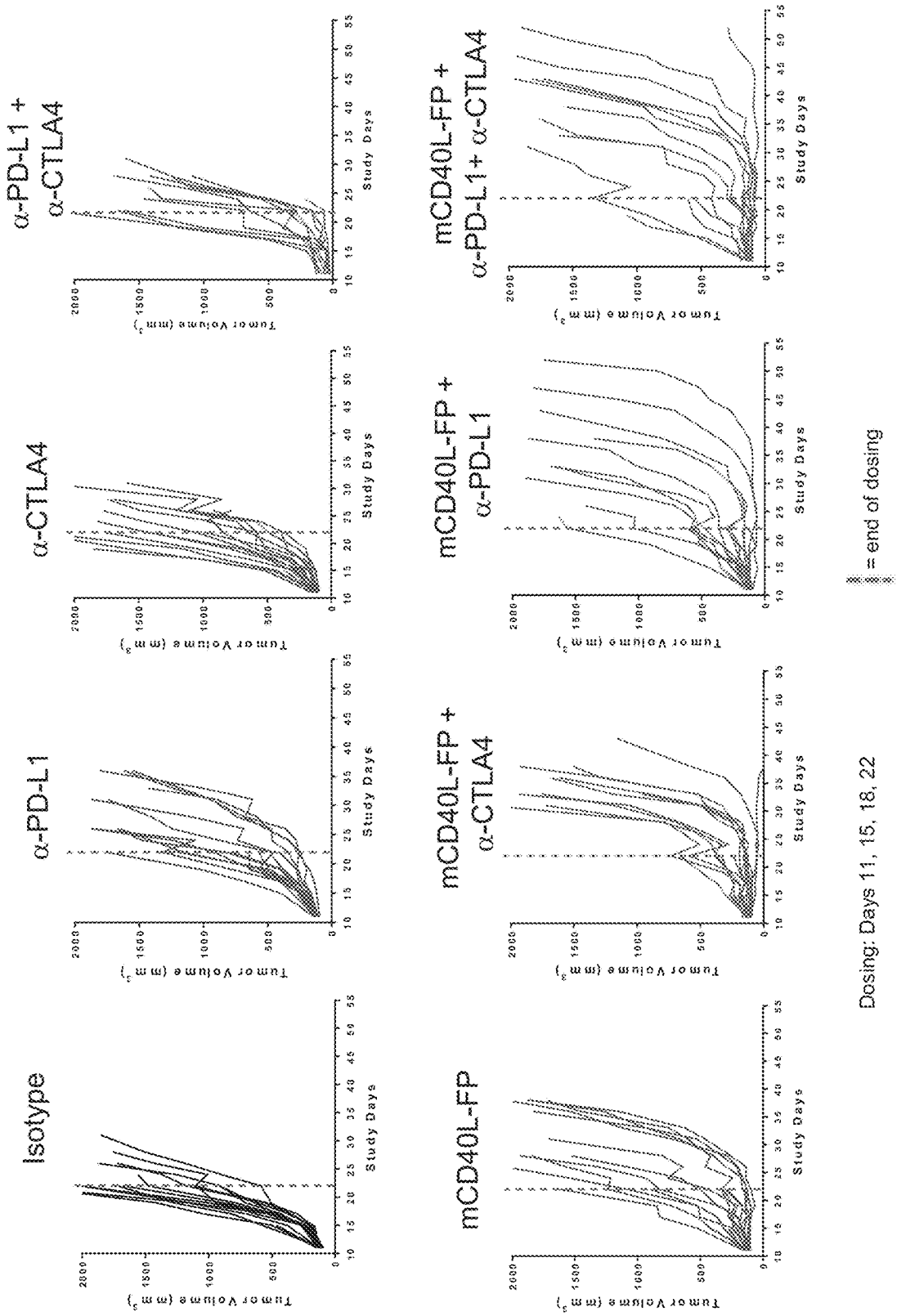
FIG. 19 is a series of graphs depicting the anti-tumor activity of mouse surrogate CD40L-FP in combination with one or more of α-PD-L1 and α-CTLA4.

Mouse surrogate CD40L FP was tested in combination with anti-PD-L1 and anti-CTLA-4 in a B16-F10 syngeneic mouse model. MuCD40L-FP in combination with anti-PD-L1 and anti-CTLA-4 decreased tumor volume and/or delayed tumor growth in individual mice in the B16-F10 mouse model, compared to the combination of anti-PD-L1 and anti-CTLA-4 or MuCD40L-FP with either anti-PD-L1 or anti-CTLA-4 (FIGS. 18 and 19).

Figure 20:
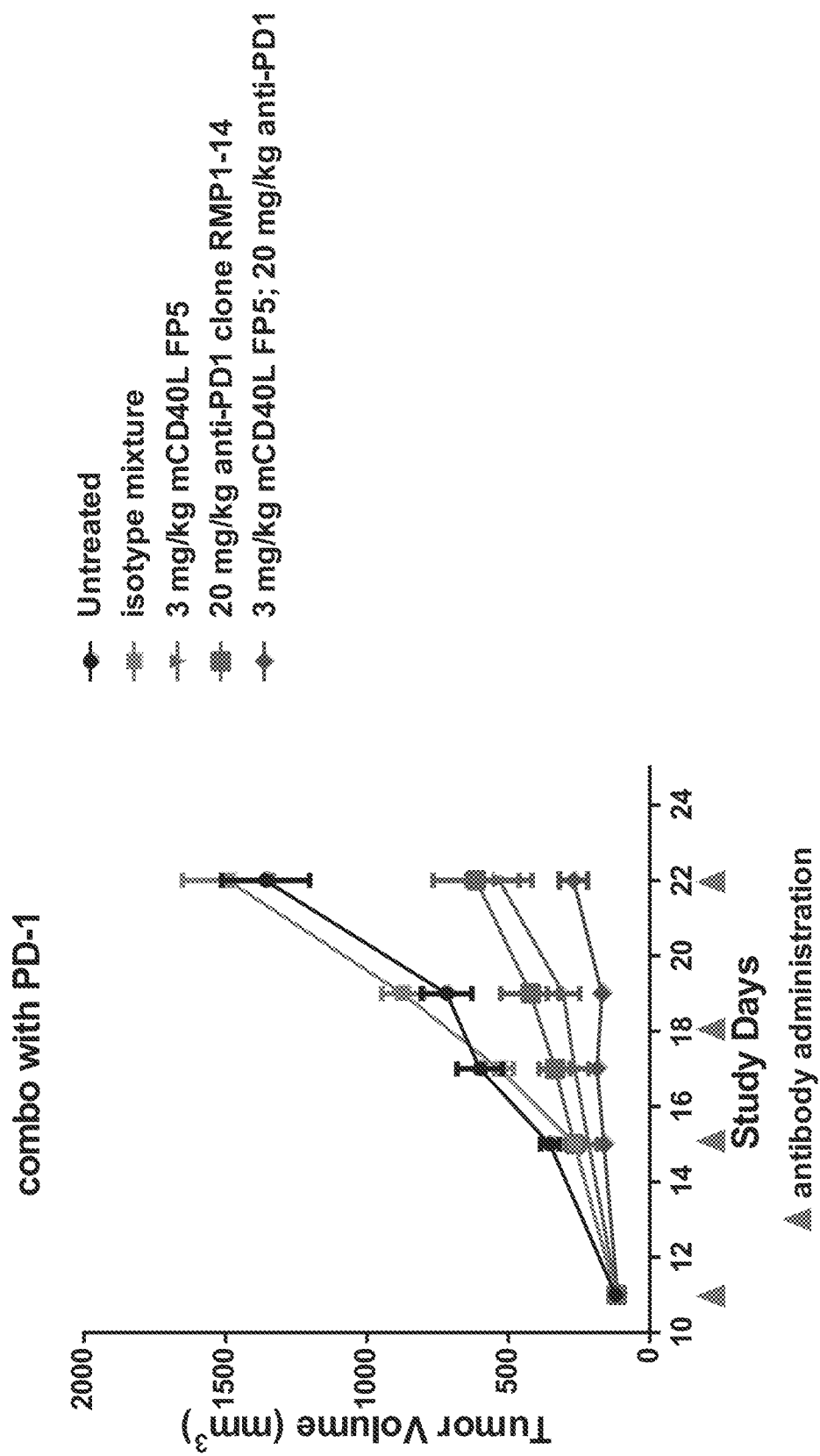
FIG. 20 is a graph depicting the anti-tumor activity of mouse surrogate CD40L-FP in combination with α-PD-1 in a B16-F10 tumor model.
Figure 21:
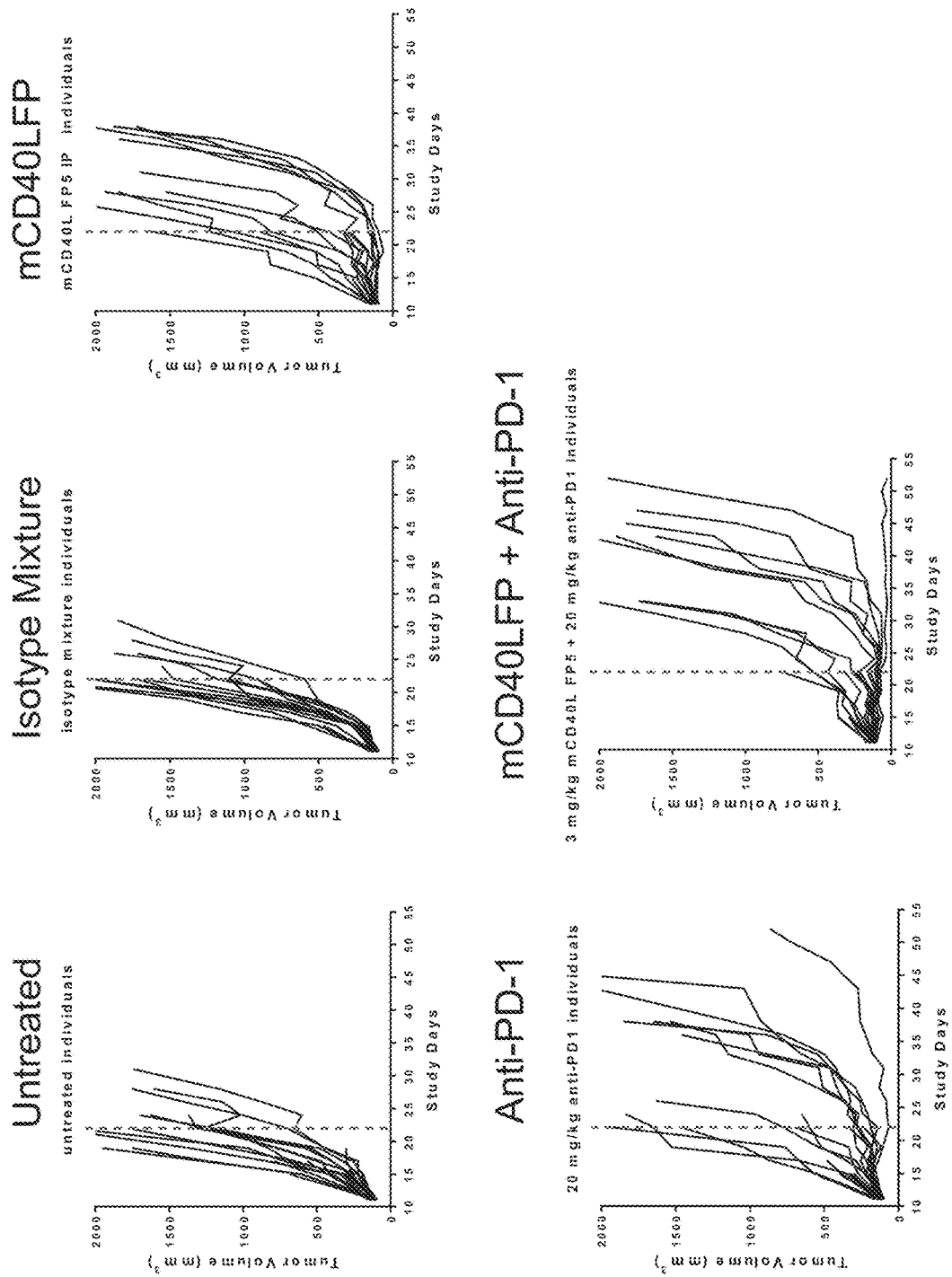
FIG. 21 is a series of graphs depicting the anti-tumor activity of mouse surrogate CD40L-FP in combination with α-PD-1 in a B16-F10 tumor model. Responses of individual mice are plotted on the graphs.

Mouse surrogate CD40L FP was tested in combination with anti-PD-1 in a B16-F10 syngeneic mouse model. MuCD40L-FP in combination with anti-PD-1 decreased tumor volume and/or delayed tumor growth in individual mice in the B16-F10 mouse model, compared to anti-PD-1 alone and isotype and untreated controls. (FIGS. 20 and 21).

Figure 22:
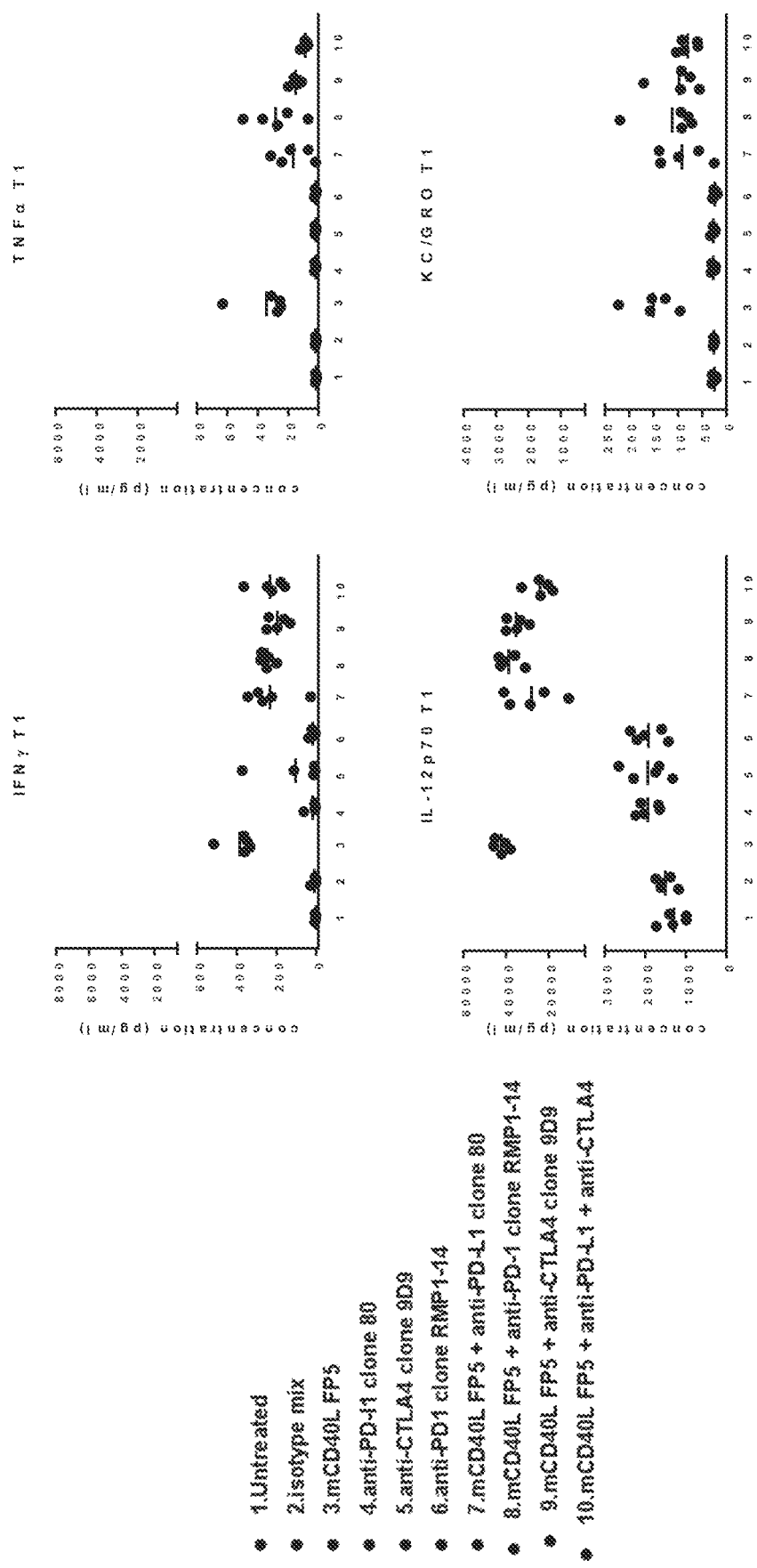
FIG. 22 is a series of graphs depicting mouse surrogate CD40L-FP induced serum cytokine/chemokine secretion in a B16-F10 tumor model. Increased levels of IFNγ (top left), TNF-α (top right), IL12 (bottom left) and KC/GRO (bottom right) were observed at 24 hours after the $2^{nd}$ dose (T1).
Figure 23:
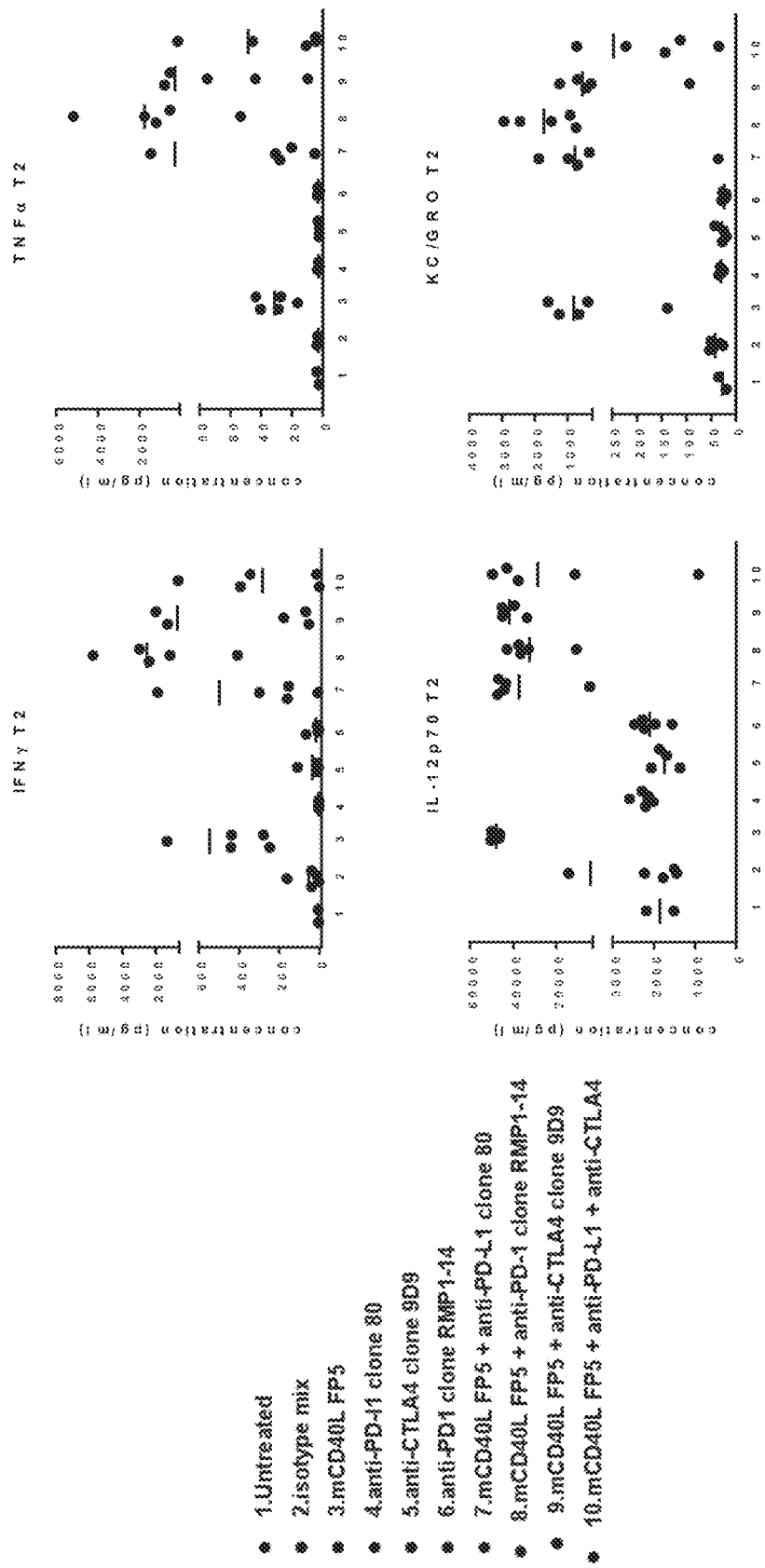
FIG. 23 is a series of graphs depicting mouse surrogate CD40L-FP induced serum cytokine/chemokine secretion in a B16-F10 tumor model. Increased levels of IFNγ (top left), TNF-α (top right), IL12 (bottom left) and KC/GRO (bottom right) were observed at 24 hours after the $4^{th}$ dose (T2).

In addition, serum were collected from B16-F10 tumor bearing mice treated with muCD40L-FP, anti-PDL-1, anti-CTLA-4, or anti-PD1 alone, or muCD40L-FP in combination with anti-PDL-1, anti-PD-1, anti-CTLA-4 or anti-PDL-1 and anti-CTLA4. Serum cytokine levels at 24 hours post $2^{nd}$ and $4^{th}$ treatment were measured with a Meso Scale Discovery multiplex assay kit. Treatment with muCD40L-FP alone or in combination with anti-PDL-1, anti-PD-1, anti-CTLA-4 or anti-PDL-1 and anti-CTLA4 induced elevated levels of TH1 cytokines IFNγ, TNFα, IL12 and KC/GRO T1, compared to anti-PD-L1, anti-CTLA-4, and anti-PD-1 alone and isotype and untreated controls 24 hrs after the $2^{nd}$ treatment (FIG. 22) and 24 hours after the $4^{th}$ treatment (FIG. 23). However, no changes in IL-1B, IL-2, IL-4, IL-5, or IL-10 were observed at 24 hrs after the $2^{nd}$ treatment or 24 hours after the $4^{th}$ treatment (data not shown).

Thus, MuCD40L-FP in combination with anti-PD-L1, anti-PD-1, anti-CTLA-4, either alone or in combination with anti-PD-L1 or anti-PD1, displayed significant anti-tumor activity in a low responsive tumor model. These data demonstrate the usefulness of MEDI5083 in combination with immune checkpoint inhibitors.

Figure 24:
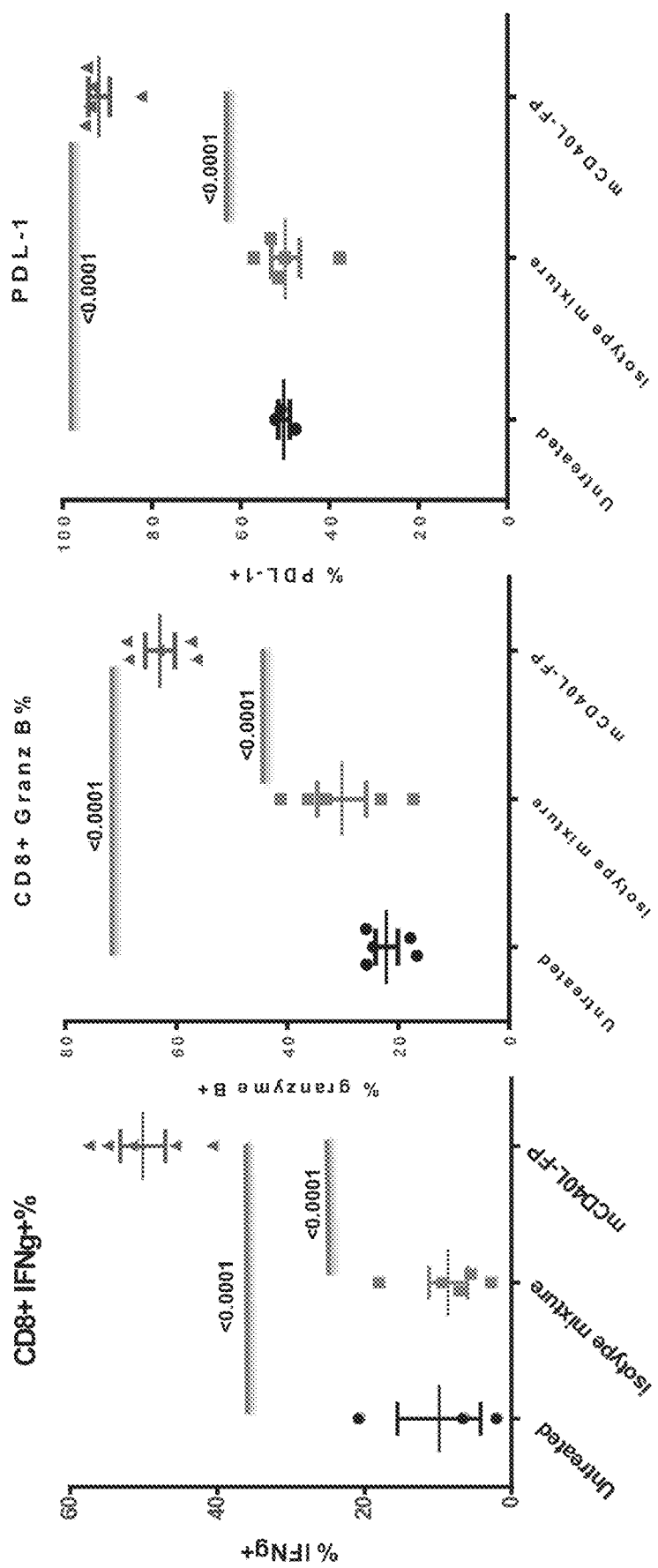
FIG. 24 is a series of graphs depicting that mouse surrogate CD40L-FP increased intratumoral $CD8^+$ T-cell Activation and PD-L1 expression in mice.
Figure 25:
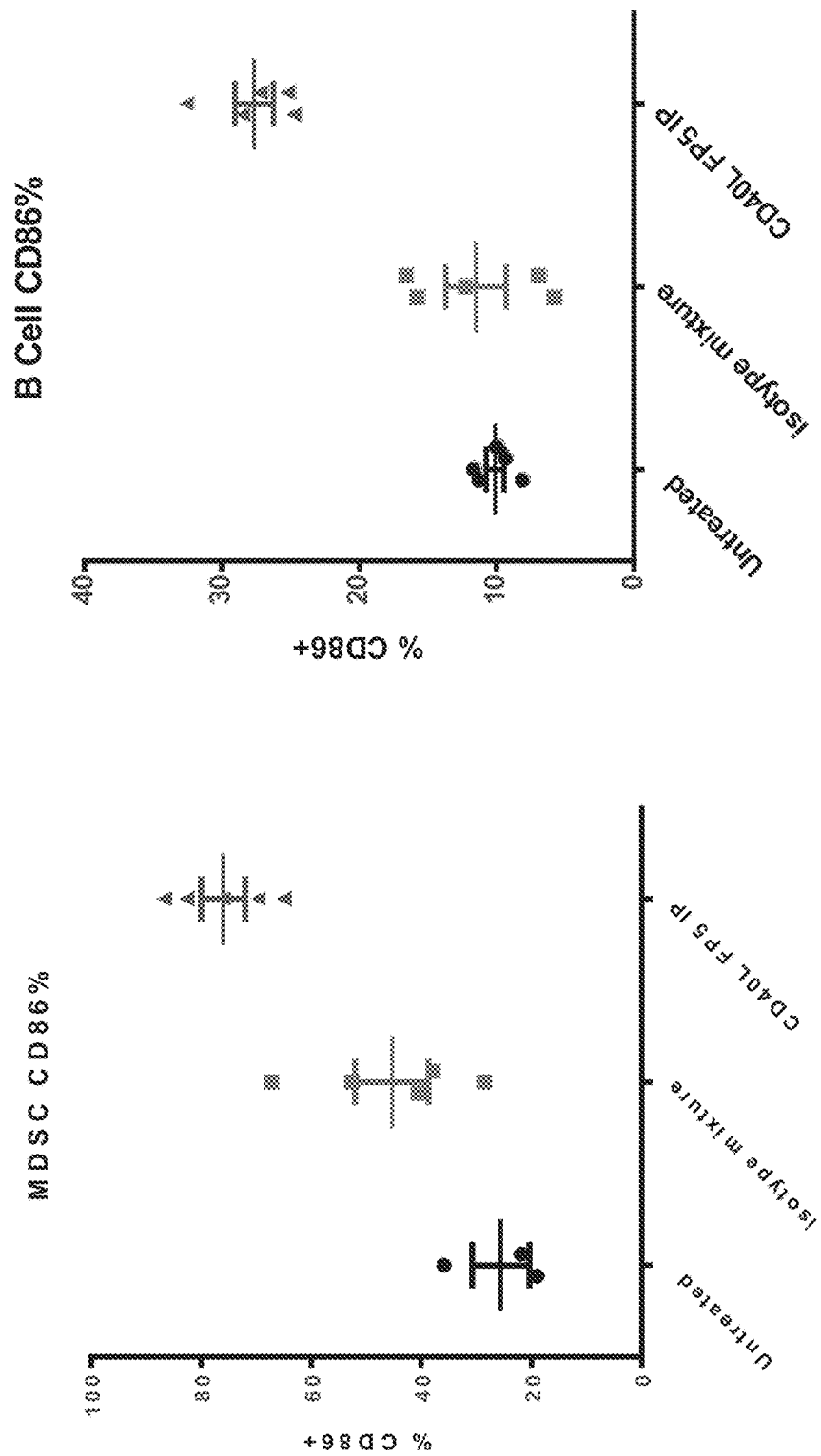
FIG. 25 are graphs showing that mouse surrogate CD40L-FP drove splenic myeloid cell maturation and B-cell activation in mice.
Figure 26:
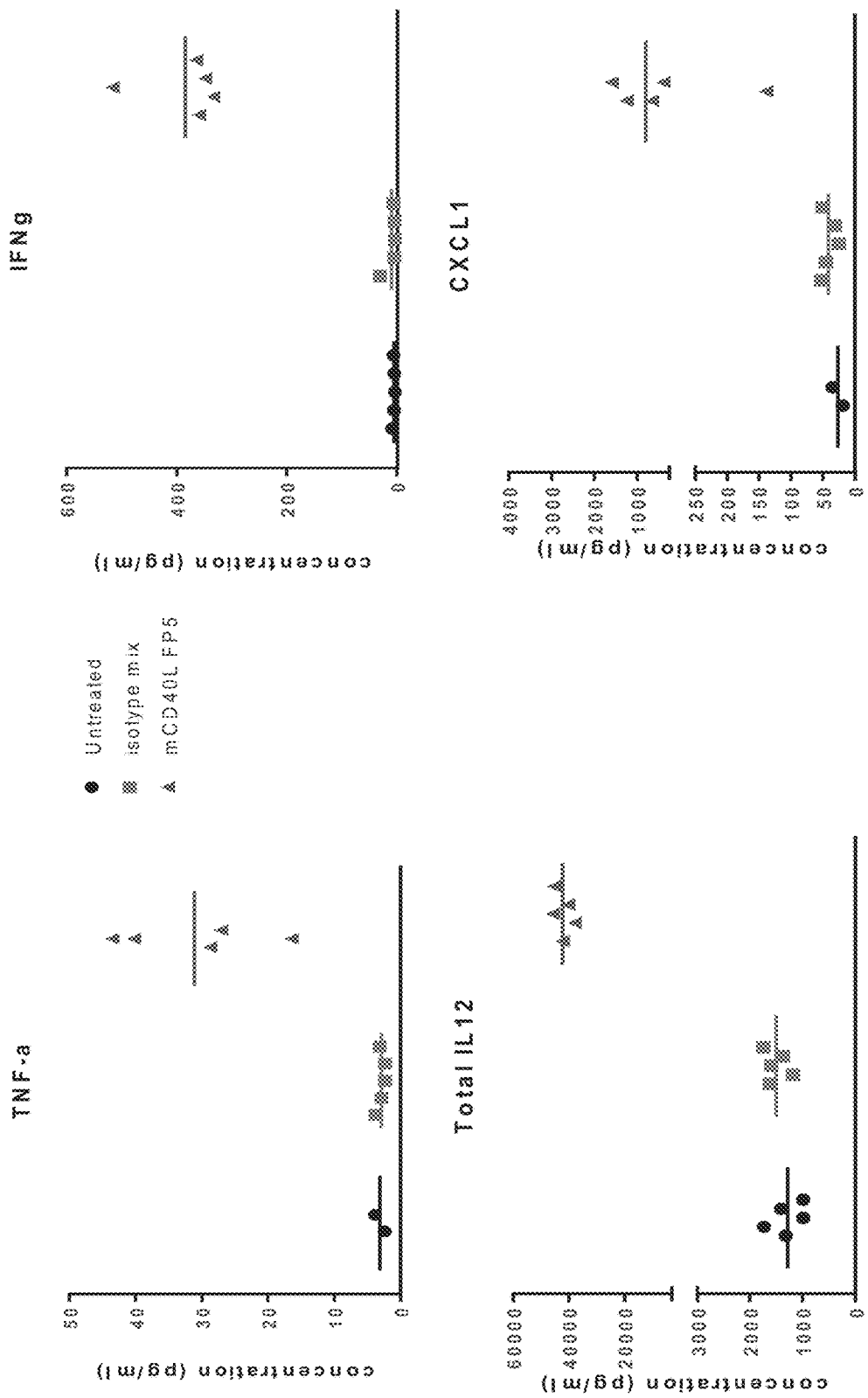
FIG. 26 is a series of graphs depicting mouse surrogate CD40L-FP induced TH1 cytokine and CXCL-1 chemokine secretion in mice.

Example 7. MuCD40L-FP, a MEDI5083 Mouse Surrogate, Activated Immune Responses in Mice To understand the effect of mouse surrogate MuCD40L-FP, immune responses in the B16-F10 mice were studied. MuCD40L-FP increased intratumoral $CD8^+$ T-cell activation and PD-L1 expression in mice, compared to untreated and isotype controls (FIG. 24). Mice administered MuCD40L-FP had increased total $CD8^+$ T cells and increased percentages of $CD8^+$, $IFN\gamma^+$; $CD8^+$, $GrazB^+$; and $PD-L1^+$ T cells, compared to control mice. In spleen, MuCD40L-FP drove myeloid cell maturation and B-cell activation in B16-F10 mice, compared to untreated and isotype controls (FIG. 25). MuCD40L-FP also induced TH1 cytokine and CXCL-1 chemokine secretion in B16-F10 mice (FIG. 26). Mice administered MuCD40L-FP had increased IFNγ, TNFα, IL-12, and CXCL1 secretion compared to control mice.

Example 8. MEDI5083 Pharmacokinetic (PK) and Pharmacodynamic (PD) Studies in Monkey To understand the effect of MEDI5083 in primates, pharmacokinetic (PK) and pharmacodynamic (PD) studies were performed in monkeys. A starting dose of 0.3 mg/kg was used based on published data with an agonistic mAb against CD40 (Vonderheide et al 2001), for which MEDI5083 has the same mechanism of action. The MTD for the published anti-CD40 mAb was 0.2 mg/kg. The equivalent cynomolgus MTD will be 3 times the human MTD; 0.6 mg/kg. A dose of 0.3 mg/kg or less was predicted to be a safe starting dose in cynomolgus macaques. A single dose PK/PD toxicology study showed no toxicity at any of the tested doses (Table 7).

TABLE 7

Single Dose PK/PD Toxicology Study (non-GLP)

| Group | mg/kg | Route | Doses | Animals |
| --- | --- | --- | --- | --- |
| 1 | Vehicle | IV & SC | 1 | 3M |
| 2 | 0.3 | IV | 1 | 3M |
| 3 | 3.0 | IV | 1 | 3M |
| 4 | 30.0 | IV | 1 | 3M |
| 5 | 30.0 | SC | 1 | 3M |

The administration routes were chosen because they are consistent with the proposed route of administration in humans and is expected to provide appropriate serum levels and be associated with phamacodynamic effect.

Blood (0.5-1.0 ml) was collected 4 hours after dosing. Blood was analyzed with specific monoclonal antibodies to detect B cells (including activated B cells), T cells (T helper-cells and cytotoxic T cells), natural killer (NK−) cells and dendritic cells. Relative cell numbers (percentage) were obtained and total lymphocyte counts were determined on the same day. Absolute numbers of the subpopulations were computed from relative and total numbers. Blood samples were also used for Ki67 immunostaining. Serum was used for analysis of cytokines, pharmacokinetic analysis and evaluation, and Anti-drug-antibody (ADA) studies.

Figure 27:
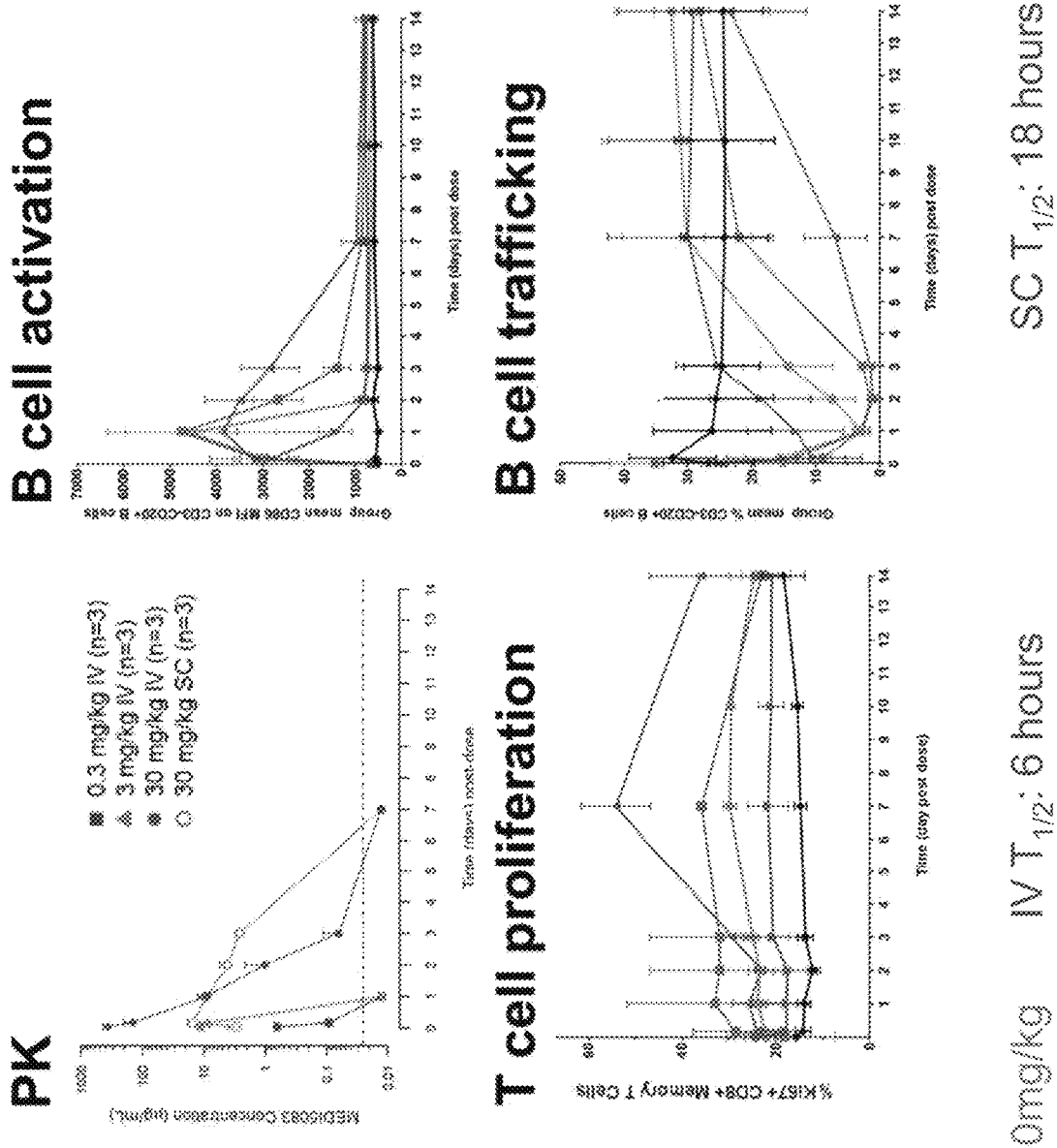
FIG. 27 is a series of graphs depicting pharmacokinetic and pharmacodynamic (PK-PD) models to describe B-cell activation and trafficking after MEDI5083 single dose in monkeys.

PK-PD models were generated to describe B-cell activation and trafficking after MEDI5083 single dose in monkeys (FIG. 27). PK results from the study are listed as follows: CL=405 mL/day/kg; $V_c$=137 mL/kg; $V_p$=122 mL/kg; $V_{max}$=496 μg/day; $V_{max}$=496 μg/day; and $K_m$=0.026 μg/mL. PD results from the study are listed as follows: $R_0$=1; $S_{max}$=6.32/day; $K_{out}$=8.13/day; and $EC_{50}$=0.08 μg/mL. MEDI5083 displayed a non-linear PK, with serum half-life in subjects ranging from 2.7 to 18 hrs. Interestingly, MEDI5038 administered SC had a longer half-life than when administered IV (30 mg/kg: IV $T_{1/2}$: 6 hrs; SC $T_{1/2}$: 18 hrs). $EC_{50}$ for B-cell activation was 0.08 μg/mL (~50 pM), which was consistent with $EC_{50}$ in vitro. MEDI5038 displayed a prolonged PD effect, as the half-life for B-cell trafficking was 36 hrs compared to a half-life for B cell activation of 2 hrs. MEDI5038 also activated T-cell proliferation ($CD8^+$ memory T cell Ki67) in monkeys (PD observed at 30 mg/kg SC, 7 days).

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A fusion protein comprising:
   (a) a single chain fusion selected from the group comprising amino acid sequences SEQ ID NO: 9, SEQ ID NO: 10, and SEQ ID NO: 11.

2. A dimer comprising two fusion proteins selected from the fusion proteins of claim 1.

* * * * *